United States Patent
Nirenberg

(10) Patent No.: US 9,302,103 B1
(45) Date of Patent: Apr. 5, 2016

(54) NEUROLOGICAL PROSTHESIS

(75) Inventor: Sheila Nirenberg, New York, NY (US)

(73) Assignee: Cornell University, Ithaca, NY (US)

( * ) Notice: Subject to any disclaimer, the term of this patent is extended or adjusted under 35 U.S.C. 154(b) by 529 days.

(21) Appl. No.: 13/230,488

(22) Filed: Sep. 12, 2011

Related U.S. Application Data

(60) Provisional application No. 61/381,646, filed on Sep. 10, 2010, provisional application No. 61/382,280, filed on Sep. 13, 2010.

(51) Int. Cl.
| | |
|---|---|
| *A61N 1/36* | (2006.01) |
| *G06N 3/04* | (2006.01) |
| *A61N 5/06* | (2006.01) |
| *A61N 1/05* | (2006.01) |
| *A61F 9/08* | (2006.01) |

(52) U.S. Cl.
CPC ............ *A61N 1/36003* (2013.01); *G06N 3/049* (2013.01); *A61F 9/08* (2013.01); *A61N 1/0543* (2013.01); *A61N 1/36046* (2013.01); *A61N 1/36067* (2013.01); *A61N 5/0622* (2013.01)

(58) Field of Classification Search
USPC ..................................................... 607/48, 54
See application file for complete search history.

(56) References Cited

U.S. PATENT DOCUMENTS

| | | | |
|---|---|---|---|
| 5,836,996 A | 11/1998 | Doorish | |
| 5,856,152 A | 1/1999 | Wilson et al. | |
| 6,400,989 B1 | 6/2002 | Eckmiller | |
| 6,458,157 B1 | 10/2002 | Suaning | |
| 6,530,954 B1 * | 3/2003 | Eckmiller | 623/11.11 |
| 6,533,798 B2 | 3/2003 | Greenberg et al. | |
| 7,149,586 B2 | 12/2006 | Greenberg et al. | |
| 8,103,352 B2 | 1/2012 | Fried et al. | |
| 8,956,396 B1 | 2/2015 | Friend et al. | |
| 2002/0161417 A1 | 10/2002 | Scribner | |
| 2003/0088081 A1 | 5/2003 | Maliga et al. | |
| 2003/0093129 A1 * | 5/2003 | Nicolelis et al. | 607/45 |

(Continued)

FOREIGN PATENT DOCUMENTS

| | | |
|---|---|---|
| CN | 101239008 A | 8/2008 |
| CN | 101336856 A | 1/2009 |

(Continued)

OTHER PUBLICATIONS

Asher, et al., "Image Processing for a High-Resolution Optoelectronic Retinal Prosthesis", IEEE Transactions on Biomedical, Engineering, vol. 54, No. 6, Jun. 2007, pp. 993-1004.

(Continued)

*Primary Examiner* — Carl H Layno
*Assistant Examiner* — Jennifer Ghand
(74) *Attorney, Agent, or Firm* — Foley & Lardner LLP

(57) ABSTRACT

A method improving or restoring neural function in a mammalian subject in need thereof, the method including: using an input receiver to record an input signal generated by a first set of nerve cells; using an a encoder unit including a set of encoders to generate a set of coded outputs in response to the input signal; using the encoded outputs to drive an output generator; and using an output generator to activate a second set of nerve cells wherein the second set of nerve cells is separated from the first set of nerve cells by impaired set of signaling cells. In some embodiments, the second set of nerve cells produces a response that is substantially the same as the response in an unimpaired subject.

20 Claims, 13 Drawing Sheets

(56) References Cited

U.S. PATENT DOCUMENTS

| | | | |
|---|---|---|---|
| 2003/0105409 A1* | 6/2003 | Donoghue et al. | 600/545 |
| 2004/0147975 A1* | 7/2004 | Popovic et al. | 607/48 |
| 2004/0176821 A1 | 9/2004 | Delbeke et al. | |
| 2005/0015120 A1 | 1/2005 | Seibel et al. | |
| 2006/0129207 A1 | 6/2006 | Fried et al. | |
| 2006/0184062 A1 | 8/2006 | Greenberg et al. | |
| 2006/0251621 A1 | 11/2006 | Campochiaro et al. | |
| 2007/0050046 A1* | 3/2007 | Georgopoulos | 623/24 |
| 2007/0261127 A1 | 11/2007 | Boyden et al. | |
| 2008/0021515 A1 | 1/2008 | Horsager et al. | |
| 2008/0021516 A1 | 1/2008 | Greenberg et al. | |
| 2008/0086206 A1 | 4/2008 | Nasiatka et al. | |
| 2008/0221653 A1 | 9/2008 | Agrawal et al. | |
| 2008/0234781 A1* | 9/2008 | Einav et al. | 607/48 |
| 2008/0249588 A1 | 10/2008 | Greenberg et al. | |
| 2008/0294217 A1 | 11/2008 | Lian et al. | |
| 2009/0088399 A1 | 4/2009 | Balya et al. | |
| 2009/0105786 A1* | 4/2009 | Fetz et al. | 607/48 |
| 2009/0118793 A1 | 5/2009 | McClure et al. | |
| 2009/0118794 A1 | 5/2009 | McClure et al. | |
| 2009/0326623 A1 | 12/2009 | Greenberg et al. | |
| 2010/0015095 A1 | 1/2010 | Pan et al. | |
| 2010/0016732 A1* | 1/2010 | Wells et al. | 600/476 |
| 2010/0135591 A1 | 6/2010 | Zador | |
| 2010/0152849 A1 | 6/2010 | Degenaar et al. | |
| 2010/0234273 A1 | 9/2010 | Boyden et al. | |
| 2010/0262212 A1 | 10/2010 | Shoham et al. | |
| 2010/0272688 A1 | 10/2010 | Acland et al. | |
| 2010/0286748 A1* | 11/2010 | Midani et al. | 607/48 |
| 2011/0213266 A1* | 9/2011 | Williams et al. | 600/545 |
| 2011/0270352 A1 | 11/2011 | Nanduri et al. | |
| 2011/0307079 A1* | 12/2011 | Oweiss et al. | 623/27 |
| 2012/0123293 A1* | 5/2012 | Shah et al. | 600/554 |

FOREIGN PATENT DOCUMENTS

| | | |
|---|---|---|
| CN | 101393789 A | 3/2009 |
| EP | 1 864 690 A2 | 12/2007 |
| EP | 1 891 976 A1 | 2/2008 |
| JP | 2009-540900 | 11/2009 |
| WO | WO-96/13598 | 5/1996 |
| WO | WO-98/48027 | 10/1998 |
| WO | WO-00/15822 | 3/2000 |
| WO | WO-01/94605 A2 | 12/2001 |
| WO | WO-03/047525 A2 | 6/2003 |
| WO | WO-03/080648 A2 | 10/2003 |
| WO | WO-03/093479 A1 | 11/2003 |
| WO | WO-03/104413 A2 | 12/2003 |
| WO | WO-2005/080573 A1 | 9/2005 |
| WO | WO-2007/127428 A2 | 11/2007 |
| WO | WO-2009/126112 | 10/2009 |
| WO | WO-2010/011404 A2 | 1/2010 |
| WO | WO-02/082904 A2 | 10/2012 |

OTHER PUBLICATIONS

International Search Report and Written Opinion of PCT/US2011/49188 dated Jan. 27, 2012.
Ahuja A. et al., "Blind Subjects Implanted with the Argus II Retinal Prosthesis Are Able to Improve Performance in a Spatial-Motor Task," British Journal of Ophthalmology (2010).
Arenkiel et al., "In Vivo Light-Induced Activation of Neural Circuitry in Transgenic Mice Expressing Channelrhodopsin-2," Neuron, 54(2):205-218 (2007).
Ausubel et al., Current Protocols in Molecular Biology, "Overview of the HIV-1 Lentivivral Vector System", John Wiley & Sons, New York, (1989), Unit 16.21, 15 pgs.
Ausubel et al., Current Protocols in Molecular Biology, "Production of Recombinant Adeno-Associated Viral Vectors for In Vitro and In Vivo Use", John Wiley & Sons, New York, (1989), Unit 16.25, 24 pgs.
Averback et al., Effects of Noise Correlations on Information Encoding and Decoding, J Neurophysiol, vol. 95, 2006, pp. 3633-3644.
Bach et al., "Visual Evoked Potential-Based Acuity Assessment in Normal Vision, Artificially Degraded Vision, and in Patients," British Journal of Ophthalmology, 92:396-403 (2008).
Ballard et al., Computer Vision, Prentice-Hall Inc New Jersey, 1982, (Table of Contents).
Barnstable et al., "Thy-1 Antigen: A Ganglion Cell Specific Marker in Rodent Retina," Neuroscience, 11(4):847-855 (1984).
Bi A, et al., "Ectopic Expression of a Microbial-Type Rhodopsin Restores Visual Responses in Mice with Photoreceptor Degeneration," Neuron, 50:23-33 (2006).
Bomash I, et al., "A Virtual Retina that Works on a Broad Array of Stimuli Including Natural Scenes: A Tool to Simplify the Problem of Population Coding," Society for Neuroscience, Program No. 891.5 (2010).
Bookstein et al., "Promoter Deletion and Loss of Retinoblastoma Gene Expression in Human Prostate Carcinoma," Proceedings of the National Academy Sciences, USA, 87(19):7762-7766 (1990).
Brown CJ et al., The Relationship Between EAP and EABR Thresholds and Levels Used to PRogram the Nucleus 24 Speech Processor: Data from Adults, Ear and Hearing, vol. 21, No. 2, 2000, pp. 151-163.
Busskamp et al., "Genetic Reactivation of Cone Photoreceptors Restores Visual Responses in Retinitis Pigmentosa," Science, 329:413-417 (2010).
Cai et al., "Gene Delivery to Mitotic and Postmitotic Photoreceptors Via Compacted DNA anoparticles Results in Improved Phenotype in a Mouse Model of Retinitis Pigmentosa," The FASEB Journal, 24:1178-1191 (2010).
Campagnola L, et al., "Fiber-Coupled Light-Omitting Diode for Localized Photostimulation of Neurons Expressing Channelrhodopsin-2," Journal of Neuroscience Methods, 169:27-33 (2008).
Cardin et al., "Targeted Optogenetic Stimulation and Recording of Neurons In Vivo Using Cell-Type-Specific Expression of Channelrhodopsin-2," Nature Protocols, 5(2):247-254 (2010).
Cescon C. et al., "Non-invasive characterization of single motor unit electromyographic and mechanomyographic activities in the biceps brachii muscle", J Electromyogr Kinesiol, vol. 16, No. 1, Epub Aug. 19, 2005, pp. 17-24.
Chader GJ, et al., "Artificial Vision: Needs, Functioning, and Testing of a Retinal Electronic Prosthesis", Progress in Brain Research, 175:317-332 (2009).
Chestek CA et al., "HermesC: Low-Power Wireless Neural Recording System for Freely Moving Primates" IEEE Transactions on Neural Systems and Rehabilitation Engineering, vol. 17, No. 4, 2009, pp. 268-275.
Chiappa, "Evoked Potentials in Clinical Medicine", Third Edition, Lippincott Raven (1997).
Chichilnisky, "A Simple White Noise Analysis of Neuronal Light Responses," Network 12(2):199-213 (2001).
Chopdar A, et al., "Age Related Macular Degeneration,"—Clincial Review—British Medical Journal, 326:485-488 (2003).
Communication pursuant to Rules 161(2) and 162 EPC in EP Appln No. 118223282.5 dated Apr. 12, 2013.
Dann JF, et al., "Retinal Ganglion Cells Projecting to the Accessory Optic System in the Rat," The Journal of Comparative Neurology, 262(1):141-158 (1987).
Dedek et al, "Ganglion Cell Adaptability: Does the Coupling of Horizontal Cells Play a Role?", Public Library of Science (Plos One), 3(3):E1714 (2008).
Douglas et al., "Independent Visual Threshold Measurements in the Two Eyes of Freely Moving Rats and Mice Using a Virtual-Reality Optokinetic System," Visual Neuroscience, 22(5):677-684 (2005).
Duda RO, et al., Multilayer Neural Networks, Pattern Classification (2nd Edition) Chapter 6, Wiley, NY (2001).
Eckmiller et al., Tunable Retina Encoders for Retina Implants: Why and How; Journal of Nueral Engineering, Institute of Physics Publishing, Bristol, GB, 2(1):s91-s104, Mar. 1, 2005.
Enroth-Cugell et al., "The Contrast Sensitivity of Retinal Ganglion Cells of the Cat," The Journal of Physiology, 187(3):517-552 (1966).
Extended European Search Report and Search Opinion for European Application No. 11748237.2, mailed Jul. 19, 2013.
Famulare M, Fairhall A., "Feature Selection in Simple Neurons: How Coding Depends on Spiking Dynamics," Neural Computation 22(3):581-598 (2010).

(56) References Cited

OTHER PUBLICATIONS

Field et al., "Information Processing in the Primate Retina: Circuitry and Coding," Annual Review of Neuroscience, 30:1-30 (2007).
Fitzgerald et al., "Retinal Signal Transmission in Duchenne Muscular Dystrophy," Journal of Clinical Investigation, 93:2425-2430 (1994).
Foley JM, et al., "Contrast Detection and Near-Threshold Discrimination in Human Vision," Vision Research, 21(7):1041-1053 (1981).
Franck KH., "A model of a nucleus 24 cochlear implant fitting protocol based on the electrically evoked whole nerve action potential", Ear & Hearing, vol. 23, No. 18, 2002, pp. 67S-71S.
Freund et al., "A Decision-Theoretic Generalization of On-Line Learning and an Application to Boosting," Journal of Computer and System Sciences, 55:119-139 (1997).
Friedman DS, et al., "Prevalence of Age-Related Macular Degeneration in the United States," Epidemiology, Eye Diseases Prevalence Research Group, Archives of Ophthalmology 122 (4):564-572 (Apr. 2004).
Geisler, "Visual Perception and the Statistical Properties of Natural Scenes," Annual Review of Psychology, 59:167-192 (2008).
Gerding H, et al., "Experimental Implantation of Epiretinal Retina Implants (EPI-RET) with an IOL-Type Receiver Unit," Journal Neural Engineering, 4:S38-S49 (2007).
Giolli RA, et al., "The Accessory Optic System: Basic Organization with an Update on Connectivity, Neurochemistry, and Function," Progress in Brain Research, 151:407-440 (2005).
Golan L, et al., "Design and Characteristics of Holographic Neural Photo-Stimulation Systems," Journal of Neural Engineering, 066004, vol. 6, (2009), pp. 1-14.
Graham-Rowe, "A Brighter Future for Retinal Implants," Technology Review, http://www.technologyreview.com/biomedicine/23539/, Boston, MA: MIT (2009).
Greenberg et al., "Differential Targeting of Optical Neuromodulators to Ganglion Cell Soma and Dendrites Allows Dynamic Control of Center-Surround Antagonism," Neuron, 69:713-720 (2011).
Grossman N, et al., "Multi-Site Optical Excitation Using Chr2 and Micro-LED Array," Journal of Neural Engineering, 7(1):1-13 (2010).
Guiraud D. et al., "An implantable neuroprosthesis for standing and walking in paraplegia: 5-year patient follow-up", Journal of Neural Engineering, 2006, vol. 3, pp. 268-275.
Han et al., "Millisecond-Timescale Optical Control of Neural Dynamics in the Nonhuman Primate Brain," Neuron, 62:191-198 (Apr. 30, 2009).
Hand, "Discrimination and Classification," Wiley Series in Probability and Mathematical Statistics (1981).
Hochberg LR, et al., "Neuronal ensemble control of prosthetic devices by a human with tetraplegia", Nature, Jul. 13, 2006, vol. 442, pp. 164-171.
Huang et al., "An Optoelectronic Platform for Retinal Prosthesis," Biomedical Circuits and Systems Conference (BIOCAS 2006), IEEE, pp. 110-113, Nov. 29, 2006.
Huberman AD, et al., "Architecture and Activity-Mediated Refinement of Axonal Projections from a Mosaic of Genetically Identified Retinal Ganglion Cells," Neuron, 59(3):425-38 (2008).
Huberman AD, et al., "Genetic Identification of an On-Off Direction-Selective Retinal Ganglion Cell Subtype Reveals a Layer-Specific Subcortical Map of Posterior Motion," Neuron, 62(3):327-334 (2009).
International Preliminary Report on Patentability in PCT/US2011/049188 mailed Mar. 14, 2013.
Ivanova E, et al., "Evaluation of the Adeno-Associated Virus Mediated Long-Term Expression of Channelrhodopsin-2 in the Mouse Retina," Molecular Vision, 15:1680-1689 (2009).
Izhikevich, "Dynamical Systems in Neuroscience: The Geometry of Excitability and Bursting," MIT Press, Cambridge, MA (2007).
Izhikevich, "Hybrid Spiking Models," Review, Philosophical Transactions of Royal Society A, 368:5061-5070 (2010).
Jacobs et al., "Ruling Out and Ruling in Neural Codes," Proceedings of the National Academy of Sciences, vol. 106, No. 14:5936-5941 (Apr. 7, 2009).

Kass RE, et al., "Statistical Issues in the Analysis of Neuronal Data," Journal of Neurophysiology, 94(1):8-25 (2005).
Kawasaki et al., "Variability of the Relative Afferent Pupillary Defect," American Journal of Ophthalmology, 120:622-633 (1995).
Kay MA, et al., "Viral Vectors for Gene Therapy: The Art of Turning Infectious Agents Into Vehicles of Therapeutics," Nature Medicine, 7(1):33-40, Review (2001).
Kelly S, et al., "Realization of a 15-Channel, Hermetically-Encased Wireless Subretinal Prosthesis for the Blind," In, pp. 200-203 (2009).
Kibbel S, et al., "Design and Performance Ofan Improved Active Subretinal Chip," World Congress on Medical Physics and Biomedical Engineering, Sep. 7-12, 2009, Munich, Germany (Kim SI, Suh TS, Dassel O, Schlegel WC, Eds), pp. 192-195, Springer Berlin Heidelberg (2009).
Kim Rh et al., "Waterproof AllnGaP optoelectronics on stretchable substrates with applications in biomedicine and robotics", Nature Materials, 2010, vol. 9, pp. 929-937.
Koilkonda RD, et al., "Efficient Expression of Self-Complementary AAV in Ganglion Cells of the Ex Vivo Primate Retina," Molecular Vision, 15:2796-2802 (2009).
Kuffler, "Discharge Patterns and Functional Organization of Mammalian Retina," Journal of Neurophysiology, 6(1):37-68 (1953).
Lagali PS, et al., "Light-Activated Channels Targeted to ON Bipolar Cells Restore Visual Function in Retinal Degeneration," Nature Neuroscience, 11 (6):667-675 (Jun. 2008).
Lee et al., "Variability and Correlated Noise in the Discharge of Neurons in Motor and Parietal Areas of the Primate Cortex", The Journal of Neuroscience, Feb. 1, 1998, vol. 18, No. 3, pp. 1161-1170.
Lei L. et al., "Efficient transduction of spiral ganglion cells using adenovirus type 5 vector in the rat", Acta Oto-Laryngologica, 2010, vol. 130, pp. 810-814.
Lesica et al., "Adaptation to Stimulus Contrast and Correlations During Natural Visual Stimulation," Neuron, 55(3):479-491 (Aug. 2, 2007).
Lettvin et al., "What the Frog's Eye Tells the Frog's Brain," Proceedings of the Institute of Radio Engineers 47(11): 1940-1951 (1959); Reprinted from: "The Mind: Biological Approaches to its Functions", Editors: William Corning, et al. 1968, pp. 233-258.
Liao et al., "In Vivo Gene Delivery in the Retina Using Polyethylenimine," Biotechniques, 42 (3):285-288 (2007).
Liu Y. et al., "Promoter effects of adeno-associated viral vector for transgene expression in the cochlea in vivo", Experimental and Molecular Medicine, Apr. 2007, vol. 38, No. 2, pp. 170-175.
Loewenstein JI, et al., "Outer Retinal Degeneration: An Electronic Retinal Prosthesis as a Treatment Strategy," Archives of Ophthalmology, 122 (4):587-596 (2004).
Luebke AE et al., "Adenoviral and AAV-mediated gene transfer to the inner ear: role of serotype, promoter, and viral load on in vivo and in vitro infection efficiencies", Adv. Otorhinolaryngol.Basel, Karger, 2009, vol. 66, pp. 87-98.
Maguire et al., "Safety and Efficacy of Gene Transfer for Leber's Congenital Amaurosis," The New England Journal of Medicine, 358 (21):2240-2248 (May 22, 2008).
Mancuso et al., "Gene Therapy for Red-Green Colour Blindness in Adult Primates," Nature, 461:784-787 (Oct. 8, 2009).
Martin et al., "Gene Delivery to the Eye Using Adeno-Associated Viral Vectors," Methods, 28:267-275 (2002).
McGowan et al., "Characterization of the Mouse Aldose Reductase Gene and Promoter in a Lens Epithelial Cell Line," Molecular Vision, 4:2 (1998).
Mclaughlin SK, et al., "Adeno-Associated Virus General Transduction Vectors: Analysis of Proviral Structures," Journal of Virology, 62(6):1963-1973 (1988).
Meytlis M, et al., "Assessing the Importance of Correlated Firing Using Large Populations of Neurons," Society for Neuroscience, Program No. 165.3 (2009).
Meytlis, et al. "Determining the role of correlated firing in large populations of neurons using white noise and natural scene stimuli", Vision Research, 2012, vol. 70, pp. 44-53.
Morgans et al., "TRPM1 is Required for the Depolarizing Light Response in Retinal ON-Bipolar Cells," Proceedings of the National Academy Sciences, USA, 106(45):19174-19178 (2009).

(56) References Cited

OTHER PUBLICATIONS

Moritz CT et al., "Direct control of paralysed muscles by cortical neurons", Nature, Dec. 2008, vol. 456, vol. 456, pp. 639-643.
Nanduri, et al. "Retinal Prosthesis Phosphene Shape Analysis," 30th Annual International Conference of the IEEE Engineering in Medicine and Biology Society, pp. 1785-1788 (2008).
New Zealand IPO First Examination Report dated Sep. 20, 2013 for New Zealand patent application 608804.
Nirenberg et al., "Heterogeneous Response Dynamics in Retinal Ganglion Cells: The Interplay of Predictive Coding and Adaptation," Journal of Neurophysiology, 103(6):3184-3194 (2010).
Nirenberg et al., "Retinal Ganglion Cells Act Largely as Independent Encoders," Nature 411(6838):698-701 (Jun. 7, 2001).
Nirenberg S, et al, "Targeted Ablation of Diverse Cell Classes in the Nervous System In Vivo," The Journal of Neuroscience, 13(8):3238-3251 (1993).
Nirenberg S, et al., "Population Coding in the Retina," Current Opinion in Neurobiology, 8(4):488-493 (1998).
Nirenberg S, et al., "The Light Response of Retinal Ganglion Cells is Truncated by a Displaced Amacrine Circuit," Neuron, 18:637-650 (1997).
Nirenberg, "Photoablation of Cells Expressing Beta-Galactosidase," Methods in Molecular Biology, 135:475-480 (2000).
Norcia et al., "Measurement of Spatial Contrast Sensitivity with the Swept Contrast VEP," Vision Research, 29(5):627-637 (1989).
Norcia, AM et al. , "Spatial Frequency Sweep VEP: Visual Acuity During the First Year of Life," Vision Research, 25(10):1399-1408 (1985).
Novin et al., "Transforming of Images Information to the Implant Part of Retinal Prothesis, by Converting of Images to Bit Formats," Biomedical Engineering (ICBME), 2010 17th Iranian Conference of IEEE, pp. 1-4, Nov. 3, 2010.
Okuyama et al., "Binocular Infrared Optometer for Measuring Accommodation in Both Eyes Simultaneously in Natural-Viewing Conditions," Applied Optics, 32(22):4147(1993).
Pandarinath et al., "A Novel Mechanism for Switching a Neural System from One State to Another," Frontiers in Computational Neuroscience, 31(4):2 (2010), p. 1-18.
Pandarinath et al., "Symmetry Breakdown in the On and Off Pathways of the Retina at Night: Functional Implications," Journal of Neuroscience, 30(30):10006-10014 (Jul. 28, 2010).
Paninski, "Maximum Likelihood Estimation of Cascade Point-Process Neural Encoding Models," Network: Comput. Neural Syst., 15(4):243-262 (2004).
Paninski, et al. "Statistical models for neural encoding, decoding, and optimal stimulus design", Progress in Brain Research, vol. 165, 2007, pp. 493-507.
Panzeri et al., "Correcting for the Sampling Bias Problem in Spike Train Information Measures," Journal of Neurophysiology, 98(3):1064-1072, Review (2007).
Pelli DO, et al., "The Design of a New Letter Chart for Measuring Contrast Sensitivity," Clinical Vision Sciences, 2:187-199 (1988).
Perry VH et al., "Functional lamination in the ganglion cell layer of the macaque's retina", Neuroscience, vol. 25, No. 1, 1988, pp. 217-223.
Petersen-Jones et al., "AAV Retinal Transduction in a Large Animal Model Species: Comparison of a Self-Complementary AAV2/5 with a Single-Stranded AAV2/5 Vector," Molecular Vision, 15:1835-1842 (2009).
Petrs-Silva et al., "High-Efficiency Transduction of the Mouse Retina by Tyrosinemutant AAV Serotype Vectors," Molecular Therapy, 17(3):463-471 (2009).
Pillow, et al. "Spatio-Temporal Correlations and Visual Signalling in a Complete Neuronal Population," Nature 454(7207):995-999 (2008).
Prusky et al., "Rapid Quantification of Adult and Developing Mouse Spatial Vision Using a Virtual Optomotor System," Investigative Ophthalmology & Visual Science, 45(12):4611-4616 (2004).
Pun, Introduction to Optimization Practice, ISBN 471-70233-1 (1969).

Purpura K, et al. "Light Adaptation in the Primate Retina: Analysis of Changes in Gain and Dynamics of Monkey Retinal Ganglion Cells," Visual Neuroscience 4(1):75-93 (1990).
Rolls ET, et al., "Role of Low and High Spatial Frequencies in the Face Selective Responses of Neurons in the Cortex in the Superior Temporal Sulcus in the Monkey," Vision Research, 25(8):1021-1035 (1985).
Rubinstein JT et al., "How do cochlear prostheses work?", Current Opinion in Neurobiology, 1999, vol. 9, 1999, pp. 399-404.
Sauer "Functional Expression of the Ere-Lox Site-Specific Recombination System in the Yeast *Saccharomyces cerevisiae*," Molecular and Cellular Biology, 7(6):2087-2096 (1987).
Sellick PM et al., "Modulation of responses of spiral ganglion cells in the guinea pig cochlea by low frequency sound", Hearing Research, 1982, vol. 7, pp. 199-221.
Shapley RM, et al., "How the Contrast Gain Control Modifies the Frequency Responses of Cat Retinal Ganglion Cells," The Journal of Physiology, 318:161-179 (1981).
Sharpee et al., "On the Importance of Static Nonlinearity in Estimating Spatiotemporal Neural Filters with Natural Stimuli," Journal of Neurophysiology 99(5):2496-2509 (2008).
Sheridan, "Gene Therapy Finds Its Niche," Nature Biotechnology, 29(2):121-128 (2011).
Siegert S, et al., Genetic Address Book for Retinal Cell Types, Nature Neuroscience, 12 (9) :1197-1204 (2009).
Simoncelli et al., "Characterization of Neural Responses with Stochastic Stimuli," The Cognitive Neurosciences, 3rd edition, 327-338 (2004).
Simonelli et al., "Gene Therapy for Leber's Congenital Amaurosis is Safe and Effective Through 1.5 Years After Vector Administration," Molecular Therapy, 18(3):643-650 (2010).
Sinclair, Jr. et al., Selective Ablation of a Class of Amacrine Cells Alters Spatial Processing in the Retina, Journal of Neuroscience, 24(6):1459-1467 (2004).
Sjostrand et al., "Morphometric Study of the Displacement of Retinal Ganglion Cells Subserving Cones within the Human Fovea," Graefe's Archive Clinical Experimental Ophthalmology 237:1014-1023 (1999).
Soucy et al., "A Novel Signaling Pathway from Rod Photoreceptors to Ganglion Cells in Mammalian Retina", Neuron, 21:481-493 (1998).
Stone et al., "Response Properties of Ganglion Cells in the Isolated Mouse Retina," Visual Neuroscience 10(1):31-39 (1993).
Thyagarajan S, et al., Visual Function in Mice with Photoreceptor Degeneration and Transgenic Expression of Channelrhodopsin 2 in Ganglion Cells, The Journal of Neuroscience, 30 (26) :8745-8758 (2010).
Tomita H, et al., "Channelrhodopsin-2 Gene Transduced into Retinal Ganglion Cells Restores Functional Vision in Genetically Blind Rats", Experimental Eye Research 90:429-436 (2010).
Troy JB, et al., "Spatial Properties of the Cat X-Cell Receptive Field as a Function of Mean Light Level," Visual Neuroscience, 16(6):1089-1104 (1999).
Troy JB, et al., "Spatiotemporal Integration of Light by the Cat X-Cell Center Under Photopic and Scotopic Conditions," Visual Neuroscience, 22(4):493-500 (2005).
Turchinovich et al., "Non-Viral Sirna Delivery into the Mouse Retina In Vivo," Boston Medical Center (BMC) Ophthalmology, 10:25 (2010).
Ueda et al., "The mGluR6 5' Upstream Transgene Sequence Directs a Cell-Specific and Developmentally Regulated Expression in Retinal Rod and ON-Type Cone Bipolar Cells," The Journal of Neuroscience, 17(9):3014-3023 (1997).
van Adel et al., "Delivery of Ciliary Neurotrophic Factor Via Lentiviral-Mediated Transfer Protects Axotomized Retinal Ganglion Cells for an Extended Period of Time," Human Gene Therapy, 14:103-115 (2003).
Victor JD, et al., "The Nonlinear Pathway of Y Ganglion Cells in the Cat Retina", Journal of Genetic Physiology, 74(6):671-689 (1979).
Victor, "The Dynamics of the Cat Retinal X Cell Centre," The Journal of Physiology, 386(1):219-246 (1987).

(56) References Cited

OTHER PUBLICATIONS

Volgyi B, et al., "Convergence and Segregation of the Multiple Rod Pathways in Mammalian Retina," The Journal of Neuroscience, 24(49):11182-11192 (2004).
Walther W, et al., Viral Vectors for Gene Transfer: A Review of their Use in the Treatment of Human Diseases, Drugs, 60(2):249-271, Review (2000).
Wang H. et al., "Efficient cochlear gene transfection in guinea-pigs with adeno-associated viral vectors by partial digestion of round window membrane", Gene Therapy, 2012, vol. 19, pp. 255-263.
Wassle, "Parallel Processing in the Mammalian Retina," National Review of Neuroscience Journal, 5(10):747-757 (2004).
Wells et al., "Optical Stimulation of Neural Tissue In Vivo," Optics Letters 30(5):504-506 (2005).
Winter JO et al., "Retinal Prostheses: Current Challenges and Future Outlook," Journal of Biomaterials Science Polymer Edn, 18(8):1031-1055 (2007).
Wright, "Gene Therapy for the Eye," British Journal of Ophthalmology, 81(8):620-622, Review (1997).
Yonehara K, et al., "Identification of Retinal Ganglion Cells and Their Projections Involved in Central Transmission of Information About Upward and Downward Image Motion," Public Library of Science (Plos ONE), 4(1):E4320 (2009).
Yonehara K, et al., "Expression of SPIG1 Reveals Development of a Retinal Ganglion Cell Subtype Projecting to the Medial Terminal Nucleus in the Mouse," Public Library of Science (Plos ONE), 3(2):E1533 (2008).
Zeng, et al. "Cochlear Damage Changes the Distribution of Vesicular Glutamate Transporters Associated with Auditory and Nonauditory Inputs to the Cochlear Nucleus", The Journal of Neuroscience, Apr. 1, 2009 vol. 29, No. 13, pp. 4210-4217.
Zhang Y, et al., "Ectopic Expression of Multiple Microbial Rhodopsins Restores On and Off Light Responses in Retinas with Photoreceptor Degeneration," The Journal of Neuroscience, 29(29):9186-9196 (2009).
Zierhofer CM et al., "Electronic Design of a Cochlear Implant for Multichannel High-Rate Pulsatile Stimulation Strategies", IEEE, Transactions on Rehabilitation Engineering, Mar. 1995, vol. 3, No. 1, pp. 112-116.
Zou et al., "Extraocular Image Processing for Retinal Prothesis Based on DSP," Nano/Micro Engineered and Molecular Systems (NEMS 2009), 4th IEEE International Conference on IEEE, pp. 563-566, Jan. 5, 2009.
Zrenner et al., "Subretinal Microelectrode Arrays Allow Blind Retinitis Pigmentosa Patients to Recognize Letters and Combine them to Words," Biomedical Engineering and Informatics (BMEI) '09. 2nd International Conference on Biomedical Engineering and Informatics, ISBN: 978-1-4244-4134-1. pp. 1 013 4 (2009).
Eckmiller, R. et al., "Dialog Concepts for Learning Retina Encoders," IEEE International Conference on Neural Networks Proceedings, (Jun. 1, 1997), vol. 4, pp. 2315-2320.
Examination Report received in European Patent Application 11748237.2 issued Sep. 3, 2014, 5 pages.
Examination Report received in European Patent Application No. 11748237.2 dated Apr. 16, 2014, 6 pages.
Extended Search Report received in European Patent Application No. 11822382 dated Feb. 17, 2014, 8 pages.
First Office Action from Chinese Application No. 201180021117.2 dated May 6, 2014, 15 pages—with English translation.
Non-Final Office Action received in U.S. Appl. No. 13/821,187 mailed Jul. 30, 2014, 20 pages.
First Office Action received in Chinese Patent Application No. 201180051504.0 issued Oct. 10, 2014, first received Nov. 25, 2014, 16 pages with English translation.
Office Action received in Japanese Patent Application No. 2012-555211 mailed Nov. 5, 2014, 8 pages—with English translation.
Examination Report received in European Patent Application No. 11822382.5 mailed Oct. 27, 2014, 6 pages.
Notice of Allowance received for U.S. Appl. No. 13/595,812 mailed Aug. 13, 2015, 37 pages.
Third Office Action received in Chinese Patent Application No. 201180021117.2 mailed Aug. 3, 2015, 8 pages with English translation.
Douglas, R.M. et al., "Independent visual threshold measurements in the two eyes of freely moving rats and mice using a virtual-reality optokinetic system," Vis Neurosci., (2005), vol. 22, pp. 677-684.
First Examination Report received in Australian Patent Application No. 2011220367 issued Jul. 13, 2015, 5 pages.
Notice of Allowance received in U.S. Appl. No. 13/821,187 issued Jul. 8, 2015, 23 pages.
Paninski, L. et al., "Statistical models for neural encoding, decoding, and optimal stimulus design," Prog Brain Res. (2007) 165:493-507.

* cited by examiner

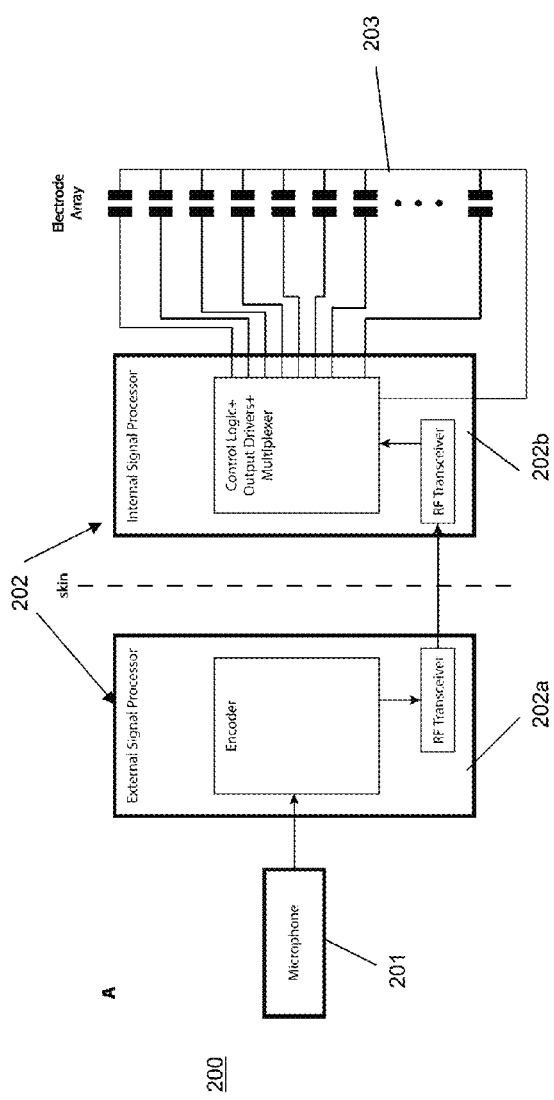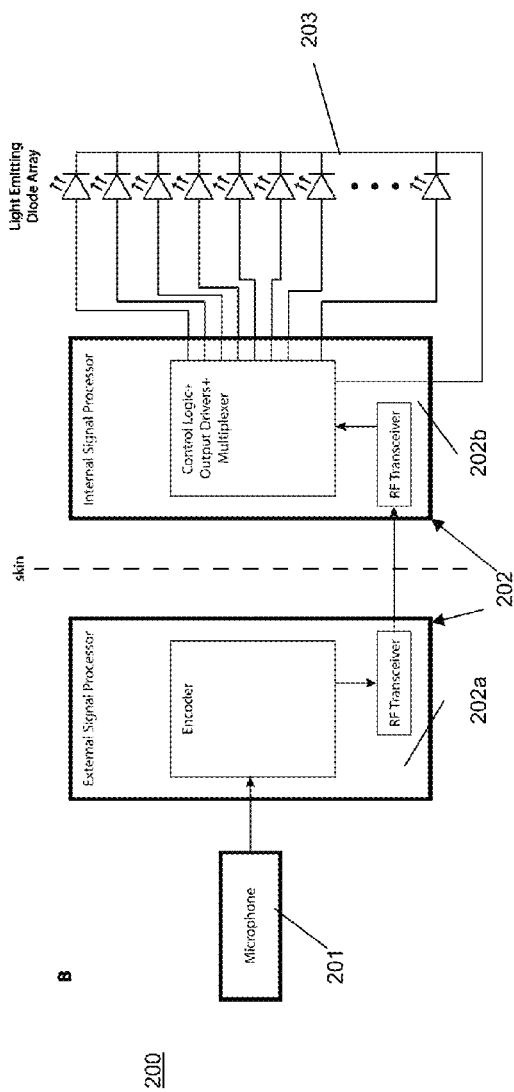

NEUROLOGICAL PROSTHESIS

CROSS REFERENCE TO RELATED APPLICATION

This application claims the benefit under 35 U.S.C. §119 (e) of U.S. Provisional Application No. 61/381,646 (filed on Sep. 10, 2010). The subject matter of this application is also related to U.S. Provisional Application Nos. 61/378,793 (filed on Aug. 31, 2010), 61/308,681 (filed on Feb. 26, 2010), 61/359,188 (filed on Jun. 28, 2010), 61/378,793 (filed on Aug. 31, 2010), and 61/382,280 (filed on Sep. 13, 2010), and International Patent Application Nos. PCT/US2011/26526 (filed Feb. 28, 2011) and PCT/US2011/026525 (filed Feb. 28, 2011). The contents of each of the forgoing applications are incorporated by reference in their entirety.

STATEMENT REGARDING FEDERALLY SPONSORED RESEARCH OR DEVELOPMENT

This invention was made with U.S. Government support under R01 EY12978 from National Institute of Health (NIH). The U.S. Government has certain rights in the invention.

FIELD

The present invention relates to methods and devices for restoring or improving function, such as nerve function, in a subject. In particular, the present invention relates to methods and devices for restoring or improving motor, auditory, or other function using a set of encoders that closely mimic the input/output transformation of nerve cells to produce near-normal, normal or even super-normal function in a subject.

BACKGROUND

A number of neurological disorders including, e.g., motor neuron disorders (e.g., damage from stroke, injury, diseases such as ALS and MS), psychiatric disorders, memory disorders, and auditory disorders involve thempairment of a set of nerve cells. In many cases, the malfunction of these cells prevents or degrades communication between healthy sets of cells.

Various neural prosthetics have been developed to bypass malfunctioning cells to restore communication between the healthy cells. However, in typical cases, the bypassed impaired cells do not simply operate as signal pass-throughs, but instead provide processing of signals. In cases where a neural prosthetic does not accurately mimic the processing of the bypassed cells, the subject will exhibit degraded function in comparison to an unimpaired subject.

Thus, there exists a need to develop a neural prosthesis that bypasses or "jumps" impaired signaling cells, while providing a close proxy of the processing of the bypassed impaired signaling cells (i.e., such that the input to output transfer function of the prosthesis is well matched to that which would have been exhibited by the bypassed signaling cells in an unimpaired subject).

SUMMARY

As described in PCT/US2011/026525 (filed Feb. 28, 2011) (henceforth the "Retinal Application"), the applicants have developed a method and device for restoring or improving vision, increasing visual acuity, or treating blindness or visual impairment, or activating retinal cells. The method includes capturing a stimulus, encoding the stimulus, transforming the code into transducer instructions at an interface, and transducing the instructions to retinal cells. The device includes a way to capture a stimulus, a processing device executing a set of encoders, an interface, and a set of transducers, where each transducer targets a single cell or a small number of cells; the set of transducers is referred to as a high resolution transducer. In one embodiment, each encoder executes a preprocessing step, a spatiotemporal transforming step as well as an output-generating step. The method can be used for a retinal prosthesis to generate representations for a broad range of stimuli, including artificial and natural stimuli.

The stimulus is converted or transformed into a proxy of normal retinal output, that is, a form of output the brain can readily interpret and make use of as a representation of an image. The conversion occurs on about the same time scale as that carried out by the normal or near-normal retina, i.e., the initial retinal ganglion cell response to a stimulus occurs in a time interval ranging from about 5-300 ms. The methods and devices described in the Retinal Application can help restore near-normal to normal vision, or can improve vision, including both grayscale vision and color vision, in a patient or affected mammal with any type of retinal degenerative disease where retinal ganglion cells (which may also be referred to herein as "ganglion cells") remain intact.

The retina prosthesis, like the normal retina, is an image processor—it extracts essential information from the stimuli it receives, and reformats the information into patterns of action potentials the brain can understand. The patterns of action potentials produced by the normal retinal are in what is referred to as the retina's code or the ganglion cell's code. The retina prosthesis converts visual stimuli into this same code, or a close proxy of it, so that the damaged or degenerated retina can produce normal or near-normal output. Because the retina prosthesis uses the same code as the normal retina or a close proxy of it, the firing patterns of the ganglion cells in the damaged or degenerated retina, that is, their patterns of action potentials are the same, or substantially similar, to those produced by normal ganglion cells. A subject treated with such devices will have visual recognition ability closely matching the ability of a normal or near-normal subject.

The applicants have realized that this approach may be applied more generally to provide methods and devices for restoring or improving function, such as neurological, motor, or auditory function in a human patient or other mammalian subject. As in the retinal case, a device including a processor which implements a set of encoders is provided which receives an input signal and generates an output signal, such that the input/output transformation operates as a close proxy of the signal processing that would occur in a normal patient.

In some embodiments, the input signal comes from a first set of healthy cells (e.g., supplementary motor area neurons), and the output signal drives a response in second set of healthy cells (e.g., spinal motor neurons) that are separated from the first set by an impaired set of signaling cells (e.g., damaged primary motor cortex neurons). The encoders provide a close proxy of the processing that would occur in the set of signaling cells in an unimpaired subject, allowing the impaired cells to be bypassed or jumped while reducing or eliminating degradation in function.

In some embodiments, the input signal is an external stimulus (e.g., sound waves), which are detected by the device (e.g., using a microphone). The input signal is processed using a set of encoders to generate a coded output used to drive healthy cells (e.g., spiral ganglion cells in the inner ear) which are associated with an impaired set of signaling cells (e.g., cochlear hair cells used to detect sound in the inner ear). The encoders provide a close proxy of the processing that would occur in the set of signaling cells in an unimpaired subject, allowing the impaired cells to be bypassed or jumped over, reducing or eliminating degradation in function.

To ensure that the encoders provide a close proxy of the processing that would occur in the signaling cells of a normal subject, a strategy may be employed of using experimental data (e.g., collected in vivo or in vitro from unimpaired cells) to generate a model of the signaling cells' processing. Accordingly, a data-driven phenomenological model is provided, directly analogous to those developed to model retinal processing in the Retinal Application.

Because this approach leverages experimental data, the generated encoders can accurately simulate the signaling cell processing, without requiring a detailed abstract understanding of the signaling cells' underlying processing schemes. For example, it is believed that retinal processing in primates and humans highlights features in the visual stimulus useful for pattern recognition tasks (e.g., facial recognition) while de-emphasizing or eliminating other features (e.g., redundant information or noise) to allow for efficient processing in the brain. Similar processing occurs in many other types of cells or neural networks (e.g., spinal motor neurons or motor neuron networks or spiral ganglion cells in the ear, etc.). As of yet, there is no complete abstract understanding of the details of these natural processing schemes, which developed as the result natural selection over the course of eons. However, despite this lack of abstract understanding, the devices and techniques described herein can capture the benefit of this processing, by accurately mimicking the response of unimpaired cells A method improving or restoring neural function in a mammalian subject in need thereof is disclosed, the method including: using an input receiver to record an input signal generated by a first set of nerve cells; using an a encoder unit including a set of encoders to generate a set of coded outputs in response to the input signal; using the encoded outputs to drive an output generator; and using an output generator to activate a second set of nerve cells where the second set of nerve cells is separated from the first set of nerve cells by impaired set of signaling cells; where the second set of nerve cells produces a response that is substantially the same as the response in an unimpaired subject.

In some embodiments, the first set of nerve cells includes supplementary motor area neurons; the second set of nerve cells includes spinal motor neurons; and the impaired set of signaling cells includes primary motor cortex neurons.

Some embodiments include generating the input signal as a time resolved series of values $\vec{a}$ corresponding to the pattern of neural activity generated in the first set of nerve cells; and transforming the values $\vec{a}$ to a time resolved series of output values $\vec{c}$ by applying a transformation.

In some embodiments, $\vec{c}$ is a vector valued function, where each element of the vector is a value corresponding to a firing rate of a single cell or small group of cells from the second set of nerve cells.

In some embodiments, $\vec{c}$ is a vector valued function, where each element of the vector is a value corresponding to the total firing rate of second set of nerve cells.

In some embodiments, $\vec{c}$ is a vector valued function, where each element of the vector is a value corresponding to the total firing rate of a respective subpopulation of the second set of nerve cells.

In some embodiments, the second set of nerve cells includes motor neurons, and each subpopulation innervates a different respective muscle.

In some embodiments, the transformation includes: a set of spatiotemporal linear filters; and a nonlinear function.

In some embodiments, the transformation is characterized by a set of parameters; and where the set of parameters corresponds to a result of fitting the transformation to experimental data obtained by: exposing an unimpaired subject to a broad range of reference stimuli; recording a first response in the unimpaired subject corresponding to the first set of nerve cells; recording a second response in the unimpaired subject corresponding to the second set of nerve cells.

In some embodiments, the second response includes the firing rate of individual nerve cells.

In some embodiments, the spatiotemporal filters are parameterized by a set of K weights.

In some embodiments, the method of claim 11, where K is in the range of 1-100 or any subrange thereof, e.g., in the range of 5-20.

In some embodiments, the nonlinear function is parameterized as a cubic spline function with M knots.

In some embodiments, M is in the range of 1-100 or any subrange thereof, e.g., in the range of 2-20.

In some embodiments, the spatiotemporal linear filters operate over P time bins, each having a duration Q.

In some embodiments, P is in the range of 1-100, or any subrange thereof, e.g., in the range of 5-20.

In some embodiments, Q is in the range of 10 ms-100 ms. In some embodiments, Q is in the range of 1 ms-1000 ms or any subrange thereof.

In some embodiments, the broad range of reference stimuli includes at least one chosen from the list consisting of: motion in an environment including one or more obstacles; manipulation of objects having different weights; and moving a cursor to one of several locations on a display.

In some embodiments, the second set of nerve cells are light sensitized; and the step of using an output generator to activate a second set of nerve cells includes: generating a time resolved optical signal; and directing the optical signal to the second set of nerve cells to stimulate a response.

Some embodiments include sensitizing the second set of nerve cells to light

In some embodiments, the optical signal includes a spatially and temporally modulated pattern of light.

In some embodiments, the modulated pattern of light includes an array of pixels having an average pixel size of less than 0.1 mm and a pixel modulation rate of greater than 100 Hz.

In some embodiments, the step of using an output generator to activate a second set of nerve cells includes: generating a set of electrical pulses; and directing the electrical pulses the second set of nerve cells to stimulate a response.

In another aspect, a device improving or restoring neural function in a mammalian subject in need thereof is disclosed, the device including: an input receiver configured to record an input signal generated by a first set of nerve cells; an output generator configured to activate a second set of nerve cells, where the second set of nerve cells is separated from the first set of nerve cells by an impaired set of signaling cells; and an encoder unit including a set of encoders that generate a set of coded outputs in response to the input signal, where the set of coded outputs control the output generator to activate the second set of nerve cells to produce a response to the input signal that is substantially the same as the response in an unimpaired subject.

In some embodiments, the input receiver includes an electrode.

In some embodiments, the input receiver includes an array of electrodes.

In some embodiments, the array of electrodes records the response of at least 100 neurons in the first set of neurons.

In some embodiments, the encoder unit includes at least one processor.

In some embodiments, the at least one processor includes a digital signal processor.

In some embodiments, the at least one processor includes multiple processors configured to operate in parallel.

In some embodiments, the output generator includes a set of electrodes.

In some embodiments, the output generator includes an optical signal generator. In some embodiments, the optical signal generator includes a digital light processor.

In some embodiments, the optical signal generator includes an array of light emitting diodes.

In another aspect, a non-transitory computer readable media is disclosed having computer-executable instruction including instruction for executing steps including: recording an input signal generated by a first set of nerve cells; using an a encoder unit including a set of set of encoders to generate a set of coded outputs in response to the input signal, and using the coded outputs to control an output generator to activate a second set of nerve cells where the second set of nerve cells is separated from the first set of neurons by an impaired set of signaling cells; where the second set of nerve cells produces a response to the input signal that is substantially the same as the response in an unimpaired subject.

In another embodiments, a method of improving or restoring auditory function in a mammalian subject in need thereof, is disclosed the method including: using an audio receiver to generate an input signal in response to an audio stimulus; using an a encoder unit including a set of set of encoders to generate a set of coded outputs in response to the input signal; using the encoded outputs to drive an output generator; and using an output generator to activate a set of auditory neurons, where the set of auditory neurons are associated with a set of impaired signaling cells; where the auditory neurons produce a response that is substantially the same as the response to the stimuli in an unimpaired subject.

In some embodiments, the set of auditory neurons include spiral ganglion cells; and the impaired set of signaling cells includes cochlear hair cells.

Some embodiments include generating the input signal as a time resolved series of values $\vec{a}$ corresponding to the audio stimulus; transforming the values $\vec{a}$ to a time resolved series of output values $\vec{c}$ by applying a transformation.

In some embodiments, $\vec{c}$ is a vector valued function, where each element of the vector is a value corresponding the firing rate of a single spiral ganglion cell or small group of spiral ganglion cells from the set of auditory neurons.

In some embodiments, $\vec{c}$ is a vector valued function, where each element of the vector is a value corresponding to the total firing rate of a respective subpopulation of the auditory set of neurons.

In some embodiments, the transformation includes: a set of spatiotemporal linear filters; and a nonlinear function.

In some embodiments, the transformation is characterized by a set of parameters; and where the set of parameters corresponds to a result of fitting the transformation to experimental data obtained by: exposing an unimpaired subject to a broad range of reference audio stimuli; and recording a response in the unimpaired subject corresponding to the set of auditory neurons.

In some embodiments, the response includes the firing rate of individual neurons.

In some embodiments, the spatiotemporal filters are parameterized by a set of K weights.

In some embodiments, K is in the range of 1-100 or any subrange thereof, e.g., in the range of 5-20.

In some embodiments, the nonlinear function is parameterized as a cubic spline function with M knots.

In some embodiments, M is in the range of 1-100 or any subrange thereof, e.g., in the range of 2-20.

In some embodiments, the spatiotemporal linear filters operate over P time bins, each having a duration Q.

In some embodiments, P is in the range of 1-100 or any subrange thereof, e.g., in the range of 5-20.

In some embodiments, Q is in the range of 1 ms-1000 ms, or any subrange thereof, e.g., in the range of 10 ms-100 ms.

In some embodiments, the broad range of reference stimuli includes natural sound and white noise stimuli.

In some embodiments, the set of auditory neurons are light sensitized; and the step of using an output generator to activate the set of auditory neurons includes: generating a time resolved optical signal; and directing the optical signal to the second set of neurons to stimulate a response.

Some embodiments include sensitizing the second set of neurons to light

In some embodiments, the optical signal includes a spatially and temporally modulated pattern of light.

In some embodiments, the modulated pattern of light includes an array of pixels having an average pixel size of less than 0.1 mm and a pixel modulation rate of greater than 100 Hz.

In some embodiments, the step of using an output generator to activate the set of auditory neurons includes: generating a set of electrical pulses; and directing the electrical pulses to the set of auditory neurons to stimulate a response.

In another aspect, a device for improving or restoring auditory function in a mammalian subject in need thereof is disclosed, the device including: an audio receiver configured to generate an input signal in response to an audio stimulus; an encoder unit including a set of set of encoders configured to generate a set of coded outputs in response to the input signal; and an output generator configured to, in response to the set of coded outputs, activate a set of auditory neurons, where the set of auditory neurons are associated with a set of impaired signaling cells; where the second set of cells produces a response to a broad range of stimuli that is substantially the same as the response to the stimuli in an unimpaired subject.

In some embodiments, the input receiver includes an audio transducer configured to convert an audio signal to a digital signal.

In some embodiments, the encoder unit includes at least one processor.

In some embodiments, the at least one processor includes a digital signal processor.

In some embodiments, the at least one processor includes multiple processors configured to operate in parallel.

In some embodiments, the output generator includes a set of electrodes.

In some embodiments, the output generator includes an optical signal generator.

In some embodiments, the optical signal generator includes a light emitting diode array or a digital light processor.

In another aspect, a non-transitory computer readable media is disclosed having computer-executable instruction including instruction for executing steps including: generating an input signal in response to an audio stimulus; controlling an encoder unit including a set of set of encoders to generate a set of coded outputs in response to the input signal; and controlling an output generator to, in response to the set of coded outputs, activate a set of auditory neurons, where the set of auditory neurons are associated with a set of impaired signaling cells; where the set of coded outputs control the output generator to activate the set of auditory neurons to produce a response that is substantially the same as the response to the stimuli in an unimpaired subject.

Various embodiments may feature any of the elements, steps, devices, techniques, etc. described above, either alone or in any suitable combination.

The terms prosthetic, prosthesis, prosthetic device, and prosthesis device are used interchangeably herein.

BRIEF DESCRIPTION OF THE DRAWINGS

FIG. 10A is a schematic of an auditory prosthesis featuring multiple output electrodes.

FIG. 10B is a schematic of an auditory prosthesis featuring multiple output light emitting diodes (LEDs).

DETAILED DESCRIPTION

Figure 1B:
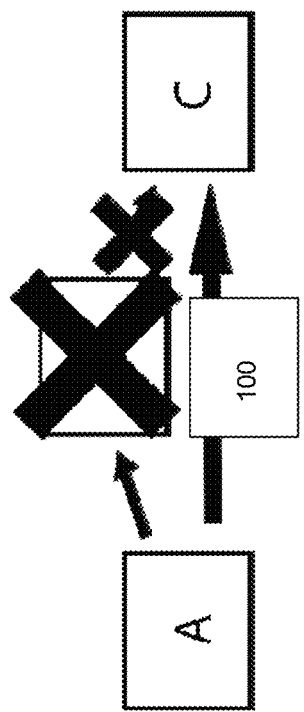
FIG. 1B is a schematic illustrating the use of a neural prosthesis to treat impairment in the neural system of FIG. 1A.
Figure 1A:
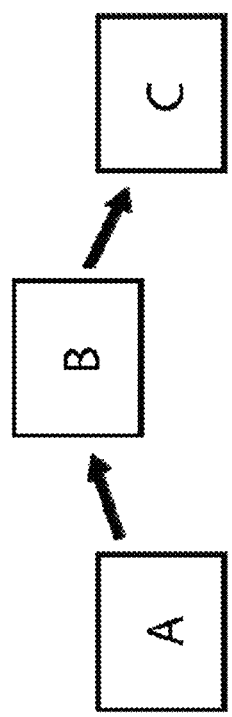
FIG. 1A is a schematic illustrating neural activity in a neural system, where signals from a set of cells labeled A are communicated through a set of cells labeled B to generate a response in a set of cells C.

FIGS. 1A and 1B illustrate the operation of a neural prosthetic 100. FIG. 1A, illustrates the function of an unimpaired subject. A first set of neurons (A) sends signals to another set of neurons (B) and they, in turn, send signals to a third set (C). FIG. 1B illustrates the function in an impaired subject, e.g., where the subject has suffered a stroke that damages set B. The neural prosthetic 100, bypasses or jumps (the terms are used interchangeably herein) the impaired nerves of set B.

Using experimentally derived information about the transformation implemented by the unimpaired set B in communicating signals from set A to C, one can build the device 100 such that it mimics the transformation. That is, the device 100 can produce a response in set C (e.g., a neural or nerve firing pattern) that closely mimics that which would normally occur when A sends out its signals to set C through an unimpaired set B. C can then send on normal signals to its downstream neurons, and the patient can regain normal functioning. The encoder essentially jumps over B. (If the transformation is well modeled based on experimental data, then this can be done for arbitrary signals from A). To drive the neurons in C, several techniques are possible such as driving optogenetic transducers (e.g., channelrhodopsin-2 or one of its derivatives) or electrode based stimulation, as described in greater detail below.

In some embodiments, the signal from set A may be replaced by an external stimulus. This was the case in the Retinal Application, where set B corresponded to damaged retinal cells (e.g., photoreceptors), set C corresponded to retinal ganglion cells, and the prosthesis 100 received a visual stimulus (e.g., using a camera), processed the stimulus with encoders in a way that mimicked the processing of the damaged retinal cells and circuitry (which would be analogous to B in FIG. 1B) and used a high resolution transducer to drive the retinal ganglion cells to produce a response that closely matched that produced in an unimpaired subject. A similar approach may be used for restoring or improving auditory function, as detailed below.

As noted above, in some embodiments, a data-based phenomenological approach is used in building the encoders for the prosthetic 100: In typical cases, to build the encoder, one needs to finds the transformation between the outside world (e.g., an external visual or audio stimulus) and a set of neurons or between two sets of neurons. Below are three examples.

In the case of the prosthetic device for the retina, described in the Retinal Application, the encoder mimics the transformation between visual stimuli (the outside world) and the retina's output cells—that is, it jumps over the damaged sensory cells in the retina (the photoreceptors) and interacts directly with the healthy cells (e.g., ganglion cells), the retina's output cells, so that normal signals can be sent to the brain.

In the case of an auditory prosthetic, the encoder mimics the transformation between auditory stimuli (the outside world) and the cells in the auditory nerve—that is, it bypasses the damaged sensory cells (the hair cells of the inner ear) and interacts directly with the auditory nerve cells, the spiral ganglion cells, so normal sound information can be sent to the brain.

In the case of a motor prosthetic (the specific embodiment given below), the encoder mimics the transformation between Supplementary Motor Area (SMA) and spinal motor neurons (SMN)—that is, it jumps over the damaged primary motor cortex (a area commonly damaged by strokes) and interacts directly with the healthy cells, the SMN (or the muscles they synapse on), so that normal muscle contractions/relaxations can be made.

This approach may be extended to a wide variety of other applications. A non limiting list of such applications is provided in Tables 2-6 found toward the end of this document.

To generate the data based model, the transformations performed by the encoders are worked out a priori (e.g., in an animal model or, using human patients, i.e., using electrode implants and electromyography (EMG)). It's worked out by causing a large variety of patterns of activity to occur in the system and recording from the healthy neurons.

For example, to develop the encoder for the visual prosthetic, recordings were made from retina's output neurons, the ganglion cells, while the retina was presented with a wide variety of stimuli: this allowed us to determine the transformation from visual stimuli to retinal ganglion cell firing spike patterns.

Likewise, in the case of the auditory prosthetic, recordings are made in the spiral ganglion cells in the presence of a wide variety of auditory stimuli (e.g., including white noise and natural noise), so the transformation between sound stimuli and the spiral ganglion cell spike patterns can be determined.

In the case of the motor prosthetic, one may use two sets of recordings: one from neurons in the SMA and one from the spinal motor neurons that correspond to them (e.g. to generate a set of encoders useful for arm prosthetics, one may record from SMA neurons that affect arm movements and from spinal motor neurons that control arm muscles), so one can obtain the transformation between the two sets of neurons (in this case, in FIG. 1B, set A would correspond to the SMA neurons that affect arm movements, and set C would correspond to the spinal motor neurons that control arm muscles).

In each of these example and other cases, visual, auditory, motor, or other, the approach is phenomenological: One parameterizes the relationship between the external stimuli and a set of neural signals or between two sets of neural signals, and one finds the parameter values using an optimization procedure, such as maximum likelihood.

In many applications, an advantage of this approach is that it has the capacity to generalize, that is, to mimic the processing of the impaired cells across a broad range of activity, because the approach uses a mathematical transformation to capture the relation between the outside world and a set of neurons or between two sets of neurons, rather than, for example, a look up table. As indicated schematically in FIG. 1B, the prosthesis 100 is designed to take activity patterns of arbitrary complexity in set A and produce the outputs that normally occur in set C as a result—that is, for most or all patterns that occur in A, the method will be able to make C produce its normal output (e.g., nerve firing patterns). This is advantageous because normal brain activity is complex and variable and cannot be accurately characterized into a small number of categories, as would be necessary for the more standard look up table approach.

Note, in some examples presented herein the prosthesis device is described as jumping or bypassing impaired cells. It is to be understood that in typical embodiments, the prosthetic does not simply reproduce the processing of specific impaired cells, but provides an accurate proxy of the input/output transformation that occurs in a normal subject which converts a given input stimulus or neural activity at A into an output at C. That is, the prosthetic not only mimics the behavior of a subset of impaired cells in B, but instead acts as a proxy for the entire signally chain (potentially including both healthy and/or impaired cells with various interactions) from A to C.

Motor Prosthesis

In one embodiment, the prosthesis 100 is employed to restore motor function in an impaired subject. Restoration of motor system function as is important for a number of reasons, including: a) damage to the motor system is the major source of disability in stroke and other neurological disease (e.g., MS, primary lateral sclerosis (a form of ALS), cancers of the nervous system), b) major features of the motor system's anatomy map on to the A to B to C scheme described above in reference to FIGS. 1A and 1B, and c) the motor system is readily accessible to the required studies in animals and for implants in humans. Thus, using the techniques described herein building a set of encoders for applications is straightforward, and the return on the effort is large—it can provide a remedy for a very broad range of disorders—that is, motor damage due to many different underlying causes can all be treated with the same set of encoders.

Normally, during voluntary movement, signals are transmitted from the Supplementary Motor Area (SMA) to Primary Motor Cortex (PMC) to Spinal Motor Neurons (SMN) to Muscle (M). The SMA corresponds to A in FIGS. 1A and 1B, the PMC and its descending fibers correspond to B, and the SMN (and their axons) correspond to C. In some embodiments, the SMN can be jumped also (i.e., included as part of B), and stimulation can go directly to muscle, which would then correspond to C.

In some cases, B is a particularly vulnerable part of the motor system because the pathway from PMC to the SMN is long—that is, the cell bodies of the neurons lie in the cortex, but their axons descend through the thalamus, brain stem, and spinal cord. Thus strokes or other damage to any area along the pathway will interrupt their signals and cause motor deficits or outright paralysis.

Figure 2:
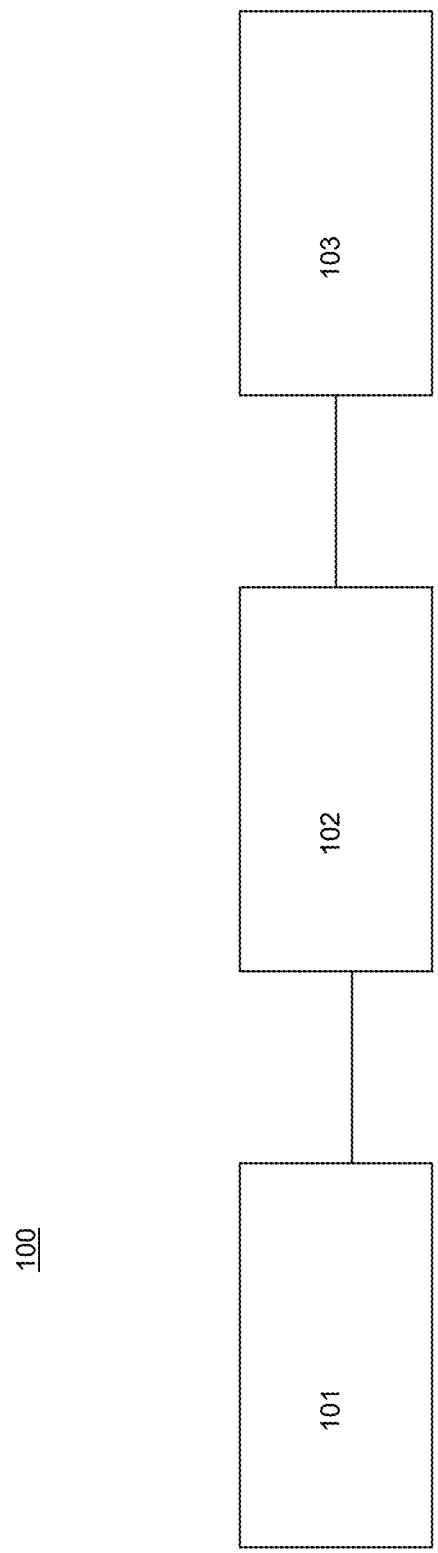
FIG. 2 is a block diagram of a neural prosthesis.

Referring to FIG. 2, in some embodiments, the prosthesis 100 is a device that carries out the transformation of signals from A to C that is normally carried out by interactions from A to B to C. The prosthesis 100 includes an input receiver 101 (e.g., one or more electrodes) which record an input signal generated by set of neurons in A (e.g., in response to a decision by the patient to make a movement, a motor command). A processor 102 (sometimes referred to herein as an encoder unit) processes the input signal using a set of encoders to generate a set of coded outputs. An output generator 103 (e.g. an electrode or optical device of the types described herein), in response to the coded outputs, activates the second set of neurons (neurons in C) to produce a response to the input signal, e.g., a response that is substantially the same as the response in an unimpaired subject.

In some embodiments, an encoder implemented by the prosthesis 100 operates using a model for the transformation, $\vec{c} = \vec{f}(\vec{a})$, where $\vec{a}$ is the pattern of neural activity (expressed here as a n firing rate as a function of time) in region A, and $\vec{c}$ is the pattern of neural activity in region C. Both $\vec{a}$ and $\vec{c}$ are multivariate (they represent the activity of a population of neurons), so we represent them here as vector-valued functions of time. (Note that it's not critical to understand B at a mechanistic level, just to capture its input/output relation, as in the retinal prosthetic approach described in the Retinal Application.)

Some embodiments employ a strategy adapted from those found to be effective in the retina—that is, we choose the following parametric form, and we determine the parameters of the form by optimizing a cost function separately for each output neuron (or small groups of output neurons, e.g., containing less than 2, less than 3, less than 5, less than 10, less than 20, less than 30, less than 50, or less than 100 neurons, e.g., in the range of 1-1000 neurons or any subrange thereof).

For example, for each output neuron, $c_i$, we determine weight functions, $\vec{w}_i$, and a nonlinearity, $N_i$, so that the modeled transformation $$c_i^{fit} = N_i(\vec{a} \cdot \vec{w}) \quad (1)$$

is an optimal match to the actual transformation, $c_i = f_i(\vec{a})$, measured experimentally using the techniques described herein. $N_i$ is a pointwise nonlinearity, i.e., a function $y = N_i(x)$, where x and y are both real-valued quantities (in the case of the retinal encoders, $N_i$ was a cubic spline with 7 knots, but any other suitable number may be used), and $\vec{w}$ is a vector of weights, specific to the output neuron i. $\vec{w}_i$ consists of an array of quantities $w_{i,j}(t)$, where i labels a neuron in the population C, j labels a neuron in the population A, and t is time. The ith component of the dot product $\vec{a}$ is calculated as follows:

$$\Sigma_{j,i} a_j(t) w_{i,j}(t)$$

As was the case for the encoders for the retina, the optimization is performed to maximize the expected log likelihood over the entire output population, namely, $$L = \left\langle \sum_i ll(c_i^{fit}, \vec{a}) \right\rangle$$

$ll(c_i^{fit}, \vec{a})$ denotes the log likelihood that $c_i^{fit}$ accounts for the observed activity of the ith neuron in C, when $\vec{a}$ is the pattern of neural activity in region A, and the brackets denote an average over all patterns of activity produced in A. This likelihood is calculated from Poisson statistics based on the model firing rates (i.e., $c_i^{fit}$).

The parametric form in eq. 1 builds on what we used for the retinal transformation: the weights $\vec{w}_i$, i.e., the arrays $w_{i,j}(t)$ correspond to a set of spatiotemporal linear filters, because the subscripts i and j correspond to the positions of the neurons in C and A, respectively, and $N_i$ is an adjustable nonlinearity.

This overall strategy has several advantages—the linear-nonlinear cascade (LNC) can be used as a universal building block for any transformation (Cybenko, 1989), it is a reasonable caricature of the input/output transformation carried out by single neurons (or small groups of neurons), and there are optimization techniques that work well with complex, natural inputs, such as are present in area A. In the retina, the inputs were white noise and complex natural scenes. In the motor case, the inputs are the activity patterns that occur in A under freely-moving behavior.

Constructing Encoders from Experimental Motor Activity Data

In some embodiments, the encoders implemented by the processor 102 are constructed from data collected in two locations: the SMA and the targeted muscles. Briefly, e.g., one may implant an array of extracellular electrodes in SMA (e.g., as described in Hochberg et al, 2006). This allows one to obtain firing patterns from one or more SMA neurons (e.g. in the range of 1-10,000 neurons, or any subrange thereof). At the same time, one may apply surface electrodes to the targeted muscles to obtain electromyography signals (EMGs), as mentioned above (see, e.g., Cescon et al, 2006), as this allows us to obtain the array of activity patterns, $c_i$.

Note, in various embodiments, one can use the EMG from each muscle to determine the activity pattern in at least two ways: the EMG can be processed to count spikes (to obtain a total firing rate), or it can be rectified and low pass filtered. In many applications, the first approach is the simplest and corresponds directly to the population firing rate, but there are practical advantages to using the second. Specifically, the rectified, low pass filtered signal will be dominated by the larger motor units in the population, and since larger motor unit produce more force by the muscle, this low pass filtered signal correlates more closely with the force command, and, therefore, is considered the more relevant quantity when aiming to control force.

Note that for a given $c_i$, some SMA neurons may not be relevant for its control, and the model described herein accounts for this (the weights of these neurons will be zero or negligible). This is analogous to the situation with ganglion cells in the retina, where some regions of an image (some pixels) are not relevant for a given ganglion cell's control, and these pixels are given negligible weights.

To generate generalizable encoders, one adapt the strategy as was used for generating the retinal encoders: one may provoke the system with a broad range of stimuli. In the case of the retinal encoders, we presented the retinas from normal subjects with two classes of stimuli-artificial (white noise) and natural scenes—and recorded ganglion cell responses. We then modeled the transformation from stimulus to response. The "training" stimuli (the white noise and natural scenes) were broad enough to produce a general model, one that was effective on any stimulus. In other words, given the training stimuli, we obtained a model that faithfully reproduced ganglion cell responses to essentially any stimuli (stimuli of arbitrary complexity).

In the case of the motor system, one may adapt the same approach. The normal subject (e.g., a human, a non-human primate, a mouse, etc.) carries out a variety of artificial and natural movements, such as walking on a wide variety of different and irregular terrains and grades, and manipulating objects of different masses, and we record responses from SMA and from the muscles (e.g., using the surface electrode EMG recordings). The irregular terrains and unpredictable loads are an example of a motor equivalent of white noise, and the movements on naturally changing terrain with predictable loads are an example of a motor equivalent of natural scenes. In typical applications, the two together are the key elements for obtaining generalizable encoders. In various embodiments, other suitable activities may be used.

Using the experimental the data sets generated in the previous step, one may model the transformation between SMA recordings and EMG recordings using eq. 1. This gives a set of encoders, e.g., one for each muscle.

An alternative strategy to the one described above is to treat $c_i$ as the total firing rate of a subpopulation of neurons, rather than a single neuron. This makes sense in the case of muscle activation because each muscle is activated by a subpopulation of neurons, rather than a single neuron, and the relevant variable for the subpopulation is total firing rate (at each moment in time). This firing rate can be obtained from the branch of the peripheral nerve that innervates the muscle. Experimentally, the firing rate can be measured noninvasively using surface electrodes that are placed on the skin over the muscle; the surface electrodes record an electromyography signal (EMG), from which the firing rate of the branch can be measured. (The EMG basically a surrogate for the total firing rate in the peripheral nerve branch that innervates the muscle.)

In this alternate strategy, each subpopulation $c_i$ corresponds to the population that innervates a different muscle. Thus, the transformation modeled is the transformation from the activity is SMA to $\vec{c}$, the pattern of activity in the array of subpopulations.

Note that despite the apparent challenges of providing a transformation that can cover the jump from supplementary motor area to spinal motor neurons (or muscle), experimental results obtained in the case of retinal prosthetic techniques indicate that these challenges can be readily overcome with the techniques described herein. In the case of the retinal prosthesis, the transformation jumped at least two synapses and captured the output almost exactly (for both mouse and primate subjects), as shown in the Retinal Application. Specifically, the transformation was from image to ganglion cell output which required jumping all the operations from photoreceptors to bipolar cells to ganglion cells, including the lateral actions of the horizontal cells and the many types of amacrine cells. The jump in the motor system would be, e.g., Supplementary Motor Layer 5→Motor Layer 4→Motor Layer 2/3→Motor Layer 5→spinal motoneuron or muscle. A second related point is that the approach might appear to be challenging due to the apparent high dimensionality in the motor context—that is, the motor cortex is signaling activity for movements related to many extremities—e.g., for the legs, it's covering the hips, knees, ankles, feet, toes, etc. But the dimensionality is not as high as it seems because we treat the cells as independent, a reasonable approximation as shown by Lee et al., 1998, Variability and Correlated Noise in the Discharge of Neurons in Motor and Parietal Areas of the Primate Cortex J. *Neurosci,* 18:1161; Averback and Lee (2006) Effects of Noise Correlations on Information Encoding and Decoding, *J Neurophysiol* 95: 3633-3644, and because many (or all) transformations are carried out locally—that is, the transformation required for knee movements are laterally displaced in the tissue from those involved in ankle movements, etc, just as they are in the retina. (In the retina, transformations for different parts of visual space are carried out locally, and the transformations can be carried out very effectively assuming conditional independence among the cells. For example, in some typical cases, each location in visual space is handled by about 10-30 cells—thus one doesn't have to perform an optimization over thousands or even hundreds of neurons to obtain a good representation. Comparison of optimizations using large populations with those using local populations pieced together as independent groups indicates that local optimization provides satisfactory results.

It should be noted that the number of degrees of freedom for a movement is far, far less than in an image, and the motor system is much more redundant. For example, in some typical situations: there are about $2 \times 10^6$ optic nerve fibers (including both eyes), but roughly about $\frac{1}{10}$ that number of descending motor neurons (roughly $10^4$ per spinal segment, 30 spinal segments.) And on a per-cell basis, in typical cases, the motor system is also more redundant: there are about 1000, at least, motor neurons per muscle, even though only one time series (the force generated by that muscle) must be specified. In some cases, for a complete comparison one needs to compare contrast sensitivity and bandwidth for vision, with motor control precision and bandwidth, but in typical case these are comparable as well (1 part in 300 for visual contrast sensitivity, motor control is, in many cases, not finer than that; e.g., corresponding to a ~30-60 Hz bandwidth for both vision and motor.)

The greater redundancy of the motor system is also indicated by clinical and electromyographic results showing that about an 80% loss of motor neurons is typically required to have a clinical (functional) motor deficit.

Exemplary Implementation of Motor Prosthetic

Referring again to FIG. 2, the motor prosthetic 100, may incorporate encoders built using the techniques described here, e.g., implemented by the processor 102. The encoders are used in conjunction with an input receiver 101 and an output generator 103.

As described herein, in various embodiments, the strategy is to first develop encoders that capture the transformation from SMA activity to nerve branch activity (for arbitrary activity patterns), and, second, to use these encoders as an interface between SMA and the muscles (in patients in which the connections have been severed or otherwise impaired (anywhere along the pathway from SMA to muscle).

In some embodiments, what the encoders do is jump over the damaged area (bridge the gap) in real time or near real time; the muscle receives the signals or a close proxy of the signals it would normally receive—but it receives them through the device instead of the normal biological circuitry. Because the encoders mimic the normal transformations from SMA all the way down to the branches of the nerves that directly command the muscle, they can restore normal or near-normal movements.

Figure 3:
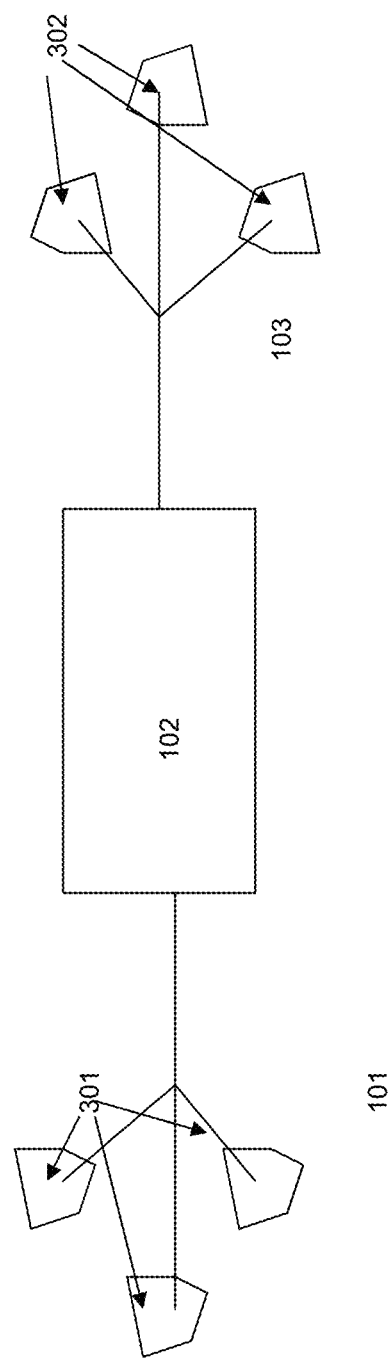
FIG. 3 is a schematic diagram of a neural prosthesis.

Referring to FIG. 3, in some embodiments the input receiver 101 includes a plurality of electrodes 301 embedded in the SMA (although three electrodes are shown, any suitable number may be used).

For example, in some embodiments, electrodes may be implanted in human SMA using techniques of the type described in Hochberg et al, 2006: Action potentials (e.g., of individual neurons or small groups of neurons) may be recorded, e.g., using a 10×10 array of silicon microelectrodes (e.g., of the type known in the art as a Utah array). In one embodiment, electrodes 1 mm in length protrude from a 4 mm×4 mm platform. Signals from the electrodes then pass through a titanium percutaneous connector to reach the outside environment. The connector is then connected to a recording system, which carries out amplification and unit identification on the signals from the electrodes, e.g., using the techniques described in Chestek et al, 2009. Note that in some embodiments, one may use single unit (e.g., single cell) activity as the relevant quantity in determining SMA activity. Additional or alternatively local field potential or multi-unit activity as recorded by each electrode in the array could play this role.

The measured SMA activity signals are then fed into the processor 102 that performs the operations of the encoders. In some embodiments, the electrodes and a battery pack are positioned subcutaneously, as in deep brain stimulation (DBS) methods familiar in the art, e.g., as used for Parkinson's patients. For this, a battery pack to drive the recording system is put in subcutaneously in the anterior chest wall with leads tunneled up to a site in the scalp to supply power to the recording system. An example of such a system is described in greater detail below.

The output of the encoders is then sent to muscle via the output generator 103. As shown, the generator includes an array of output electrodes 302. Again, although three output electrodes are shown, any number may be used. In various embodiments, and suitable technique for stimulating the muscle may be used. In some embodiments, the generator may be implemented using the techniques described in Moritz et al, 2008 and/or Guiraud et al, 2006.

For example, in some embodiments, each encoder output, determines the amplitude of the current pulse during a given time bin. In some embodiments, the time bins are typically 20 ms, following standard practice for stimulating muscles at 50 Hz, however, any suitable time bin duration may be used. In some embodiments, the maximum current (peak of the current pulse) will follow standard practice (i.e., about 10 mA), however, any suitable value may be used.

In some embodiments, after device implantation, the encoder must be optimized for the specific patient. For example, in the case of encoders used in prosthetics for humans, but based on experimental data from non-human primate subjects (e.g., monkeys) the optimization makes the necessary correction, e.g., it takes into account the fact that the encoder was determined for monkey, and the SMA of a monkey and a human are not the same size. Tuning may be accomplished in software in the encoder. In some embodiments, one may add a set of additional parameters to each encoder. These parameters determine the overall location and size of the patch of input neurons corresponding to $a_j$, as used in eq. 1. These parameters may be determined as follows for each target muscle: the patient is asked to attempt to execute a movement that normally results in contraction, isolated as well as possible to that muscle (note that because the patient cannot move the muscle because of neurologic damage, no movement will occur, but SMA will be activated because of the intent to move). The intent activates the neurons in the portion of the SMA that will provide the correct inputs to the encoder for that muscle. The tuning parameters are systematically varied until the muscle is in fact activated. Note that this tuning process can be expedited by functional MRI prior to implantation; this will narrow down the relevant region of SMA for each muscle.

In some embodiments, after device implantation, a gain factor that converts the encoder's output to the amplitude of the current pulse may be adjusted. This will be determined by asking the patient to make isolated movements as in the previous step, and adjusting the gain to produce the patient's desired output.

Exemplary Motor Prosthesis Device

Figure 4:
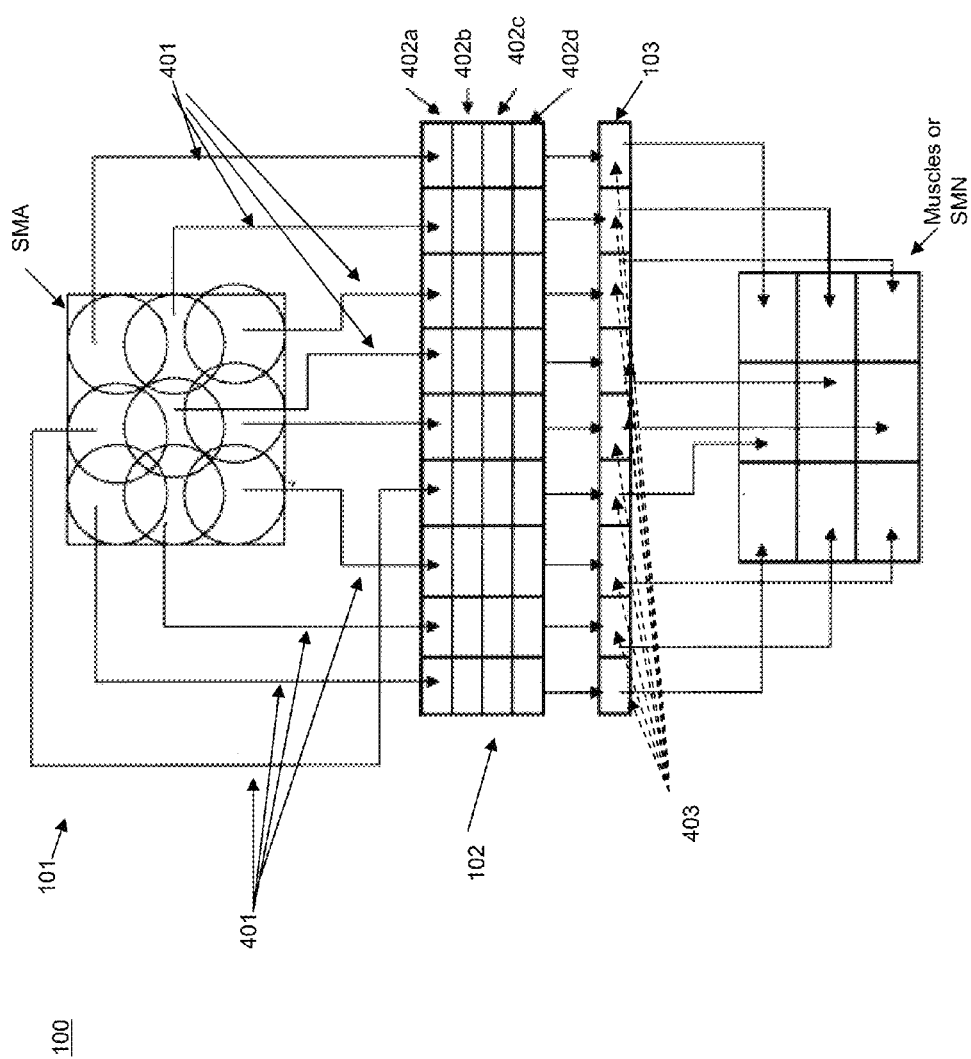
FIG. 4 is a schematic diagram of a neural prosthesis featuring multiple encoders.

FIG. 4 is a schematic diagram of an exemplary embodiments of the motor prosthesis 100. As shown the input receiver includes nine input devices 401 (e.g., electrodes) for measuring the activity of single neurons or groups of neurons in the SMA. The input signal measured by each input device 401 is sent to a corresponding encoder in the processor 102 (each encoder is represented as a vertical column).

The output of each processor is used to control a corresponding output generator element (e.g., an electrode, digital micromirror device element, or LED, as detailed below) 403 of the output generator 103. The output of the output generator elements drive a response in corresponding muscle or SMN cells.

Execution of the encoders proceeds in a series of steps, indicated in the figure as modules 402a-c: preprocessing 402a, spatiotemporal transformation 402b, and spike generation 402c. The output of the spike generation step may be nontransiently stored in a storage module 402d in preparation for conversion to a format suitable output, which may include a burst elimination step (not shown). The output is generated by the output generator 103. Note that output may be in the form of current pulses delivered as in as in either Moritz et al, 2008 or Guiraud et al, 2006 as is standard practice for stimulating muscles. Arrows show the flow of signals from specific regions of the SMA through the modules of the encoders, through output generator 103, which drives muscles or SMN.

Input Receiver

As noted above, in some embodiments, electrodes may be implanted in human SMA using techniques of the type described in Hochberg et al, 2006: Action potentials (e.g., of individual neurons or small groups of neurons) may be recorded, e.g., using a 10×10 array of silicon microelectrodes (e.g., of the type know in the art as a Utah array). In one embodiment, electrodes 1 mm in length protrude from a 4 mm×4 mm platform. Signals from the electrodes then pass through a titanium percutaneous connector to reach the outside environment. The connector is then connected to a recording system, which carries out amplification and unit identification on the signals from the electrodes, e.g., using the techniques described in Chestek et al, 2009. Note that in some embodiments, one may use single unit (e.g., single cell) activity as the relevant quantity in determining SMA activity. Additional or alternatively local field potential or multi-unit activity as recorded by each electrode in the array could play this role.

In other embodiments, any other suitable technique for measuring SMA activity may be used.

Processor/Encoder

As noted above, in the case of a motor prosthetic (the specific embodiment given below), the encoder mimics the transformation between Supplementary Motor Area (SMA) and spinal motor neurons (SMN)—that is, it jumps over the damaged primary motor cortex (a area commonly damaged by strokes) and interacts directly with the healthy cells, the SMN (or the muscles they synapse on), so that normal muscle contractions/relaxations can be made. These encoders use an algorithm that converts input signal from the SMA into patterns of electrical signals that are the same, or substantially similar, to that would be output in a normal subject. That is, the encoders jump all cells and circuitry between the input cells (corresponding to A in FIG. 1B) and the output cells (corresponding to C in FIG. 1B).

The prosthetic can use multiple encoders which can be assembled in a parallel manner as shown, for example, in FIG. 4, where different segments of the SMA activity are run through separate encoders, which, in turn, control different, specified output generator elements 403. In this embodiment, each encoder may have parameters suited for its operation, which may, for example, take into account the location and/or type of signaling cells being emulated by the encoder or being driven by the encoder's output. The term "code" can refer to a pattern of electrical pulses that corresponds to a pattern of action potentials (also referred to as spike trains) that the output cells produces in response to a stimulus or signals from upstream neurons. The term "code" may refer to bit streams corresponding to a pattern of spike trains. Each bit may correspond to the activity of one neuron (e.g., 1 means the neuron fires; 0 means the neuron does not fire). In other embodiments the bits correspond to other information (e.g., the firing rate of a population of neurons). The code may also be a continuous wave. Any type of waveform may be encompassed by the present invention, including nonperiodic waveforms and periodic waveforms, including but not limited to, sinusoidal waveforms, square waveforms, triangle waveforms, or sawtooth waveforms.

Figure 5:
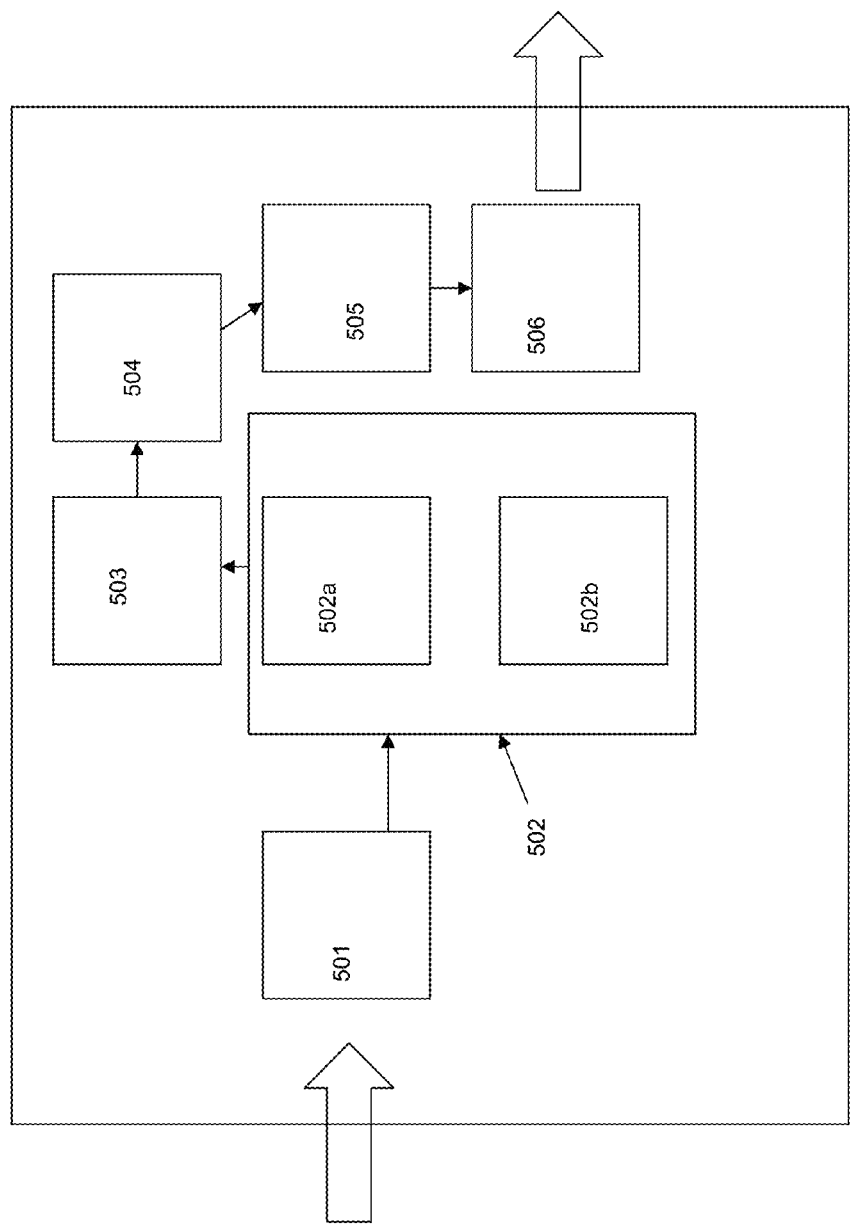
FIG. 5 is a functional block diagram of a processor for a neural prosthesis.

FIG. 5 shows a functional block diagram illustrating an exemplary embodiment of an encoder in the processor 102. As shown, the processor 102 includes a number of processing modules corresponding to the encoder, each operatively connected with one, several, or all other modules. The modules may be implemented on one or more processing devices (e.g., as described in detail below). As used herein, a module is considered to be substantially implemented on a given processor if substantially all essential computations associated with the function of the module are carried out on the processor.

The processor 102 includes a preprocessing module 501 which receives an input signal from the input receiver 101 and, e.g., rescales the signal for processing. In some embodiments, the preprocessing module implements processing analogous to that described in the Retinal Application subsection entitled "Preprocessing Step."

A spatiotemporal transformation module 502 receives the output of the preprocessing module and applies a spatiotemporal transformation (e.g., analogous to that described in the subsection of the Retinal Application entitled "Spatiotemporal Transformation Step") to generate, e.g., a set of firing rates corresponding to those that would have been generated by the output cells, e.g., to a digital pulse generator. In some embodiments, the spatiotemporal transformation module 502 includes a spatial transformation module 502a that convolves the input signal with a spatial kernel and a temporal transformation module 502b that convolves the output of the spatial transformation module 502b with a temporal kernel to generate a temporal transformation output. In other embodiments, e.g., where the processing involves an encoder with a non-separable spatiotemporal transformation, separate spatial and temporal transformation modules are not used.

In some embodiments, the processor 102 includes a nonlinear transformation module which 503 applies a nonlinear function to the spatiotemporal transformation output to generate the set of firing rates (e.g., as described in reference to Eq. 1 above). In some embodiments the nonlinear function is implemented using a look-up table.

A digital pulse generator module 505 generates digital pulse trains corresponding to the firing rates output from one or more of the other modules and generates a digital pulse train (i.e., a series of digital pulses) corresponding to each firing rate. These pulse trains are then output to the output generator 103. In some embodiments, the digital pulse generator module 505 implements processing of the type described in the subsection of the Retinal Application entitled "Spike Generation Step."

Figure 6C:
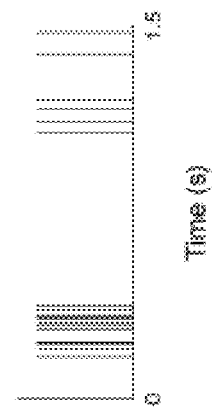
FIG. 6C is a plot of the pulsed output of a neural prosthesis train generated based on the digital pulse train of FIG. 6B.
Figure 6B:
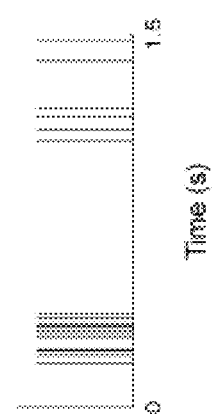
FIG. 6B is a plot of a digital pulse train generated based on the time dependent firing rate shown in FIG. 6A.
Figure 6A:
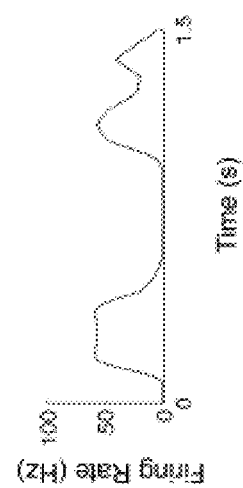
FIG. 6A is a plot of a time dependent firing rate generated by an encoder of a neural prosthesis.

FIGS. 6A-6C show an example of the generation of a spike train output based on a calculated firing rate. FIG. 6A shows the time dependent firing rate calculated by the encoder. FIG. 6B shows the corresponding spike train generated by the pulse generator module 505. FIG. 6C shows the corresponding output of the output generator 103.

Referring back to FIG. 5, in some embodiments, an interpolation module 506 is used to generate data having temporal resolution higher than the measurement rate of the input receiver 101. In one embodiment, the interpolation module 506 receives output from the spatiotemporal transformation module 502, applies interpolation, and passes the results on to the nonlinear transformation module 503. In other embodiments, the interpolation may be applied after the nonlinear transformation, e.g., to directly interpolate firing rates prior to input into the digital pulse generator 506. In some embodiments, the interpolated information has a temporal resolution corresponding to at least 2, at least 5, at least 10, at least 20, or at least 50 times or more the measurement rate of input receiver 101.

In some embodiments, a burst elimination module 507 is provided which operates on the output of the digital pulse generator module 505 to reduce or eliminate the presence of bursts. In some embodiments, the burst elimination module 507 implements burst elimination processing analogous to the type described in the subsection of the Retinal Application entitled "Spike Generation Step."

Figure 7:
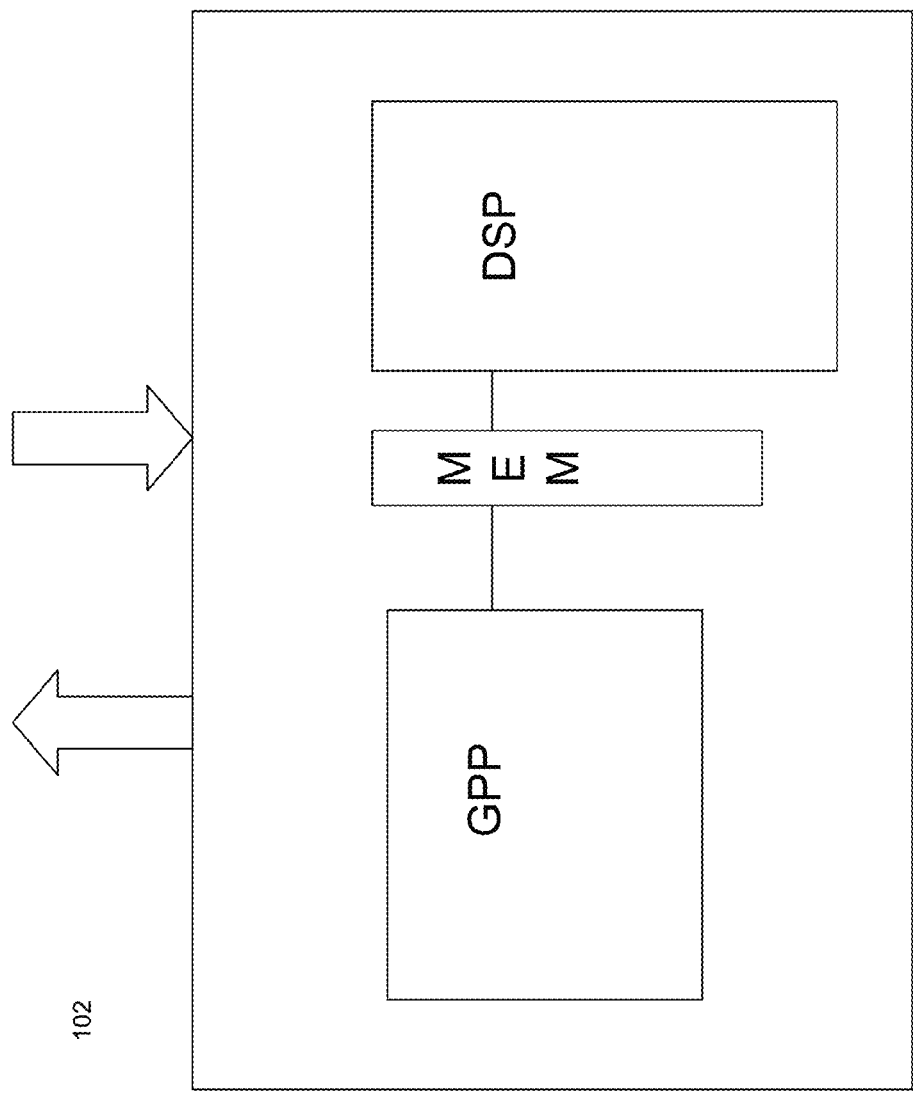
FIG. 7 is a functional block diagram of a processor featuring a parallel processing architecture.

FIG. 7 shows an exemplary embodiment of the processor 102 featuring a dual processor architecture. As shown, the processor 102 includes a general purpose processor (GPP) and a digital signal processor (DSP), e.g., integrated onto a single chip. The GPP and DSP are connected to a shared memory (MEM). The processor 102 receives data from input receiver 101, e.g., via the shared memory. The processor 102 outputs data, e.g., to the output generator 103.

In one embodiment, the DSP is a Texas Instrument TMS320C64 series processor. The GPP is an ARM Cortex A8 processor, and the shared memory is an SDRAM (e.g., with 512 MB of memory). In various embodiments, other suitable processors known in the art may be used. Some embodiments may feature more than two parallel processors and more than one shared memory.

The platform shown in FIG. 7 is capable of highly-parallel computation. The processing flow may be pipelined, as described above, with the implementation of various processing steps or modules divided between the processors. In general, the more computationally expensive processing tasks (e.g., tasks involving complicated matrix operations, convolutions, interpolation etc.) may be assigned to the DSP, with less expensive tasks (e.g., scaling operations, pulse generation, process synchronization and other "housekeeping" tasks, etc.) may be assigned to the GPP.

The table below shows an exemplary assignment of the processing steps. However, in other embodiments, different assignments may be made.

TABLE 1

Dual Processor Assignments

| Processing Step | Processor Assigned |
|---|---|
| Preprocessing | GPP or DSP |
| Spatial Transformation | DSP |
| Temporal Transformation | DSP |
| Interpolation | DSP |
| Nonlinearity | GPP |
| Digital Pulse Generation | GPP |
| Burst Elimination | GPP |
| Output | GPP |

In some embodiments, one, several, or all of the preprocessing module, the spatiotemporal transformation module, and the interpolation module are all substantially or entirely implemented of the DSP. In some embodiments, one, several, or all of the scaling module, nonlinear transformation module, the digital pulse generation module, and the burst elimination module may be substantially or entirely implemented of the GPP. This implementation of the modules may lead to a particularly advantageous processing throughput and reduced processing time. However, in various embodiments, other suitable implementations may be used.

Although some exemplary embodiments of a processor for the prosthetic device 100 are set out above, it is to be understood that in various embodiments, other processing devices may be used. The processing device, e.g., hand-held computer, can be implemented using any device capable of receiving a data and transforming them into output with acceptable speed and accuracy for the application at hand. This includes, but is not limited to, a combination general purpose processor (GPP)/digital signal processor (DSP); a standard personal computer, or a portable computer such as a laptop; a graphical processing unit (GPU); a field-programmable gate array (FPGA) (or a field-programmable analog array (FPAA), if the input signals are analog); an application-specific integrated circuit (ASIC) (if an update is needed, the ASIC chip would need to be replaced); an application-specific standard product (ASSP); a stand-alone DSP; a stand-alone GPP; and the combinations thereof.

In one embodiment, the processing device is a hand-held computer (Gumstix Overo, Gumstix, San Jose, Calif.), based around a dual-core processor (OMAP 3530, Texas Instruments, Dallas, Tex.) that integrates a general purpose processor (GPP) and a digital signal processor (DSP) onto a single chip. This platform is capable of highly-parallel computation and requires much less power than a typical portable computer (~2 Watts or less, compared to 26 Watts for a standard laptop computer). This allows the transformation to be computed in real-time, on a device that is portable and can be powered on a single battery for long periods of time. For example, typical laptop batteries, with charge capacities in the range of 40-60 Watt-hours, could run the processor continuously for about 20-30 hours. In another embodiment, all or a portion the processing device is small in size so that it can be worn by a patient (as detailed below). In other embodiments, other suitable computing devices may be used, e.g., a Beagleboard device available from Texas Instruments of Dallas, Tex.

Output Generator

As described in the device component of the Retinal Application, the encoder or encoders could drive many output elements. Several output generator interfaces for driving target cells are possible.

For example, in some embodiments, the cells to be driven by the output of the prosthetic 100 (i.e., the set C shown in FIG. 1A) may be sensitized to light, e.g., using a light-activated transducer (such as Channelrhodopsin-2). The output generator 103 could be an LED array, a set of fiber optics driven by an LED, a digital light processing (DLP) device, among others.

These optical devices would output pulses of light that correspond to the activity patterns of the cells in C. The pulses of light would drive the light-activated transducer, causing the cells in C to fire as the encoder specifies. For example, the encoder would send signals to a general purpose input/output (GPIO), which would signal the LEDs.

For example, in some embodiments, an encoder's output is a set of spike times (times at which an action potential should be produced in the downstream neuron). Because the output is in a sense binary (at each moment in time, a spike does or does not occur), this can be naturally converted into a program that sends high/low information to the GPIO. The GPIO then outputs voltage that is "high" and turns the LED on, or "low" and does not turn it on. In other words, the encoder produces a set of spike times, which get converted into TTL pulses through the software and the GPIO, and pulses current then goes down a wire from the GPIO to the LED. The temporal resolution of the spike times produced by the encoder may be sub-millisecond or any other suitable value.

The TTL pulses are the length of the neural signal (e.g., about 1 ms for an action potential.) In this example, the LEDs are separately addressable (one for each encoder); however, other methods that allow better use of interface materials (data compression), such as multiplexing or making use of correlations in the pulse patterns of the encoders to get many signals through to many LEDs rapidly, may be used. Finally, the addition of an amplifier to drive up signals to the LEDs may be built in as well (to allow the neurons receiving the light pulses to fire in a one-to-one manner or a near one-to-one manner with the pulses they receive).

For output generators based on electrodes, the output generator could consist of any device capable of driving current into the electrodes.

In general, as will be apparent to one skilled in the art, for various applications, any of the output generation techniques described in the Retinal Application may be adapted for use in the devices described herein.

Exemplary Deployment of the Motor Prosthesis on a Human Subject

Figure 8A:
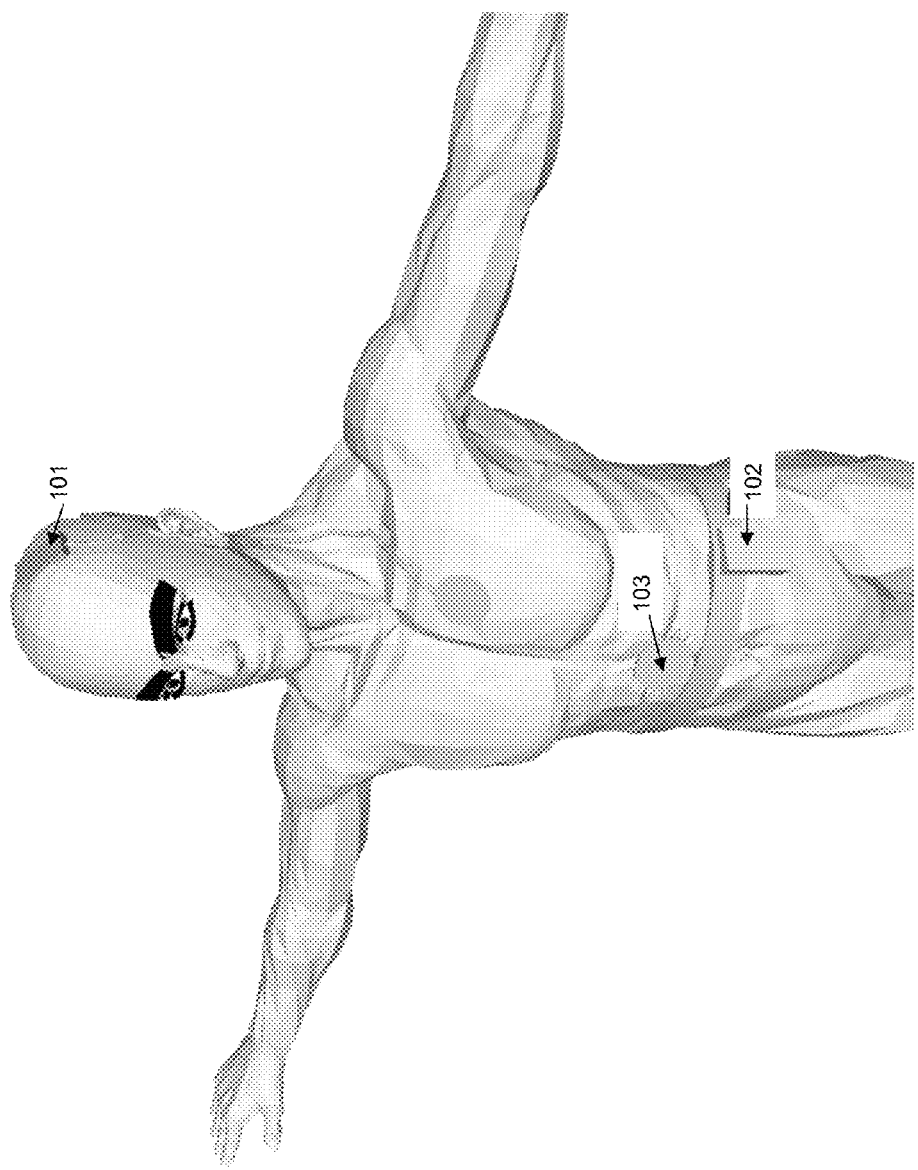
FIG. 8A is an illustration of a neural prosthesis deployed in and on a human subject.

Referring to FIG. 8A, in one embodiment of the motor prosthetic 100, electrodes of the input receiver 101 are implanted in SMA. The electrodes and a battery pack are all subcutaneous, as in deep brain stimulation (DBS) methods used for Parkinson's patients. The battery pack to drive input receiver 101 is put in subcutaneously in the anterior chest wall; it has leads that are tunneled up to a site in the scalp so it can supply the needed power to the recording system.

The signals from the input receiver are sent wirelessly to the processor 102, implemented in a unit worn on a belt with its battery pack.

Figure 8B:
FIG. 8B is an x-ray snapshot of an implanted portion of the neural prosthesis of FIG. 8A.

The processor then drives output generator 103, as shown implemented as an implanted muscle stimulator system which is also completely internal to the human subjected including a power source. In some embodiments, the stimulator system may be of the type described in Guiraud et al, 2006. In some embodiments, the dimensions of the stimulator are comparable to the battery pack used for pacemakers (e.g., about 6 cm×6 cm). In one embodiment, including the connectors to muscle, the width of the stimulator is about 10 cm. FIG. 8B shows an X-ray snapshot from Guiraud et al, 2006, showing actual size of an exemplary stimulating device inside a human.

Procedures for Measuring Motor Prosthetic Performance

The following describes exemplary procedures for measuring the performance of the prosthetic 100 and its encoders. Performance of the encoders can be measured on a forced choice activity discrimination task or performance on an error pattern test. The term "test stimulus" that will be used herein, refers to pattern of muscle activity, measured using EMG.

To evaluate performance on a forced choice discrimination task, a known test in the art, a confusion matrix is used (Hand D J. 1981). A confusion matrix shows the probability that a pattern of nerve branch activity ($\vec{c}$, the population comprising the individual activities of each subpopulation $c_i$) corresponds to its appropriate pattern of SMA activity, $\vec{c}_{[k]}$. To generate different patterns of SMA activity, the animal (or human) is required to carry out an array of stereotyped movements (e.g., moving a cursor to one of several locations on a computer monitor). Each kind of movement (for example, the movement to each location) is repeated for many trials, thus giving a set of SMA activities. For each movement type k, the set of SMA activities is denoted $\vec{a}_{[m]}$, and the set of resulting nerve branch activities is denoted $\vec{c}_{[k]}$.

With respect to the matrix, the vertical axis gives the movement type k. The horizontal axis gives the movement type predicted by decoding the pattern of nerve branch activity $\vec{c}_{[k]}$; the decoded movement type is denoted m. The matrix element at position (k,m) thus gives the probability that nerve branch activity $\vec{c}_{[k]}$ is decoded as movement type m. If m=k, the nerve branch activity pattern is decoded correctly, otherwise, it is decoded incorrectly. Put simply, elements on the diagonal indicate correct decoding; elements off the diagonal indicate confusion.

To generate the confusion matrices, we divide the data into two sets: a training and a testing set. The training set is obtained in order to build response distributions, and the testing set is obtained for decoding.

To decode each pattern in the test set, $\vec{c}_{[k]}$, we determine the pattern of SMA activity that was the most likely to have produced it. That is, we determine the pattern $\vec{a}_{[m]}$ for which $$p(\vec{a}_{[m]} | \vec{c}_{[k]})$$

was maximal. Bayes' theorem is used, which states that $$p(\vec{a}_{[m]} | \vec{c}_{[k]}) = p(\vec{c}_{[k]} | \vec{a}_{[m]}) p(\vec{a}_{[m]}) / p(\vec{c}_{[k]}),$$

where $p(\vec{a}_{[m]} | \vec{c}_{[k]})$ is the probability that the pattern $\vec{a}_{[m]}$ in the SMA was present, given that the particular $\vec{c}_{[k]}$ was present in the nerve branches. $p(\vec{c}_{[k]} | \vec{a}_{[m]})$ is the probability that a particular $\vec{c}_{[k]}$ occurred given a particular $\vec{a}_{[m]}$, and $p(\vec{a}_{[m]})$ is the prior probability of $\vec{a}_{[m]}$. $p(\vec{a}_{[m]})$ is set uniform in this experiment and so, by Bayes Theorem, $p(\vec{a}_{[m]} | \vec{c}_{[k]})$ is maximized when $p(\vec{c}_{[k]} | \vec{a}_{[m]})$ is maximized. When $p(\vec{a}_{[m]})$ is uniform, as it is here, this method of finding the most likely pattern $\vec{a}_{[m]}$ given a pattern $\vec{c}_{[k]}$ is referred to as maximum likelihood decoding (Kass et al. 2005; Pandarinath et al. 2010; Jacobs et al. 2009). For each occurrence of a movement type k that that was decoded as m, the entry at position (m,k) in the confusion matrix is incremented.

To build the distributions needed for the decoding calculations used to make the confusion matrices (i.e., to specify $p(\vec{c}_{[k]} | \vec{a}_{[k]})$), the procedure is as follows. As mentioned above, the subject makes N types of movements (where N is typically 8), and each is repeated many times (e.g., >20 times). For each movement, we obtain a pattern of SMA activity $\vec{a}_{[k]}$, which we record via the implanted electrodes, and we obtain a pattern $\vec{c}$. Each pattern $\vec{a}_{[k]}$ is taken as the spike train spanning from ~1 sec prior to movement onset to ~200 ms following movement onset, and binned with 10-100 ms bins. Each pattern $\vec{c}_{[k]}$ is taken as the nerve branch activity over the same period and binned in the same way. In both cases, the spike generation process is assumed to be an inhomogeneous Poisson process, and the probability of any given pattern of activity for the entire period is calculated as the product of the probabilities for each bin. The probability assigned to each bin is determined by Poisson statistics, based on the training set response in this bin. Note that this can be done by averaging over all trials for a given type of movement pattern, or by considering each trial individually.

Once the confusion matrices are calculated, overall performance in the forced choice activity discrimination task is quantified by "fraction correct", which is the fraction of times over the whole task that the decoded movement type m was correctly matched to the movement type k.

Given this procedure, at least 3 sets of analyses may be performed. For each one, the activity patterns from the normal subject are used for the training set and a different set of activity patterns is used for the test set, as outlined below:

(1) The first set should consist of the test sets described above, i.e., out-of-sample activity patterns from the normal subject. (These are recordings of activity patterns in SMA and the nerve branches that were not used to make the training set.) We use the fraction correct produced by the activity patterns from normal subjects as the baseline correct performance.

(2) The second set should consist of the responses from the encoders. These are the responses $\vec{a}_{[k]}$ calculated from eq. 1, from the recorded SMA activity patterns $\vec{a}_{[k]}$. Responses from this test set yield a measure of how well the encoders perform, given the training set response distributions used for analysis (1). The reason for performing the analysis this way is that we want to compare the encoder's performance against the normal baseline condition.

When responses from the encoder are used as a test set, one obtains a measure of how well the motor system would do with our proxy of the transformation from SMA to the peripheral nerve branch activity (our proxy of the motor system code).

(3) The third set, which is carried out only in subjects in which the normal pathway from SMA to muscle has been damaged, is to determine the confusion matrix that relates the movement actually made, to the movement that was intended. Since the normal pathways are damaged, the movement results from applying the prosthetic's encoder signals, determined as in analysis (2), to the muscles via the output generated (in this example, output uses electrodes, see above). The movement intended is determined from the subject's verbal responses, and can be verified by decoding the patterns of activity in SMA that are produced at the time of intention. This analysis provides a measure of how well the prosthetic performs after its output has been passed through the to real tissue. This is a bottom-line measure of the prosthetic's performance in patients.

The encoder's performance and prosthetics performance in the forced choice discrimination task, as measured by "fraction correct", will be at least about 35%, 50%, 60%, 70%, 80%, 90%, 95%, 99%, or 100% of the performance of the normal system, or better than the normal system, measured as described above. Moreover, these performance levels may be obtained with response time for the prosthetic 100 which is substantially the same as those found in an unimpaired subject. That is, in some embodiments, the prosthetic 100 in jumping impaired signaling cells introduces a lag time of which is of suitably short duration. For example, in some embodiments the lag time is less than a factor of 5, 4, 3, 2, 1, 0.5, 0.1, (e.g., a factor in the range of 0.1-5 or any subrange thereof) or less times the signaling time exhibited by a normal subject.

Although a number of examples of neural prosthetic devices and techniques have been presented above, it is to be understood that numerous modifications are possible.

For example, the above description of the strategy to find the transformation to be implemented by the encoders; there are a number of variations that may be used.

In various embodiments, there are options for how spike trains (either input from A or output to C) are represented. For example, they can be represented as a point process in continuous time; they can be smoothed into continuous rate functions, and they can be binned. In typical embodiments, the data collected at both A and C is in the form of a point process, but under some conditions it is easier to perform optimizations with smooth representations.

The smooth representations, then, can be reconverted to spike trains by assuming, for example, Poisson spike generation. Related to this, note that some embodiments can also use a non-spiking measure to capture the neural activity in area A, such as a local field potential or optically recorded signal. These represent a local average of neural activity, and (e.g., in circumstances that do not require resolution at the single neuron level), may provide a more stable measurement. In these cases, the smooth representation of activity in A is used directly for determining the transformation.)

In various embodiments, there are options for the cost function to be used in optimization of the encoder transformation model. The examples presented above use the likelihood, because it is well principled, but under many circumstances, a mean-squared-error is an excellent approximation and the optimization is faster to perform. Note, in regard to the previous paragraph, that in order to use mean-squared-error, some form of binning or smoothing is required.

In various embodiments, while the choice of a linear-nonlinear cascade is a natural and principled one, other functional forms may also be applicable, such as models with dynamic gain controls or neural network models, or any transformation that can be expressed, explicitly or implicitly, as a solution of a system of integral, differential, or ordinary algebraic equations, whose form and coefficients are determined by experimental data. This also includes models in which activity among the neurons in region C is correlated, e.g., via recurrent feedback.

Further, while in may cases it is most straightforward to fit the model parameters for each neuron in A independently, in some applications these parameters may have a systematic dependence on the neuron's location. Identification of this dependence will reduce the number of independent parameters that must be fit, and, potentially, allow for generalization of the model to neurons not actually recorded.

Also, it is notable that in embodiments where the prosthesis device performs a jump to muscle, an involved extra transformation (e.g., from SMA output to muscle response) is likely linear, so the cascade becomes linear nonlinear linear (LNL) transformation to go from SMA to muscle.

Auditory Prosthesis

In several of the examples above, a prosthesis 100 is described which is used to restore or improve communication from one set of healthy cells A to another set of health cells C by jumping a set of impaired signally cells B that separate the sets of healthy cells.

Figure 9:
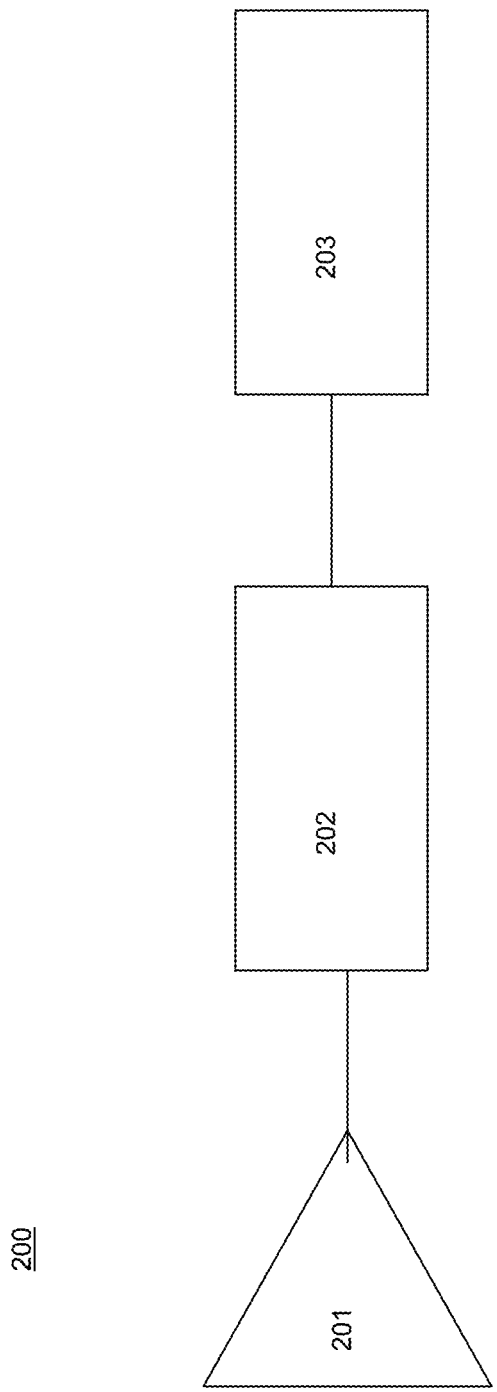
FIG. 9 is functional block diagram of an auditory prosthesis.

As noted above, in some embodiments, the input signal to the prosthesis is an external stimulus instead of the activity of the set of healthy cells A. For example, FIG. 9 shows an auditory prosthetic 200. The prosthetic 200 is a device to bypass damaged hair cells in the inner ear, that is, to jump from sound stimuli directly to the output of the cochlea (the output of the spiral ganglion cells).

The prosthesis 200 includes an input receiver 201 for detecting an audio signal (e.g., a microphone or other sound transducer) an converting the audio signal to, e.g., a digital format. A processor 202 (sometimes referred to herein as an encoder unit) processes the input signal from the input receiver 201 using a set of encoders to generate a set of coded outputs. An output generator 203 (e.g. an electrode or optical device of the types described herein), in response to the coded outputs, activates auditory nerve cells (e.g., spiral ganglion cells) to produce a response to the audio stimulus, e.g., a response that is substantially the same as the response in an unimpaired subject.

A well functioning auditory prosthesis, e.g., one that can provide near normal or normal function in an impaired subject is advantageous because the incidence of hearing loss as the population ages is very high.

As in the examples presented above, an important aspect of the prosthetic 200 is the functioning of the encoders implemented by the processor 202. These are the components that carry out the transformation from sound to cochlear output. As discussed above for the motor prosthetic and for the visual prosthetic described in the Retinal Application, an advantage of this approach is that it has the capacity to generalize. it does this by using a mathematical transformation that captures the relation between the outside world (in this case, audio stimuli) and the activity of a set of neurons. The techniques used here are directly analogous to those used to generate the motor encoders described above and visual encoders described in the Retinal Application. The following discussion uses the notation developed herein for the motor encoders for convenience. However, one skilled in the art will recognize that the formalism and techniques used in the Retinal Application may be readily adapted to the present case of an auditory prosthesis.

Again the approach for building the encoders is phenomenological: One may parameterize the relationship between the external stimuli and a set of neural signals or between two sets of neural signals, and find the parameter values using an optimization procedure, such as maximum likelihood.

Note that in various embodiments, the prosthetic 200 uses signaling that is not limited to frequency coding or intensity coding, but uses natural coding derived directly from data. That is, each encoder is essentially a complete model for the input/output relations for a class of SG cell, where the input is the sound stimului (such that the hair cells are being jumped). This means it has the capability to transform any sound stimulus into the normal auditory output for that class of cell. The encoders of the prosthesis 200 thus carry much more information that simple frequency detectors and transmitters (e.g., of the type described in Boyden, 2010, U.S. Pat. Pub. No. 2010 0234273).

Constructing Auditory Encoders Using Experimental Data:

In some embodiments, encoders are constructed from data collected from spiral ganglion (SG) neurons in an unimpaired subject while sound stimuli are presented. In some embodiments, one may implant an array of extracellular electrodes e.g., using the techniques described in Sellick 1982. Accordingly one obtain firing patterns from an array of SG neurons. At the same time, one may present sound stimuli. One may formalize the relation between the sound stimuli and the SG responses as $\vec{c} = \vec{f}(\vec{a})$, where $\vec{a}$ is vector representing the sound (as a time series), and $\vec{c}$ is the pattern of neural activity in the SG neurons. Note that $\vec{a}$ is univariate (it's a vector where the components are sound (pressure) as a function of time) and $\vec{c}$ is multivariate (as above, it represents the activity of a population of neurons, the SG neurons). In some embodiments, the transformation may instead operate on the frequency spectrum of the sound. As will be readily understood by one skilled in the art, such a frequency spectrum may easily be obtained from $\vec{a}$ via a Fourier transform (e.g., performed by processor 202 implementing an algorithm such as the well known Fast Fourier Transform).

To generate generalizable encoders, one may use the same strategy discussed herein for generating the retinal encoders and the motor encoders. One may provoke the system with a broad range of stimuli. In the case of the retinal encoders, we presented the retinas from normal subjects with two classes of stimuli—artificial (white noise) and natural scenes—and recorded ganglion cell responses. We then modeled the transformation from stimulus to response. The "training" stimuli (the white noise and natural scenes) were broad enough to produce a general model, one that was effective on any stimulus. In other words, given the training stimuli, we obtained a model that faithfully reproduced ganglion cell responses to essentially any stimuli (stimuli of arbitrary complexity).

Here, with the auditory system, one may take the same approach. On may present white noise (WN) and natural sound (NS) stimuli, where the latter falls into two categories, environmental sound and sound relevant to language (both described in, for example, Lewicki, 2002.

Given the data sets generated in the previous step, one may model the transformation between the sound stimuli and the SG responses. This provides a set of encoders, e.g., one for each SG cell or corresponding to a small group of SG cells (e.g., containing less than 2, less than 3, less than 5, less than 10, less than 20, less than 30, less than 50, or less than 100 cells, e.g., in the range of 1-1000 cells or any subrange thereof).

As for the motor prosthetic, one may use the following parametric form, and determine the parameters of the form by optimizing a cost function separately for each SG neuron: for each SG neuron, $c_i$ determine weight functions, $\vec{w}_i$, and a nonlinearity, $N_i$, so that the modeled transformation $c_i^{fit} =$ $N_i(\vec{a} \cdot \vec{w})$ is an optimal match to the actual transformation, $c_i = f_i(\vec{a})$. $N_i$ is a pointwise nonlinearity, i.e., a function $y = N_i(x)$, where x and y are both real-valued quantities (in the case of the retinal encoders, $N_i$ was a cubic spline with 7 knots, but any suitable choice may be used), and $\vec{w}$ is a vector of weights, specific to the output each SG neuron i. $\vec{w}_i$ consists of an array of quantities $w_j(t)$, where i labels a neuron in the SG population, and t is time. The ith component of the dot product $\vec{a}$ is calculated as follows:

$$\Sigma a(t) w_i(t)$$

Note that this differs slightly from the parallel equation for the motor prosthetic in that it has no subscript j; this is because the quantity a here is a one-dimensional function of time (or frequency in the case where an Fourier transform has been applied). As was the case for the encoders for the retina and motor systems, the optimization is performed to maximize the expected log likelihood over the entire output population, namely, $$L = \left\langle \sum_i ll(c_i^{fit}, \vec{a}) \right\rangle$$

$ll(c_i^{fit}, \vec{a})$ denotes the log likelihood that $c_i^{fit}$ accounts for the observed activity of the ith neuron in SG, when $\vec{a}$ is the sound input, and the brackets denote an average over all inputs. This likelihood is calculated from Poisson statistics based on the model firing rates (i.e., $c_i^{fit}$).

The weights $\vec{w}_i$, i.e., the arrays $w_{i,j}(t)$ correspond to a set of linear filters, one for each neuron i in the SG, and $N_i$ is an adjustable nonlinearity for neuron i.

Exemplary Implementation of Auditory Prosthesis

Referring again to FIG. 9, the auditory prosthesis 200 may incorporate encoders built using the techniques described here, e.g., implemented by the processor 202. The encoders are used in conjunction with an input receiver 201 (e.g., a microphone) and an output generator 203 which stimulates a response in the SG cells.

As described herein, in various embodiments, the strategy is to first develop encoders that capture the transformation from audio stimulus to SG activity (for arbitrary activity patterns), and, second, to use the coded output these encoders to jump impaired cochlear hair cells and directly stimulate the SG cells to restore normal or near normal function.

In various embodiments, the output generator 203 may include any suitable technology for stimulating SG neurons, such as that of they type describe in Zeirhofer et al., 1995 or Zeng et al, 2009. For example, in the embodiment shown in FIG. 10A the prosthesis 200 works as follows: 1) a microphone included in the input receiver 201 sends signals to a processor 202, 2) the signal processor 202 converts the signals from the microphone to signals to drive an array of electrodes in output generator 203, and 3) the signals from processor 202 control the electrodes that stimulate the SG neurons.

As shown, the microphone and a signal processing portion 202a of the processor 202 are located outside of the subject. The signal processing portion 202a generated coded outputs, and transfers them, e.g., via a radio frequency (RF) or other wireless link to a subcutaneously implanted portion 202a of the processor 202. The implanted portion receiver the signal and controls the electrodes to stimulate the SG cells.

In other embodiments, all of the processing may occur externally, with an RF signal being used to directly drive implanted electrodes. In various embodiments other implementation schemed may be used. In some embodiments, an external power supply provides power to the subcutaneous elements, e.g., via an RF or inductive power coupling, or any other power transmission technique known in the art.

FIG. 10B shows a variant of the device of FIG. 10A, where the output of the encoders is sent not to electrodes, but to light emitting diodes (LEDs) included in the output generator 203 (or another light sources) to drive alternate transducers, e.g., channelrhodopsin-2 (ChR2) used to sensitive the SG cells. Pulses from the LEDs are used to drive a response in the sensitized SG cells.

In various embodiments, expression of ChR2 or other transducer genes in SG neurons can be achieved using the gene promoters described in Table 1 of Liu et al, 2007. Examples include EF-1\alpha, NSE, CMV, CAG; these all express in SG neurons. In various embodiments, any other suitable promoters may be used.

With respect to delivery of the gene, any of the same gene therapy approaches described in the Retinal Application can be used for delivery to SG cells. Lentivirus (LV), adenovirus-5 (Ad-5) and adeno-associated virus-2 (AAV-2) have been shown to penetrate, although (Ad-5) was found to be the most effective (under conditions where the round window of the cochlea, one of the openings to the inner ear, was left intact (Lei et al, 2010). If the round window is partially digested, then AAV-2 becomes effective (Wang et al, 2011); this is valuable in some applications, as AAV-2 is one of the more promising gene therapy vectors in terms of safety (Simonelli et al, 2010). In various embodiments, any other suitable delivery technique may be used.

Figure 11A:
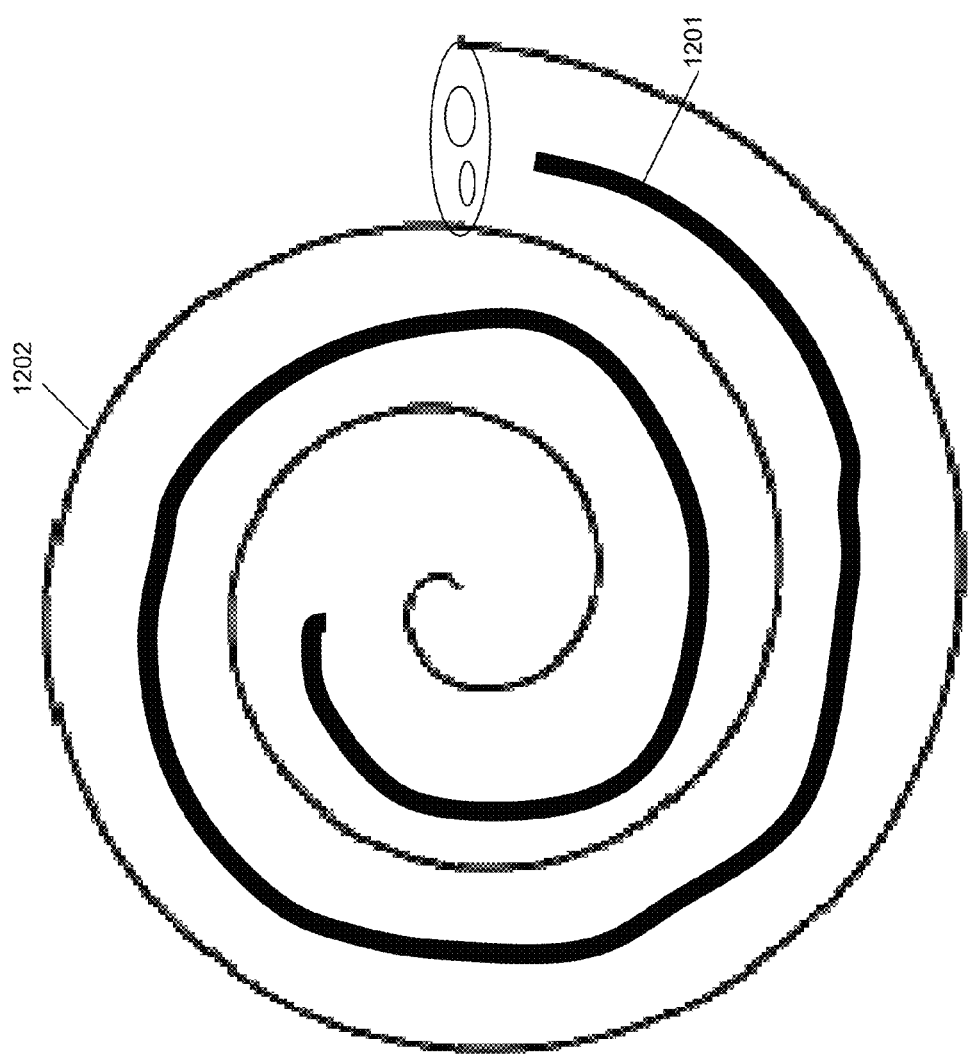
FIG. 11A is a schematic illustration of a flexible LED array implanted in the cochlea of a subject.
Figure 11B:
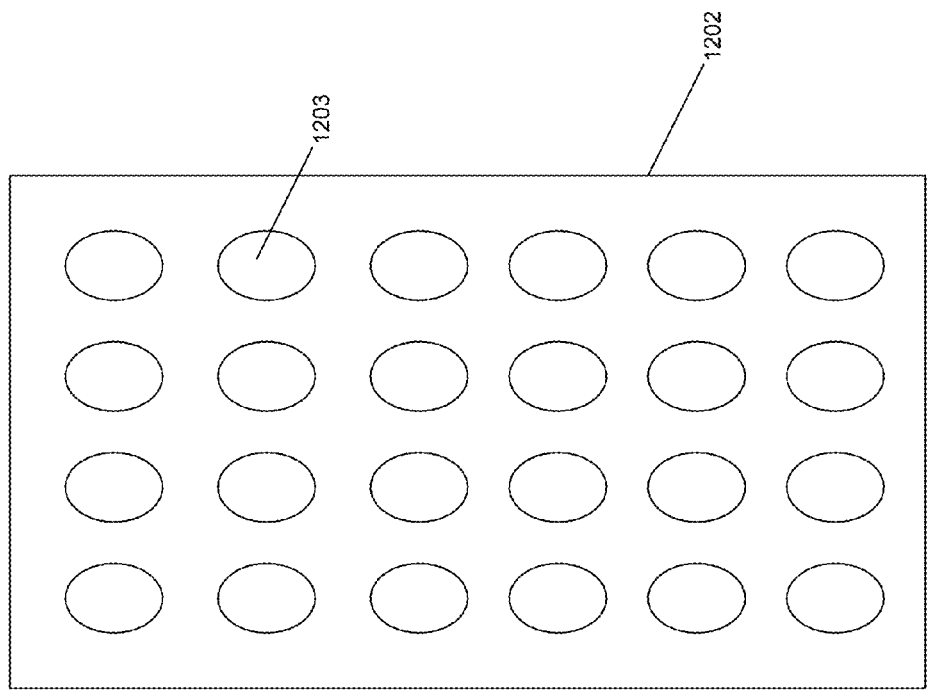
FIG. 11B is a top down view of the a flexible LED array of FIG. 12A prior to implantation.

Referring to FIGS. 11A and 11B, in some embodiments, the output generator 203 includes a thin flexible LED array 1201 implanted in the cochlea 1202 of a subject. The flexible array is able to conform to the spiral shape of the cochlea, such that the LEDs may be positioned to stimulate SG cells. Note that although one possible configuration of the array 1201 is shown, and other suitable positioning, array size, etc.

In some embodiments, the array 1201 includes an arrays of interconnected, ultrathin LEDs 1203 that are built into a flexible waterproof material. In various embodiments, the device can be placed into the inner ear to stimulate the ChR2-expressing SG cells. In one embodiment, each LED is 100 by 100 microns, which would stimulate multiple cells; however, one can narrow its light path to target fewer cells by masking a portion of the LED. In some embodiments, the size of the masking may be optimized to allow sufficient intensity to reach the ChR2; "sufficient intensity" is defined as that which produces action potentials that follow the output of the encoder in a one-to-one or near one-to one manner.

In some embodiments, the flexibility of the array 1201 matches well with the curvature of the cochlea 1201: For example, in humans the radius of curvature of the cochlea ranges from 4 mm at the high frequency end to 0.7 mm at the low frequency end, while in some embodiments, the radius of curvature of the flexible device is e.g., 0.4 mm or less.

In some embodiments, the array 1201 may be of the type described in Kim et al, 2010. In various embodiments, the array 1201 may be operatively connected to the processor 202 using any suitable technique including, e.g., a wired or wireless connection.

In some embodiments, after device implantation, the encoder may be optimized for the specific patient. Two examples of optimization are the following. First, in some cases, different encoders capture different information (e.g., frequencies, intensity), so they need to be positioned on the SG neuron array to stimulate the appropriate SG cells (the SG cells that carry the same information). Second, in some embodiments, threshold levels and maximum levels have to be determined. This can be achieved using extracellular electrodes (e.g., using pure tones to drive a small number of cells at a time).

Methods for Measuring Auditory Prosthesis Performance

The following describes exemplary procedures for measuring the performance of the prosthetic 200 and its encoders. In some embodiments, the procedure for measuring the performance of the encoders and the prosthetic will follow directly from that used to test the retinal prosthetic or motor prosthetic, focusing specifically on performance on a forced choice discrimination task. The term "test stimulus" that will be used herein, refers to a stimulus or a stimuli, which is presented to an animal for evaluation of performance of the encoders or encoders and output generator (e.g., the auditory prosthesis 200).

In various embodiments, it is important that the task used to measure prosthetic performance falls into a range of difficulty that allows meaningful information to be obtained. Briefly, the task must be difficult enough (i.e. must use a stimulus set rich enough) that the normal retinal responses provide information about the stimuli, but do not perform perfectly on the task. For example, in the task shown in Example 8 in the Retinal Application, the fraction correct using the responses from the normal retina, was 80%, satisfying this criterion. If the task used had been too hard, such that the normal retina's performance were near chance, then matching would have been of limited use to a performance analysis. Conversely, if the task chosen had been too easy (e.g., requiring just gross discriminations, such as black versus white, and where the fraction correct for the responses from the normal is near 100%), then prosthetic methods that are far from approximating the natural code and provide nothing close to normal vision would appear to do well. The same applies to the auditory tests: it is critical to use an appropriately challenging test, as was used in the examples in the Retinal Application. The use of a challenging test also allows one to determine if the prosthesis is performing better than the auditory system (i.e., entering into the domain of "bionic hearing").

Various methods for the forced choice task follow directly from those analogous used in the Retinal Application, converting to auditory stimuli. Two types of natural stimuli may be used—natural environment sound stimuli and speech-sound stimuli, as described in, for example, Lewicki, 2002. To evaluate performance on a forced choice discrimination task, a known test in the art, a confusion matrix is used (Hand D J. 1981). A confusion matrix shows the probability that a response to a presented stimulus will be decoded as that stimulus. The vertical axis of the matrix gives the presented stimulus (i), and the horizontal axis gives the decoded stimulus (j). The matrix element at position (i,j) gives the probability that stimulus i is decoded as stimulus j. If j=i, the stimulus is decoded correctly, otherwise, the stimulus is decoded incorrectly. Put simply, elements on the diagonal indicate correct decoding; elements off the diagonal indicate confusion.

In this task, an array of stimuli is presented, specifically, stimuli containing natural sounds, and the extent to which the stimuli can be distinguished from each other, based on the responses of the SG cells and/or encoders, is measured.

A training set is obtained in order to build response distributions (the "training set"), and another set is obtained to be decoded to calculate the confusion matrix (the "test set").

To decode the responses in the test set, one determines which of the stimuli $s_j$ was the most likely to produce it. That is, one determines the stimulus $s_j$ for which $p(r|s_j)$ was maximal. Bayes theorem is used, which states that $p(s_j|r)=p(r|s_j)p(s_j)/p(r)$, where $p(s_j|r)$ is the probability that the stimulus $s_j$ was present, given a particular response r; $p(r|s_j)$ is the probability of obtaining a particular response r given the stimulus $s_j$; and $p(s_j)$ is the probability that the stimulus $s_j$ was present. $p(s_j)$ is set equal for all stimuli in this experiment and so, by Bayes Theorem, $p(s|r_j)$ is maximized when $p(r|s_j)$ is maximized. When $p(s_j)$ is uniform, as it is here, this method of finding the most likely stimulus given a response is referred to as maximum likelihood decoding (Kass et al. 2005; Pandarinath et al. 2010; Jacobs et al. 2009). For each presentation of stimulus $s_i$ that resulted in a response r that was decoded as the stimulus $s_j$, the entry at position (i,j) in the confusion matrix is incremented.

To build the response distributions needed for the decoding calculations used to make the confusion matrices (i.e., to specify $p(r|s_j)$ for any response r), the procedure is as follows. The response r is taken to be the spike train spanning 100 ms after stimulus onset and binned with 5 ms bins; this is the appropriate timescale in particular for speech sounds. The spike generation process is assumed to be an inhomogeneous Poisson process, and the probability $p(r|s_j)$ for the entire 100 ms response is calculated as the product of the probabilities for each 5 ms bin. The probability assigned to each bin is determined by Poisson statistics, based on the average training set response in this bin to the stimulus $s_j$. Specifically, if the number of spikes of the response r in this bin is n, and the average number of spikes in the training set responses in this bin is h, then the probability assigned to this bin is $(h^n/n!)\exp(-h)$. The product of these probabilities, one for each bin, specifies the response distributions for the decoding calculations used to make the confusion matrices.

Once the confusion matrices are calculated, overall performance in the forced choice visual discrimination task is quantified by "fraction correct", which is the fraction of times over the whole task that the decoded responses correctly identified the stimuli. The fraction correct is the mean of the diagonal of the confusion matrix.

Given this procedure, at east sets of analyses may be performed. For each one, the responses from the normal SG cells are used for the training set and a different set of responses is used for the test set, as outlined below.

(1) The first set may include or consist of responses from normal SG cells. This is done to obtain the fraction correct produced by normal SG cells.

(2) The second set may include or consist of the responses from the encoders (in various embodiments, the responses from the encoders, as indicated throughout this document and that of the original application, may be streams of electrical pulses, e.g., spanning 100 ms after stimulus presentation, and binned with 5 ms, as are the normal SG responses). In other embodiments, other suitable durations and bin times may be used.

Responses from this test set yield a measure of how well the encoders perform, given the response distributions of the normal SG cells. The basis for this is that the brain is built to interpret the responses of the normal SG cells (i.e., the naturally encoded responses.) When responses from the encoder are used as a test set, one obtains a measure of how well the brain would do with our proxy of the normal SG responses (our proxy of the SG code).

(3) The third set may include or consist of responses from the SG cells of a deaf animal or human driven by the encoders and output generator (e.g., driving a ChR2 based transducer), where the responses are of the same duration and bin size as above. This set provides a measure of how well the encoder performs after its output has been passed through to real tissue.

As shown in Example 8 of the Retinal Application, the encoder's performance in the forced choice discrimination task was 98.75% of the normal retina's performance, and complete system's performance, that is, the performance of an embodiment of the encoder, output generator, and related transducer was 80% of the normal retina's performance. Thus, for various embodiments, when tested in vitro or in an animal or human model, the performance of the auditory prosthesis in the forced choice discrimination task, as measured by "fraction correct", should be similar, that is at least about 35%, 50%, 60%, 70%, 80%, 90%, 95%, 99%, or 100% of the performance of the normal SG cells, or better than the normal SG cells, measured as described above. Moreover, these performance levels may be obtained with response time scales for the prosthetic 200 which are substantially the same as those found in an unimpaired subject. That is, in some embodiments, the prosthetic 200 in jumping impaired cochlear hair cells introduces a lag time of which is of suitably short duration. For example, in some embodiments the lag time is less than a factor of 5, 4, 3, 2, 1, 0.5, 0.1, (e.g., a factor in the range of 0.1-5 or any subrange thereof) or less times the signaling time exhibited by a normal subject.

Other Embodiments

Although several examples have been provided, it is to be understood that numerous variations are within the scope of the present disclosure. For example, although prostheses for auditory and motor applications have been provided, it is to be understood that the devices and techniques may be applied in a variety of additional settings. Further, although various examples of cell and tissue types have been provided (e.g. jumping from SMA to SMN or muscle, or jumping from an audio stimulus to SG), it is to be understood that other types of cells, tissue, etc. may be used. In general, the devices and techniques described herein may be adapted to a wide variety of cases where a prosthetic is required which operates as a proxy for signaling cells which have suffered some form of gap or impairment.

Tables 2-6 summarize a number of applications where the devices and techniques described herein may be used to restore or improve function. For each application, the tables set forth a region of the nervous system that is impaired, the resulting body parts that have diminished function, the cause of the injury or impairment, the region from which activity is read (corresponding to A in FIG. 1B), the region which is stimulated (corresponding to C in FIG. 1B), and the connection that us bypassed or "jumped." It is to be understood that the examples provided in the tables are in no way exhaustive.

TABLE 2

| Region of CNS That is Impaired | Body Part(s) That Have Diminished Function | Cause of Impairment | Input Region | Output Region | Connection |
|---|---|---|---|---|---|
| dorsal column tract aka posterior/dorsal horn (dorsal white column) fibers | impairment of procrioception, vibratory sensation/loss of deep tendon reflex (skin, joints,tendons);impaired two-point discrimination; figure writing; detection of size, shape, weight, and texture of objects; ability to detect the direction and speed of a moving stimulus on the skin; Waxman 68,55,56,57; Ropper and Samuels Ch 9 | tabes dorsalis (sensory ataxia); stereoanethesia (impaired graphesia and tactile localization); multiple sclerosis, vitamin B12 deficiency, HIV and human T-lymphotropic virus infection; Waxman 68; Ropper and Samuels ch 9; | dorsal root or: right before lesioned part of tract; Adams' and Victor's Neurology Ch 9 | (medial lemniscus) VPL thalamus or: right after lesioned part of tract; Waxman 57; http://www.ncbi.nlm.nih.gov/books/NBK11142/ | primary somatic sensory cortex (postcentral gyrus); Waxman, 56; http://www.ncbi.nlm.nih.gov/books/NBK11142/;; Brazis 287 |
| Spinothalamic Tract (ventrolateral column fibers) | (skin) loss of pain/temp sensation below/opposite side of lesion (ipsilateral lower extremities);motor weakness same side of lesion; ipsilateral side of face; neuronal hyperexcitability at injury/above the injury; pain below the injury | Syringomyelia; stroke; trauma; Waxman 66, 68; Kierman 77; http://www.ncbi.nlm.nih.gov/pmc/articles/PMC2170182/?tool=pubmed; http://www.ncbi.nlm.nih.gov/pubmed/14663044 | posterior root ganglion axons aka dorsal root or: right before lesioned part of tract; Snell 142; Waxman Ch 5 Sec III; | (medial lemniscus) VPL thalamus or: right after lesioned part of tract; Waxman 56; http://www.ncbi.nlm.nih.gov/books/NBK10967/; Brazis 287 | primary somatic sensory cortex (postcentral gyrus); Waxman 57; http://www.ncbi.nlm.nih.gov/books/NBK10967/; Brazis 287 |

TABLE 2-continued

| Region of CNS That is Impaired | Body Part(s) That Have Diminished Function | Cause of Impairment | Input Region | Output Region | Connection |
|---|---|---|---|---|---|
| | level (central pain); Waxman 56;http://www.ncbi.nlm.nih.gov/books/NBK10967/ ; Brazis 370; http://www.ncbi.nlm.nih.gov/pmc/articles/PMC2170182/?tool=pubmed;www.ncbi.nlm.nih.gov/pubmed/14663044 | | | | |
| Dorsal Spinocerebellar tract aka posterior spinocerebellar tract (lateral column fibers) | muscle spindles/Golgi tendon organs,touch+pressure receptors via nucleus dorsalis; ipsilateral lower extremities (vibration/positional sensory functions) ;severe ophthalmoplegia (paralysis of eye muscles), bilateral ptosis(eyelid), areflexia, and moderate cerebellar ataxia; irresponsive pupils; facial nerve palsy; Waxman 56; Brazis 370 ; http://cornell.worldcat.org/title/position-and-vibration-sensations-functions-of-the-dorsal-spinocerebellar-tracts/ocic/114767304&referer=brief_results; http://www.ncbi.nlm.nih.gov/pubmed/7876862 | X-Chromosome Linked Copper Malabsorption ; Hereditory Spastic Paresis;spinocerebellar ataxia (atrophy + demyelinization of fibers); Miller Fisher-Guillain Barre Overlap Syndrome; http://onlinelibrary.wiley.com/doi/10.1002/ana.410050609/abstract; http://www.sciencedirect.com/science/article/pii/0022510X9490037X; (SCA 2) http://www.ncbi.nlm.nih.gov/pubmed/14507334 ; http://www.ncbi.nlm.nih.gov/pubmed/7876862 | posterior root aka dorsal root (posterior gray column) or: right before lesioned part of tract; Snell 147 | precerebellar nuclei or: right after lesioned part of tract; Kierman 93; http://www.dartmouth.edu/~rswenson/NeuroSci/chapter_7A.html | inferior cerebellar peduncle; Kierman 72,167; 2) http://www.accessmedicine.com/content.aspx?aID=5272458&searchStr=cerebellar+peduncle#5272458 |
| Ventral Spinocerebellar tract aka anterior spinocerebellar tract | 1)muscle spindles/Golgi tendon organs (sensory input from skeletal muscle) ,touch+pressure receptors; 2) severe ophthalmoplegia (paralysis of eye muscles), bilateral ptosis(eyelid), areflexia, and moderate cerebellar ataxia; | a) Miller Fisher-Guillain Barre Overlap Syndrome; b) Friedrich's Syndrome (heredo-ataxia); a) http://www.ncbi.nlm.nih.gov/pubmed/7876862; b) http://www.ncbi.nlm.nih.gov/pubmed?term=%22ventral%20spinocerebellar%20tract%22%20atax | dorsal root ganglion axons (posterior gray column) or: right before lesioned part of tract; Snell 146 | precerebellar nuclei or: right after lesioned part of tract; Kierman 93 ;http://www.dartmouth.edu/~rswenson/NeuroSci/chapter_7A.html | superior cerebellar peduncle ((to cerebellar cortex) ; Kierman 72; http://www.accessmedicine.com/content.aspx?aID=5272458&searchStr=cerebellar+peduncle#5272458 |

TABLE 2-continued

| Region of CNS That is Impaired | Body Part(s) That Have Diminished Function | Cause of Impairment | Input Region | Output Region | Connection |
|---|---|---|---|---|---|
| | irresponsive pupils; 3) facial nerve palsy; optic nerve degeneration; 1) Waxman 56; http://www.blac kwellpublishing. com/patestas/c hapters/10.pdf; 2) http://www.ncbi .nlm.nih.gov/pu bmed/7876862; 3) http://www.ncbi .nlm.nih.gov/pu bmed?term=%2 2ventral%20spin ocerebellar%20t ract%22%20atax ia | ia | | | |
| Spinoreticular Tract (lateral column) | deep somatic structures ; lack of triggering of noxious inhibitory controls (nonpainful but noxious stimuli) ; hemianalgesia; Waxman 56; http://www.ncbi .nlm.nih.gov/pu bmed?term=Diff use%20noxious %20inhibitory% 20controls%20in %20man.%20Inv olvement%20of %20the%20spin oreticular%20tra ct | Wallenberg's Syndrome; http://www.ncbi .nlm.nih.gov/pu bmed?term=Diff use%20noxious %20inhibitory% 20controls%20in %20man.%20Inv olvement%20of %20the%20spin oreticular%20tra ct | posterior root ganglion axons or: right before lesioned part of tract; Snell 150 | reticular formation (precerebellar nucleus) or: right after lesioned part of tract; http://www.acc essmedicine.co m/content.aspx aID=5271956& searchStr=spino cerebellar+tract s#5271956. Kierman 72; http://www.scie ncedirect.com/s cience/article/pi i/S03010082980 00483 | Thalamus; cerebral cortex; http://www.blac kwellpublishing. com/patestas/c hapters/10.pdf ; Latash 171 (Neurophysiolog ical basis of movement) |
| Corticopontocer ebellar Pathway (pontocerebellar tract; pontine nuclei; part of cerebellum) | myelin decay (white matter tracts); dysarthria (mouth), hemiparesis of one side, nystagmus (involuntary eye twitching); http://www.ncbi .nlm.nih.gov/pu bmed/18172629 | ataxic neurodegerenati ve diseases (hereditary spinocerebellar ataxia); multiple system atrophy (MSA); late-onset cerebellar cortical atrophy (LCCA); stroke; http://www.ncbi .nlm.nih.gov/pu bmed/18172629 http://www.ncbi .nlm.nih.gov/pu bmed/8342190 | nerve cells in frontal/parietal/ temporal/occipit al lobes of cerebral cortex or: right before lesioned part of tract; Snell 226-227 | pontine nuclei or: right after lesioned part of tract; Snell 226-229 | cerebellar cortex; Snell 226-229 |
| cerebro-olivocerebellar tract fibers | involuntary eye twitching (rebound nystagmus), wasting of small muscles of both hands, spastic paralysis of both legs, dysdiadochokine sia (lack of coordination)of upper limbs, ocular dysmetria; | olivocerebellar atrophy; cerebellar ataxia; http://www.ncbi .nlm.nih.gov/pu bmed/7931442; | nerve cells in frontal/parietal/ temporal/occipit al lobes of cerebral cortex or: right before lesioned part of tract; Snell 226 | inferior olivary nuclei or: right after lesioned part of tract; Snell 229 | cerebellar cortex; Snell 229 |

TABLE 2-continued

| Region of CNS That is Impaired | Body Part(s) That Have Diminished Function | Cause of Impairment | Input Region | Output Region | Connection |
|---|---|---|---|---|---|
| | http://www.ncbi.nlm.nih.gov/pubmed/7931442; | | | | |

TABLE 3

| Region of CNS That is Impaired | Body Part(s) That Have Diminished Function | Cause of Impairment | Input Region | Output Region | Connection |
|---|---|---|---|---|---|
| Ventromedial medulla | ipsilateral hypoglossal palsy (tongue paralysis); contralateral hemiplegia/hemiparesis; loss of sense of temp/pain (skin); Kierman 108; http://www.sciencedirect.com/science/article/pii/S105230579880027X; http://www.nejm.org/doi/full/10.1056/ENEJMicm020058; http://www.sciencedirect.com/science/article/pii/S105230579880027X; http://archneur.ama-assn.org/cgi/reprint/57/4/478 | Kierman 108,109; Head and neck surgery--otolaryngology By Byron J. Bailey p119; Jonas T. Johnson, Shawn D. Newlands; http://stroke.ahajournals.org/content/26/4/702.full; http://www.sciencedirect.com/science/article/pii/S0306452206003836; http://www.sciencedirect.com/science/article/pii/S105230579880027X | 1) dorsomedial hypothalamus neurons 2) midbrain periaqueductal gray (for rostral ventromedial medulla); 1) http://www.ncbi.nlm.nih.gov/pubmed/21196160 2) http://www.annualreviews.org/doi/abs/10.1146/annurev.ne.14.030191.001251 | medial lemniscus; Waxman 86 | inferior cerebellar peduncle (cerebral cortex); Waxman 86; Smith et al 45 |
| Lateral Medulla | 1. ipsilateral palate paralysis (roof of mouth); vocal cord paralysis; loss of pain/heat sensation on same side of face/opposite of body (skin?); loss of facial sweating (skin); 2. diminishment pf pharyngeal reflex (pharynx); limb weakness; Kierman 108,110; http://keur.eldoc.ub.rug.nl/FILES/wetenschappers/1/478/478.pdf ; http://stroke.ahajournals.org/content/28/4/809.abstract; Brazis 369; http://www.springerlink.com/content/f348889372351m38/ | Wallenberg's syndrome "Lateral Medullary Syndrome" (vertigo, ataxia); caused by inferior artery occlusion; trauma; stroke; Kierman 107, 108,109; http://www.springerlink.com/content/p76622184414hr60/ ; Waxman Ch 7 Clinical Illustration 7-1 | solitary tract nucleus (NTS) ; http://www.sciencedirect.com/science/article/pii/S1053811908001001X; http://onlinelibrary.wiley.com/doi/10.1002/cne.21105/abstract | medial lemniscus; Waxman 86 | inferior cerebellar peduncle (cerebral cortex); Waxman 86; Smith et al 45 |

TABLE 3-continued

| Region of CNS That is Impaired | Body Part(s) That Have Diminished Function | Cause of Impairment | Input Region | Output Region | Connection |
|---|---|---|---|---|---|
| Lateral Medulla | ipsilateral plate paralysis; vocal cord paralysis; loss of pain/heat stroke; on ipsilateral side of face/contralateral side of body (face-arm-trunk-legs); Kierman 108; http://www.ncbi.nlm.nih.gov/pmc/articles/PMC2170182/pdf/v065p00255.pdf ; http://jnnp.bmj.com/content/65/2/255.abstract | Avellis' syndrome; dysphagia; acute Kierman 108; http://www.ncbi.nlm.nih.gov/pubmed/8821503; http://www.ncbi.nlm.nih.gov/pubmed/21576937 | solitary tract nucleus (NTS); http://www.sciencedirect.com/science/article/pii/S1053811908001001X; http://onlinelibrary.wiley.com/doi/10.1002/cne.21105/abstract | medial lemniscus; Waxman 86 | inferior cerebellar peduncle (cerebral cortex); Waxman 86; Smith et al 45 |
| pons (corticospinal fibers/descending fibers) | ipsilateral LMN paralysis (face);contralateral hemiplesia; or: undamaged fibers before the lesion; Kierman 108 ; localization in clinical neurology by braxis/masdeu/biller 291,553 ; http://content.karger.com/ProdukteDB/produkte.asp?Aktion=ShowPDF&ArtikelNr=000116965&Ausgabe=234289&ProduktNr=223840&filename=000116965.pdf | Millard Gubler's syndrome; trauma; Kierman 108;localization in clinical neurology by braxis/masdeu/biller 291; http://content.karger.com/ProdukteDB/produkte.asp?Aktion=ShowPDF&ArtikelNr=000116965&Ausgabe=234289&ProduktNr=223840&filename=000116965.pdf | midbrain basis pedunculi or: undamaged part of fibers right after lesion; Kierman 101 | pontine nuclei; Kierman 101; Smith 56 | middle cerebellar peduncle (cerebellum); Kierrman 101 Wxman 89; Brazis et al 357 |
| dorsal pons (pontine tegmentum) | ipsilateral LMN facial paralysis (face); ipsilateral conjugate gaze paralysis (eyes); contralateral hemiparesis; blepharospasm (eyelid closing); motor tract damage; facial nerve damage; failure to abduct eye; Kierman 108,110; http://keur.eldoc.ub.rug.nl/FILES/wetenschappers/1/478/478.pdf ; http://stroke.ahajournals.org/content/28/4/809.abstract; Brazis 369; http://www.springerlink.com/content/f348889372351m38/ | Foville's Syndrome (lower dorsal pontine syndrome) ; Wall-Eyed Internuclear Ohtalmoplegia WEBINO syndrome (caused by stroke; multiple schlerosis; infections); stroke ; Kierman 108,110,111,121 ; http://stroke.ahajournals.org/content/11/1/84.abstract; Brazis et al 359; http://www.springerlink.com/content/f348889372351m38/ ; http://www.ncbi.nlm.nih.gov/pubmed/21729278 | pontine nuclei; Kierman 101; Smith 56 | middle cerebellar peduncle (cerebellum); Kierrman 101; Waxman 89; Brazis et al 357 | |

TABLE 3-continued

| Region of CNS That is Impaired | Body Part(s) That Have Diminished Function | Cause of Impairment | Input Region | Output Region | Connection |
|---|---|---|---|---|---|
| ventral pons (pontocerebellar fibers) | ipsilateral abducens nerve palsy (VI nerve, lateral rectus muscle of eye); contralateral hemiparesis (1/2 of body);upper motor neuron quadriplegia, paralysis of lower cranial nerves, bilateral paresis of horizontal gaze; Kierman 108 ; http://stroke.ah ajournals.org/co ntent/28/4/809. abstract; http://www.ncbi .nlm.nih.gov/pu bmed/12119076 | Raymond's Syndrome; Locked in Syndrome (caused by Stroke or traumatic brain injury due to obstructed basilar artery); lesion; anarthria (speech loss); quadriplegia; Kierman 108; http://www.spri ngerlink.com.pr oxy.library.corne ll.edu/content/7 4n878271705ru 11/; http://www.ncbi .nlm.nih.gov/pu bmed/12119076 | pontine nuclei neurons' axons (cerebral cortex) or: undamaged portion of pontocerebellar fibers right before the the lesion; Kierman 101; Smith 56 | middle cerebellar peduncle (cerebellum) or: undamaged portion of pontocerebellar fibers right after Kierman 101 Waxman 89; Brazis et al. 357 | |
| cerebral peduncle ( pyramidal fibers/fascicle of cranial nerve 3 ) | ipsilateral oculomotor abducens nerve palsy (pupil of eyes); contralateral hemiparesis;con tralateral hemiplegia (face); tremor + involuntary movements (red nucleus destruction); heaviness of limbs/difficulty using hand/slurred speech (disorder of articulatory movements of tongue + oris muscles); unwanted hand activity ; Kierman 108; http://onlinelibr ary.wiley.com/d oi/10.1002/mds. 10084/full; http://www.ncbi .nlm.nih.gov/pu bmed/18826349 ; http://www.brig hamandwomens .org/Departmen ts_and_Services /neurology/servi ces/NeuroOphth amology/Images /SelectedPublica tions/Strabismu s.pdf; http://www.scie ncedirect.com/s cience/article/pi i/S08872171019 00034 ; Brazis 361, 362; Theime's | Benedikt's Syndrome; Weber's syndrome (i.e. Ventral Midbrain Syndrome); peduncular hallucinosis (for vascular lesions); stroke ; Dysarthia (Clumsy Hand Syndrome); Kierman 108; http://www.harr isonspractice.co m/practice/ub/v iew/Harrisons% 20Practice/1416 11/all/Double+30V ision;http://ww w.ncbi.nlm.nih.g ov/pubmed/188 26349 http://www.brig hamandwomens .org/Departmen is and Services /neurology/servi ces/NeuroOphth amology/Images /SelectedPublica tions/Strabismu s.pdf ; Brazis 361, 362; http://www.ncbi .nlm.nih.gov/pu bmed?term=Gel ler%20TJ%2C%2 OBellur%20SN.% 20Peduncular%2 Ohallucinosis%3 A%20magnetic% 20resonance%2 Oimaging%20co nfirmation%20of %20mesenceph alic%20infarctio n%20during%20l ife.%20Ann%20 | lenticular nucleus aka corpus striatum externus (olfactory lobe fasciculi) or: unlesioned part Stricker 416 | Pontine Nuclei; Kahle and Frotscher 166; Morris and McMurich 871 | medulla oblongata; Morris and McMurrich 876 |

TABLE 3-continued

| Region of CNS That is Impaired | Body Part(s) That Have Diminished Function | Cause of Impairment | Input Region | Output Region | Connection |
|---|---|---|---|---|---|
| | Anatomic Basis of Neurologic Diagnosis Atlas 226; http://www.ncbi.nlm.nih.gov/pmc/articles/PMC1073816/ | Neurol%201987%3B21%3A602%E2%80%93604; http://www.ncbi.nlm.nih.gov/pubmed/17621531 http://www.sciencedirect.com/science/article/pii/S1052305708001535;http://www.ncbi.nlm.nih.gov/pmc/articles/PMC1073816/ | | | |
| dorsal midbrain (superior colliculus, pretectal area, posterior commisure etc) | conjugate upward gaze paralysis w-o paralysis of convergence; abnormalities of pupil response (eyes); paralysis of vertical gaze; ipsilateral head tilt; vertical diplopia (downwards/contralesional gaze); Kierman 108, 121; http://www.ncbi.nlm.nih.gov/pubmed/20182210; http://www.sciencedirect.com/science/article/pii/S0303846709002406; | Parinaud's syndrome (aka dorsal midbrain syndrome, pretectal syndrome, Sylvian aqueduct syndrome) ; tumor pressure on posterior commissure/pretectal area/superior colliculi ; trauma; stroke; Horner's Syndrome; miningitis/herpes zoster/syphilis (connective tissue infections); Kierman 108,121; http://stroke.ahajournals.org/content/12/2/251.abstract; http://www.ncbi.nlm.nih.gov/pubmed/20182210; http://www.sciencedirect.com/science/article/pii/S0303846709002406 | occipital cortex (corticotectal fibers); Kierman 102-103 | a) caudal nucleus ; b) lateral geniculate nucleus (LGN); http://www.ncbi.nlm.nih.gov/pubmed/21344403 | a) Thalamus; b) primary visual cortex; Westerlain 248; http://www.ncbi.nlm.nih.gov/pubmed/21344403 |
| Middle cerebellar peduncle aka branchial pontis | ipsilateral facial paralysis (face), impaired facial sensation (skin); paralysis of conjugate gaze to the side of the lesion (eyes); contralateral sense loss of temp/pain; deafness (ears) ; tinnitus (ears); middle cerebellar peduncle infarction (nystagmus, speech difficulty, ataxia of limbs/trunk); inner ear | anterior inferior cerebellar artery (AICA) injury; lateral inferior pontine syndrome; ataxia; aneurysm; stroke ; cardiac embolism; trauma; localization in clinical neurology by braxis/masdeu/biller 553; http://www.ncbi.nlm.nih.gov/pubmed/21748288; http://www.ncbi.nlm.nih.gov/pubmed/20572906 | pontocerebellar fibers (from pontine nuclei neurons' axons); Kierman 101 | Cerebellum; Young et al 105 | |

TABLE 3-continued

| Region of CNS That is Impaired | Body Part(s) That Have Diminished Function | Cause of Impairment | Input Region | Output Region | Connection |
|---|---|---|---|---|---|
| | dysfunction (vertigo/tinnitus /bilateral hearing loss); (anterior inferior cerebellar artery-related) localization in clinical neurology by braxis/masdeu/ biller 553; http://stroke.ah ajournals.org/co ntent/33/12/28 07.full; http://brain.oxf ordjournals.org/ content/113/1/1 39.abstract?ijke y=60fl63a9bdc3 3efe496746bc1e ffc8f9c4e1dd9c &keytype2=tf_ip secsha; http://www.ncbi .nlm.nih.gov/pu bmed/20572906 ;http://www.nc bi.nlm.nih.gov/p ubmed/1983486 5;http://www.n cbi.nlm.nih.gov/ pubmed/197971 77 | ;http://www.nc bi.nlm.nih.gov/p ubmed/1983486 5; http://www.ncbi .nlm.nih.gov/pu bmed/21631321 | | | |

TABLE 4

| Region of CNS That is Impaired | Body Part(s) That Have Diminished Function | Cause of Impairment | Input Region | Output Region | Connection |
|---|---|---|---|---|---|
| C2 root | impairment of respiratory function; Currrent Treatment and Diagnostic in Orthopedics ch 13 | tumors ; http://www.ncbi .nlm.nih.gov/pu bmed/21123996 | dorsal rami/afferent fibers from dorsal root ganglion or: right before the lesioned part of the root; Kiernan 62; Waxman 48-49 | spinothalamic tract, spinomesenceph alic tract; http://www.ncbi .nlm.nih.gov/pu bmed/2358537 (for cervical enlargement projections in general); Thieme Color Atlas of the Human Body, p558- 559(reference for cervical enlargement components) | periaquaductal grey (midbrain); thalamus; http://www.ncbi .nlm.nih.gov/pu bmed/2358537 (for cervical enlargement projections in general); Thieme Color Atlas of the Human Body, p558- 559(reference for cervical enlargement components) |
| C3 root | jaw/neck; infrahyoids, semispinalis capitis and cervicis, longissimus capitis and cervicis, | sensory disturbances; muscle paresis; (trauma) subluxation of spinal axis; degenerative motor root C3 | dorsal rami/afferent fibers from dorsal root ganglion or: right before the lesioned part of the root; | 1) Ventral Spinocerebellar Tract; 2) spinothalamic tract, spinomesenceph alic tract; 1) | 1) cerebellum 2) periaquaductal grey (midbrain); thalamus; 1) http://www.ncbi .nlm.nih.gov/pu |

TABLE 4-continued

| Region of CNS That is Impaired | Body Part(s) That Have Diminished Function | Cause of Impairment | Input Region | Output Region | Connection |
|---|---|---|---|---|---|
|  | intertransversarii, rotatores, multifidi muscle paresis;diapragm weakness/anterior trunk; Brazis et al 93; waxman 51 | compression (ventral osseus compression); Brazis et al 93; http://www.ncbi.nlm.nih.gov/pubmed/21120549 | Kierman 62; Waxman 48-49 | http://www.ncbi.nlm.nih.gov/pubmed/14337566?dopt=Abstract&holding=npg; 2)http://www.ncbi.nlm.nih.gov/pubmed/2358537 (for cervical enlargement projections in general); Thieme Color Atlas of the Human Body, p558-559(reference for cervical enlargement components) | bmed/14337566?dopt=Abstract&holding=npg ; http://www.ncbi.nlm.nih.gov/pubmed/2358537 (for cervical enlargement projections in general); Thieme Color Atlas of the Human Body, p558-559(reference for cervical enlargement components); 2) http://www.sciencedirect.com/science/article/pii/S0006899398004120 (for cuneate nucleus in general); Thieme Color Atlas of Human Anatomy Vol III - Nervous System and Sensory Organs 341 (for cuneate nucleus-thalamus-cortex connection) Thieme Color Atlas of the Human Body, p558-559(reference for cervical enlargement components) |
| C4 root | scalene/levator scapulae/trapezoid (shoulder)/rhomboid muscles paresis; diaphragmic paresis + pulmonary difficulty;diaphragm weakness/anterior trunk; Brazis et al 93; waxman 51 | muscle paresis; degenerative motor root C4 compression (ventral osseus compression); trauma/birth injury;trauma; compression by a ganglion; Brazis et al 93; http://www.ncbi.nlm.nih.gov/pubmed/21120549 | dorsal rami/afferent fibers from dorsal root ganglion or: right before the lesioned part of the root; Kierman 62; Waxman 48-49 | spinothalamic tract, spinomesencephalic tract; 1) http://www.ncbi.nlm.nih.gov/pubmed/14337566?dopt=Abstract&holding=npg; 2)http://www.ncbi.nlm.nih.gov/pubmed/2358537 (for cervical enlargement projections in general); Thieme Color Atlas of the Human Body, p558-559(reference for cervical enlargement components) | 1) periaqueductal grey (midbrain); thalamus 2) postcentral cyrus (from cuneate nucleus to thalamus); 1) http://www.ncbi.nlm.nih.gov/pubmed/14337566?dopt=Abstract&holding=npg ; http://www.ncbi.nlm.nih.gov/pubmed/2358537 (for cervical enlargement projections in general); Thieme Color Atlas of the Human Body, p558-559(reference for cervical enlargement components); 2) |

TABLE 4-continued

| Region of CNS That is Impaired | Body Part(s) That Have Diminished Function | Cause of Impairment | Input Region | Output Region | Connection |
|---|---|---|---|---|---|
| | | | | | http://www.sciencedirect.com/science/article/pii/S0006899398004120 (for cuneate nucleus in general); Thieme Color Atlas of Human Anatomy Vol III - Nervous System and Sensory Organs 341 (for cuneate nucleus-thalamus-cortex connection) Thieme Color Atlas of the Human Body, p558-559(reference for cervical enlargement components) |
| C5 root | neck/shoulder/upper anterior arm pain; sensory disturbances on lateral arm; muscle paresis for levator scapulae, rhomboids, serratus anterior, supraspinatus, infraspinatus, deltoid, biceps, brachioradialis; diaphragmatic paresis (if damaged C5 fibers reach phrenic nerve); biceps/brachioradialis (poor reflex); hemidiaphragmic paresis +30 pulmonary difficulty; radicular pain (suprascaular region of root);deltoid weakness; Brazis et al 93; http://www.josonline.org/abstracts/v18n3/356.html; Waxman 51 | depressed bicets reflex; depressed brachioradialis reflex;cervical spondylosis(degenerative tissue of cervical vertebrae); cervical radiculopathy; post-operative (decompression/spinal cord fusion) C5 palsy following anterior decompression and spinal fusion for cervical degenerative diseases; contributing pre-existing asymptomatic damage of the anterior horn cells at C3-C4 and C4-C5 levels (motor weakness); upper brachial plexus palsies; high velocity impact (like football) causing nerve avulsion; trauma; compression by a ganglion; Brazis et al 93; Frank 1031; http://www.josonline.org/abstracts/v18n3/356.html; http://www.ncbi.nlm.nih.gov/pubmed/20461418; | dorsal rami/afferent fibers from dorsal root ganglion or: right before the lesioned part of the root; Kierman 62; Waxman 48-49 | spinothalamic tract, spinomesencephalic tract; http://www.ncbi.nlm.nih.gov/pubmed/2358537 (for cervical enlargement projections in general); Thieme Color Atlas of the Human Body, p558-559(reference for cervical enlargement components); http://www.sciencedirect.com/science/article/pii/S0006899398004120 | 1) periaquaductal grey (midbrain); thalamus 2) postcentral cyrus (from cuneate nucleus to thalamus); http://www.ncbi.nlm.nih.gov/pubmed/2358537 (for cervical enlargement projections in general); Thieme Color Atlas of the Human Body, p558-559(reference for cervical enlargement components) |

TABLE 4-continued

| Region of CNS That is Impaired | Body Part(s) That Have Diminished Function | Cause of Impairment | Input Region | Output Region | Connection |
|---|---|---|---|---|---|
| | | http://www.sciencedirect.com/science/article/pii/S0365023100 05101; http://www.ncbi.nlm.nih.gov/pmc/articles/PMC2504282/ ; Thieme Atlas of Neurology 767-768 | | | |
| C6 root | lateral/dorsal forearm pain; paresis of muscles (erratus anterior, biceps, pronator teres, flexor carpi radialis, brachioradialis, extensor carpi radialis longus, supinator, and extensor carpi radialis brevis); depressed biceps/brachioradialis reflex; radicular pain (posterior deltoid region);biceps weakness; Brazis et al 93; http://www.josonline.org/abstracts/v18n3/356.html; Waxman 51 | hyperflexia (if corticalspinal tract is damage); depressed biceps/brachiora dialis reflex (due to compression of C5-6 vertebral level); cervical spondylosis(deg enerative tissue of cervical vertebrae); cervical radiculopathy;up per brachial plexus palsies; ipsilateral root injury;C5-C6 unilateral facet dislocation (vertebrae injury due to trauma like car accident); high velocity impact (football) causing nerve avulsion; trauma; compression by a ganglion; Brazis et al 93; Frank 1031; http://www.josonline.org/abstracts/v18n3/356.html; http://www.sciencedirect.com/science/article/pii/S0365023100 05101; Johnson Ch 29 (Principles of Critical Care); http://www.ncbi.nlm.nih.gov/pmc/articles/PMC2504282/ | dorsal rami/afferent fibers from dorsal root ganglion or: right before the lesioned part of the root; Kiernan 62; Waxman 48-49 | 1) n/a 2) Spinothalamic tract (dorsal column); 1) n/a 2) http://www.sciencedirect.com/science/article/pii/S000689939800 4120 | 1) Ventrolateral Medulla (VLM) Nuclei; Solitary tract nucleus (NTS), lateral reticular nucleus (LRt), caudal/rostral ventrolateral medulla; 2) postcentral cyrus (from cuneate nucleus to thalamus); 1) http://www.sciencedirect.com/science/article/pii/S1566070202000346; 2) http://www.sciencedirect.com/science/article/pii/S000689939800 4120 (for cuneate nucleus in general); Thieme Color Atlas of Human Anatomy Vol III - Nervous System and Sensory Organs 341 (for cuneate nucleus-thalamus-cortex connection) |
| C7 root | pain in dorsal forearm/deep breast; sensory disturbances on 3rd/4th digits; paresis of muscles ( serratus anterior, pectoralis major, latissimus dorsi, pronator teres, flexor carpi | compression due to disc herniation at C6-7 vertebral level; cervical osteoarthritis;ce rvical spondylosis (degenerative tissue of cervical vertebrae); cervical radiculopathy | dorsal rami/afferent fibers from dorsal root ganglion or: right before the lesioned part of the root; Kiernan 62; Waxman 48-49 | 1) n/a | 1) Ventrolateral Medulla (VLM) Nuclei; Solitary tract nucleus (NTS), lateral reticular nucleus (LRt), caudal/rostral ventrolateral medulla; 1) http://www.sciencedirect.com/s |

TABLE 4-continued

| Region of CNS That is Impaired | Body Part(s) That Have Diminished Function | Cause of Impairment | Input Region | Output Region | Connection |
|---|---|---|---|---|---|
| | radialis, triceps, extensor carpi radialis longus, extensor carpi brevis,extensor digitorum); triceps reflex depressed; pseudomyotonia of hand (difficulty in opening b/c of cervical osteoarthritis); radicular pain (interscapular region) ;triceps weakness; Brazis et al 94; http://www.joso nline.org/abstrac ts/v18n3/356.ht ml; Waxman 51 | ;upper brachial plexus palsies; trauma; Brazis et al 94; Frank 1031; http://www.joso nline.org/abstrac ts/v18n3/356.ht ml; http://www.scie ncedirect.com/s cience/article/pii /S036350231000 5101 ; Thieme Atlas of Neurology 768 | | | cience/article/pii /S156607020200 0346; |
| C8 root | pain in the medial arm/forearm; fifth digit; medial forearm/hand; paresis of muscles (flexor digitorum superficialis, flexor pollicis longus, flexor digitorum profundus Ito IV, pronator quadratus, abductor pollicis brevis, opponens pollicis, flexor pollicis brevis, lumbricals, flexor carpi ulnaris, abductor digiti minimi, opponens digiti minimi, flexor digiti minimi, all interossei, adductor pollicis, extensor digiti minimi, extensor carpi ulnaris, abductor pollicis longus, extensor pollicis longus and brevis, and extensor indicis); depressed finger flexor reflex; razis et al 94; http://www.joso nline.org/abstrac ts/v18n3/356.ht ml; Thieme Atlas of Neurology 779 radicular pain (interscapular/sc apular region of nerve root) ; motor deficit in hand muscles | compression due to disc herniation at C7-T1 vertebral level; ipsilateral Horner Syndrome; cervical radiculopathy; nerve root blockage ; trauma/birth trauma; tumor of lung apex; ly,phomatous infiltration; pressure lesion at elbow; all traumatic palsy (from a blow/knife/glass at the wrist or elbow fractures); delayed nerve palsy (ages after an elbow fracture/dislocat ion etc +vagus deformity) ; arthrosis; Brazis et al 94; http://www.joso nline.org/abstrac ts/v18n3/356.ht ml; Thieme Atlas of Neurology 753, 759, 776 | dorsal rami/afferent fibers from dorsal root ganglion or: right before the lesioned part of the root; Kierman 62; Waxman 48-49 | 1) n/a | 1) Ventrolateral Medulla (VLM) Nuclei; Solitary tract nucleus (NTS), lateral reticular nucleus (LRt), caudal/rostral ventrolateral medulla; 1) http://www.scie ncedirect.com/s cience/article/pii /S156607020200 0346 |

TABLE 4-continued

| Region of CNS That is Impaired | Body Part(s) That Have Diminished Function | Cause of Impairment | Input Region | Output Region | Connection |
|---|---|---|---|---|---|
| T3 root | decreased sensation of skin (dermatome); radicular pain/low back pain/paralysis; Brazis et al 94; http://www.ncbi.nlm.nih.gov/pubmed/17149734 | arachnoid calcifications (caused by trauma); myelography, subarachnoid hemorrhage, spinal anesthesia; http://www.ncbi.nlm.nih.gov/pubmed/17149734 | dorsal rami/afferent fibers from dorsal root ganglion or: right before the lesioned part of the root; Kiernan 62; Waxman 48-49 | Dorsal Spinocerebellar Tract; http://www.ncbi.nlm.nih.gov/pubmed/14337566?dopt=Abstract&holding=npg | cerebellum (cerebellar cortex); http://www.ncbi.nlm.nih.gov/pubmed/14337566?dopt=Abstract&holding=npg |
| T4 root | decreased sensation of skin (dermatome); numbness in body/both legs; bladder/bowel dysfunction; progressive weakness of bilateral lower extremities; radicular pain/low back pain/paralysis; Brazis et al 94; http://www.ncbi.nlm.nih.gov/pubmed/19398862; http://www.ncbi.nlm.nih.gov/pubmed/17149734 | intramedullary tumor (spinal metastasis); arachnoid calcifications (caused by trauma); subarachnoid hemorrhage; http://www.ncbi.nlm.nih.gov/pubmed/19398862; http://www.ncbi.nlm.nih.gov/pubmed/17149734 | dorsal rami/afferent fibers from dorsal root ganglion or: right before the lesioned part of the root; Kiernan 62; Waxman 48-49 | Dorsal Spinocerebellar Tract; http://www.ncbi.nlm.nih.gov/pubmed/14337566?dopt=Abstract&holding=npg | cerebellum (cerebellar cortex); http://www.ncbi.nlm.nih.gov/pubmed/14337566?dopt=Abstract&holding=npg |
| T5 root | decreased sensation of skin (dermatome); Brazis et al 94; http://www.ncbi.nlm.nih.gov/pubmed/8133999 | T5 nerve root fistula; trauma (particularly head injuries or penetrating damage to the spine); http://www.ncbi.nlm.nih.gov/pubmed/8133999 | dorsal rami/afferent fibers from dorsal root ganglion or: right before the lesioned part of the root; Kiernan 62; Waxman 48-49 | Dorsal Spinocerebellar Tract; http://www.ncbi.nlm.nih.gov/pubmed/14337566?dopt=Abstract&holding=npg | cerebellum (cerebellar cortex); http://www.ncbi.nlm.nih.gov/pubmed/14337566?dopt=Abstract&holding=npg |
| T6 root | decreased sensation of skin (dermatome); gait control difficulty; tactile hypaethesia below T6; Brazis et al 94; http://www.sciencedirect.com/science/article/pii/S0967586806002384 | schwannoma (nerve sheath tumor); http://www.sciencedirect.com/science/article/pii/S0967586806002384 | dorsal rami/afferent fibers from dorsal root ganglion or: right before the lesioned part of the root; Kiernan 62; Waxman 48-49 | Dorsal Spinocerebellar Tract; http://www.ncbi.nlm.nih.gov/pubmed/14337566?dopt=Abstract&holding=npg | cerebellum (cerebellar cortex); http://www.ncbi.nlm.nih.gov/pubmed/14337566?dopt=Abstract&holding=npg |
| T7 root | no movement in lower extremities; gait control difficulty; thermic/algic hypaethesia below T7; http://www.ncbi.nlm.nih.gov/pubmed/18662744; | T6-T7 injury (trauma); schwannoma (tumor of nerve sheath); arachnoid calcifications w/ possible arachnoid ossification + nerve root | dorsal rami/afferent fibers from dorsal root ganglion or: right before the lesioned part of the root; Kiernan 62; Waxman 48-49 | Dorsal Spinocerebellar Tract; http://www.ncbi.nlm.nih.gov/pubmed/14337566?dopt=Abstract&holding=npg | cerebellum (cerebellar cortex); http://www.ncbi.nlm.nih.gov/pubmed/14337566?dopt=Abstract&holding=npg |

TABLE 4-continued

| Region of CNS That is Impaired | Body Part(s) That Have Diminished Function | Cause of Impairment | Input Region | Output Region | Connection |
|---|---|---|---|---|---|
| | http://www.sciencedirect.com/science/article/pii/S0967586806002384 | compression (caused by trauma or interspinal tumor); myelography, subarachnoid hemorrhage, spinal anethesia; http://www.ncbi.nlm.nih.gov/pubmed/18662744; O'Rahilly et al ch 41; http://www.sciencedirect.com/science/article/pii/S0967586806002384; http://www.ncbi.nlm.nih.gov/pubmed/17149734 | | | |
| T8 root | no movement in lower extremities; complete motor/sensory deficit; lack of sphincter/sexual function and control;radicular pain/low back pain/paralysis; http://www.ncbi.nlm.nih.gov/pubmed/18662744; http://www.ncbi.nlm.nih.gov/pubmed/17149734 | T6-T7 injury (trauma) ; T7-T8 injury (trauma); T7 level injury (trauma); http://www.ncbi.nlm.nih.gov/pubmed/18662744; O'Rahilly et al ch 41. | dorsal rami/afferent fibers from dorsal root ganglion or: right before the lesioned part of the root; Kierman 62; Waxman 48-49 | Dorsal Spinocerebellar Tract; http://www.ncbi.nlm.nih.gov/pubmed/14337566?dopt=Abstract&holding=npg | cerebellum (cerebellar cortex); http://www.ncbi.nlm.nih.gov/pubmed/14337566?dopt=Abstract&holding=npg |
| T9 root | lack of sphincter/sexual function and control; http://www.ncbi.nlm.nih.gov/pubmed/18662745 | T7-T8 injury(trauma); arachnoid calcifications w/ possible arachnoid ossification + nerve root compression (caused by trauma); myelography, subarachnoid hemorrhage, spinal anesthesia; http://www.ncbi.nlm.nih.gov/pubmed/18662744; http://www.ncbi.nlm.nih.gov/pubmed/17149734; O'Rahilly et al ch 41 | dorsal rami/afferent fibers from dorsal root ganglion or: right before the lesioned part of the root; Kierman 62; Waxman 48-49 | Dorsal Spinocerebellar Tract; http://www.ncbi.nlm.nih.gov/pubmed/14337566?dopt=Abstract&holding=npg | cerebellum (cerebellar cortex); http://www.ncbi.nlm.nih.gov/pubmed/14337566?dopt=Abstract&holding=npg |
| T10 root | bilateral abdominal muscle paresis; trace movements/hypoethesia (partial | T9 Injury (trauma); tumor pressure; http://www.ncbi.nlm.nih.gov/pubmed/18662744 | dorsal rami/afferent fibers from dorsal root ganglion or: right before | Dorsal Spinocerebellar Tract; http://www.ncbi.nlm.nih.gov/pubmed/14337566 | cerebellum (cerebellar cortex); http://www.ncbi.nlm.nih.gov/pubmed/14337566 |

TABLE 4-continued

| Region of CNS That is Impaired | Body Part(s) That Have Diminished Function | Cause of Impairment | Input Region | Output Region | Connection |
|---|---|---|---|---|---|
| | loss of sensation) in lower extremities; lack of sphincter/sexual function or control; muscle spasms; Brazis et al 94; http://www.ncbi.nlm.nih.gov/pubmed/18662745 | ; O'Rahilly et al ch 41. | the lesioned part of the root; Kierman 62; Waxman 48-49 | ?dopt=Abstract& holding=npg | ?dopt=Abstract& holding=npg |
| T11 root | excessive protrusion of abdomen (when inspiring); bilateral abdominal muscle paresis; Brazis et al 94 | lateral disc herniation causing compression on root; http://www.ncbi.nlm.nih.gov/pubmed/18090072 | dorsal rami/afferent fibers from dorsal root ganglion or: right before the lesioned part of the root; Kierman 62; Waxman 48-49 | Dorsal Spinocerebellar Tract; http://www.ncbi.nlm.nih.gov/pubmed/14337566 ?dopt=Abstract& holding=npg | cerebellum (cerebellar cortex); http://www.ncbi.nlm.nih.gov/pubmed/14337566 ?dopt=Abstract& holding=npg |
| T12 root | excessive protrusion of abdomen (when inspiring); bilateral abdominal muscle paresis; motor weakness in lower extremity; hyperalgesia below L1; Brazis et al 94; http://www.ncbi.nlm.nih.gov/pubmed/19350043 | trauma; nerve root avulsion; associated syringomyelia; tumor pressure ; lateral disc herniation causing compression on root; http://www.ncbi.nlm.nih.gov/pubmed/19350043 ; http://www.ncbi.nlm.nih.gov/pubmed/18090072 | dorsal rami/afferent fibers from dorsal root ganglion or: right before the lesioned part of the root; Kierman 62; Waxman 48-49 | Dorsal Spinocerebellar Tract; http://www.ncbi.nlm.nih.gov/pubmed/14337566 ?dopt=Abstract& holding=npg | cerebellum (cerebellar cortex); http://www.ncbi.nlm.nih.gov/pubmed/14337566 ?dopt=Abstract& holding=npg |
| L1 root | tibial nerve; cremasteric reflex; inguinal region (groin/lower lateral regions of abdomen); lower abdominal paresis (internal oblique, transversus abdominis); Waxman 62; Brazis et al 95 | herniation of L5/S1 disc; lateral disc herniation causing compression on root; (L5/S1) http://www.neuroanatomy.wisc.edu/SClinic/Radiculo/Radiculopathy.htm; http://www.ncbi.nlm.nih.gov/pubmed/18090072 | dorsal rami/afferent fibers from dorsal root ganglion or: right before the lesioned part of the root; Kierman 62; Waxman 48-49 | Dorsal Spinocerebellar Tract ; Waxman Ch 5; http://www.ncbi.nlm.nih.gov/pubmed/14337566 ?dopt=Abstract& holding=npg | cerebellum (cerebellar cortex); Waxman Ch 5; http://www.ncbi.nlm.nih.gov/pubmed/14337566 ?dopt=Abstract& holding=npg |
| L2 root | anterior thigh sensory disturbances; paresis of body parts:pectineus (thigh adduction, flexion, and eversion), iliopsoas (thigh flexion), sartorius (thigh flexion and eversion), quadriceps (leg extension), and thigh adductors; depression of cremasteric reflex (of L2) ; | meralgia parethetica due to compression of nerve; lumbar radiculopathy; lumbar disc herniation into preganglionic region of the nerve root; spinal stetosis; trauma; (meralgia parethetica/lumbar)http://www.ncbi.nlm.nih.gov/pubmed/21294431; | dorsal rami/afferent fibers from dorsal root ganglion or: right before the lesioned part of the root; Kierman 62; Waxman 48-49 | Dorsal Spinocerebellar Tract; Waxman Ch 5; http://www.ncbi.nlm.nih.gov/pubmed/14337566 ?dopt=Abstract& holding=npg | cerebellum (cerebellar cortex); Waxman Ch 5; http://www.ncbi.nlm.nih.gov/pubmed/14337566 ?dopt=Abstract& holding=npg |

TABLE 4-continued

| Region of CNS That is Impaired | Body Part(s) That Have Diminished Function | Cause of Impairment | Input Region | Output Region | Connection |
|---|---|---|---|---|---|
| | | Brazis et al 95; http://www.ncbi.nlm.nih.gov/pubmed/20431433; | | | |
| L3 root | lower anterior thigh, medial knee; paresis in pectineus (thigh adduction, flexion, and eversion), iliopsoas (thigh flexion), sartorius (thigh flexion and eversion), quadriceps (leg extension), and thigh adductors; depressed reflex of L2-L4 (patellar reflex) ; S1 root @dorsal lateral portion of L3 level;quadricepts femoris weakness (knee); Brazis et al 95; http://www.josonline.org/pdf/v18i3p367.pdf; Waxman 51 | arachnoidal/dural defect; physical trauma leading to herniation of nerve root; nerve root entrapment in pseudominingocele; lumbar spondylolysis; (archnoidal/dural/pseudominingocele/lumbar spondylolysis) http://www.josonline.org/pdf/v18i3p367.pdf; | dorsal rami/afferent fibers from dorsal root ganglion or: right before the lesioned part of the root; Kiernan 62; Waxman 48-49 | Dorsal Spinocerebellar Tract; http://www.ncbi.nlm.nih.gov/pubmed/14337566?dopt=Abstract&holding=npg | cerebellum (cerebellar cortex); http://www.ncbi.nlm.nih.gov/pubmed/14337566?dopt=Abstract&holding=npg |
| L4 root | pain in lower back/buttock/anterlateral thigh/anterior leg; sensory disturbances of knee/medial leg; paresis in muscles of leg/feet - quadriceps (leg extension)sartorius (thigh flexion and eversion),tibialis anterior (foot dorsiflexion and inversion); depressed patellar reflex; quadriceps femoris weakness (knee); Brazis et al 95; http://www.josonline.org/pdf/v18i3p367.pdf; http://www.josonline.org/abstracts/v18n3/352.html; Waxman 51 | lumbar spondylolysis;invading tumors involving ala of sacrum infringing on nerve root; tumor excision; neurogenic hypertrophy (tibialis anterior muscle) due to excessive activity; Brazis et al 95; http://www.josonline.org/pdf/v18i3p367.pdf; http://www.josonline.org/abstracts/v18n3/352.html; | dorsal rami/afferent fibers from dorsal root ganglion or: right before the lesioned part of the root; Kiernan 62; Waxman 48-49 | Dorsal Spinocerebellar Tract; http://www.ncbi.nlm.nih.gov/pubmed/14337566?dopt=Abstract&holding=npg | cerebellum (cerebellar cortex); http://www.ncbi.nlm.nih.gov/pubmed/14337566?dopt=Abstract&holding=npg |
| S1 root | pain in lower back, buttock, lateral thigh,calf; sensory disturbance of little toe, lateral | post-osteotomy surgery complications; post-dissection joining of S1,S2 leaving nerve | dorsal rami/afferent fibers from dorsal root ganglion or: right before | VPL Thalamus ; Young et al 142 | Primary Sensory Cortex (postcentral gyrus); Young et al 138-142; Ropper and |

TABLE 4-continued

| Region of CNS That is Impaired | Body Part(s) That Have Diminished Function | Cause of Impairment | Input Region | Output Region | Connection |
|---|---|---|---|---|---|
| | foot, most of the sole of the foot; paresis in knee/hip/feet - gluteus maximus (hip extension), biceps femoris (knee flexion), gastrocnemius + soleus (plantar flexion of foot), flexor hallucis longus (plantar flexion of foot and terminal phalanx of great toe), flexor digitorum longus (plantar flexion of foot and all toes except the large toe), all of the small muscles of the foot, extensor digitorum brevis (extension of large toe + three medial toes); S1-S2 (depressed achilles reflex) ;gastrocnemius weakness; lower extremity parethesia ; Brazis et al 96; Waxman 51; http://www.ncbi.nlm.nih.gov/pubmed/17341045 ; | roots at risk of tumor invasion; clear cell sarcoma (tumor arising from S1 nerve root); http://www.josonline.org/abstracts/v18n3/352.html | the lesioned part of the root; Kiernan 62; Waxman 48-49 | | Samuels Ch 9 |
| S2 root | lower limb/bowel/bladder functions; Sensory disturbances for calf, posterior thigh, buttock, perianal region; Brazis et al 96; http://www.josonline.org/abstracts/v18n3/352.html | iatrogenic injury during surgery; post-dissection joining of S1,S2 leaving nerve roots at risk of tumor invasion; (surgery/tumors) http://www.josonline.org/abstracts/v18n3/352.html; http://www.ncbi.nlm.nih.gov/pubmed/21500136 | dorsal rami/afferent fibers from dorsal root ganglion or: right before the lesioned part of the root; Kiernan 62; Waxman 48-49 | VPL Thalamus; Young et al 142 | Primary Sensory Cortex (postcentral gyrus); Young et al 138-142; Ropper and Samuels Ch 9 |
| S3 root | Chronic lower back pain; impaired Sphincter activity; Sensory disturbances for calf, posterior thigh, buttock, perianal region; Brazis et al 96; http://www.ncbi.nlm.nih.gov/pubmed/21286446 ; http://www.ncbi.nlm.nih.gov/pubmed/18034793 ; | invasion by tumor; sciatica (nerve root compression); Tarlov Cysts; Cauda Equina Syndrome(due to spinal cord compression by drug-induced loculation); (Invasion by tumor)http://www.josonline.org/abstracts/v18n3/352.html; http://www.ncbi.nlm.nih.gov/pubmed/21500136 | dorsal rami/afferent fibers from dorsal root ganglion or: right before the lesioned part of the root; Kiernan 62; Waxman 48-49 | VPL Thalamus ; Young et al 142 | Primary Sensory Cortex (cerebrum) ; Young et al 138-142 |

TABLE 4-continued

| Region of CNS That is Impaired | Body Part(s) That Have Diminished Function | Cause of Impairment | Input Region | Output Region | Connection |
|---|---|---|---|---|---|
| | | ;http://www.ncbi.nlm.nih.gov/pubmed/21286446 | | | |

TABLE 5

| Region of CNS That is Impaired | Body Part(s) That Have Diminished Function | Cause of Impairment | Input Region | Output Region | Connection |
|---|---|---|---|---|---|
| small center lesions (spinothalamic tract decussating fibers) | i)loss of pain/temp sensibilities in the segment w/lesion (Decussating fibers in the ventral white commisure) - anethesia for shoulders/upper limbs;muscle wasting in upper limbs; ii)anterior horn atrophy/paresis/areflexia; i)Waxman 68; ii) Brazis et al 105 | a) Syringomyelia b) Chiari Type I, II, Dandy Walker Malformations, traumatic paraplegia, spinal trauma, spinal cord tumors, arachnoiditis, myelitis; a) Waxman 66, 68; Kiernan 77 b)Brazis et al 105 | posterior root ganglion axons aka dorsal root or: right before lesioned part of tract; Snell 142; Waxman Ch 5 Sec III; | ventral posterior nucleus of thalamus or: right after lesioned part of tract; Kiernan 292; Waxman 56,57,58 | cerebral cortex (primary sensory cortex or SI area); Young et al 149-150; |
| posterior/lateral columns in upper spinal cord (dorsal column-medial lemniscus pathway) aka dorsal cornu or lateral cornu/horn | cervical cord; thoratic cord; lumbar cord degeneration; parethesia in feet/hands; Dorsal column dysfunction (spine/skin sensation); Brazis et al 106; Tsementzis 208 | a) Posterolateral Column Disease (lack of B12); AIDS; HTLV-1; tropical spastix paraperesis; cervical spondylosis (chronic disk degeneration); b)sensory ataxia/loss of proprioception and vibration sense/bilateral spasticity/hyper reflexia c) trauma; a)Bravis 106; http://www.accessmedicine.com/content.aspx?aID=2319519&searchStr=cervical+spine+disease; b) Differential diagnosis in neurology and neurosurgery: a clinician's pocket guide By S. A. Tsementzis 208 c) http://www.ncbi.nlm.nih.gov/pubmed/3096488 | dorsal root or: right before lesioned part of tract; Adams' and Victor's Neurology Ch 9 | dorsal column nuclei (cuneate nuclei) or: right after lesioned part of tract; http://www.google.com/url?sa=t&source=web&cd=1&ved=0CBoQFjAA&url=http%3A%2F%2Fwww.biomed.cas.cz%2Fphysiolres%2Fpdf%2F53%2520Suppl%25201%2F53_5125.pdf&ei=etY2TuP9LlrZgQf_sdnsDA&usg=AFQjCNG_02zJSpiKjPhNyxivc-VBjOpWww | primary sensory cortex (SI area); Kiernan 292; Young et al 149-150; http://www.ncbi.nlm.nih.gov/pubmed/3096488; http://www.ncbi.nlm.nih.gov/pubmed/8899636; http://www.google.com/url?sa=t&source=web&cd=1&ved=0CBoQFjAA&url=http%3A%2F%2Fwww.biomed.cas.cz%2Fphysiolres%2Fpdf%2F53%2520Suppl%25201%2F53_5125.pdf&ei=etY2TuP9LlrZgQf_sdnsDA&usg=AFQjCNG_02zJSpiKjPhNyxivc-VBjOpWww |
| complete transection of spinal cord (transverse | a) Vertebral Tenderness (percussion?) b) inhibition of | 1) traumatic spine injuries (stabbing/gunfire/diving into a | undamaged parts of all ascending tracts from below the | undamaged parts of all ascending tracts from above the | neocortex (cingulate gyrus) for sensory ascending tracts; |

TABLE 5-continued

| Region of CNS That is Impaired | Body Part(s) That Have Diminished Function | Cause of Impairment | Input Region | Output Region | Connection |
|---|---|---|---|---|---|
| myelopathy) | reflex anywhere in the cord below the lesion; Spincter disturbance; back/radicular pain c)Tactile stimulus above lesion d) all motor/sensory functions below the level of lesion; a) Current Diagnosis and Treatment (Keith Stone) ch 35 b)Total Transverse Lesions of the Spinal Cord c)Adam's and Victor's Neurology, ch44: http://www.acc essmedicine.co m/content.aspx ?aID=3640629& searchStr=transv erse+myelitis d) Brazis et al 103 | shallow pool), tumor (e.g., metastatic carcinoma, lymphoma), multiple sclerosis, ,vascular disorders,spinal epidural hematoma (usually secondary to anticoagulants) or abscess, paraneoplastic myelopathy, autoimmune disorders, herniated intervertebral disc, and parainfectious or postvaccinal syndromes 2) herpes simplex, influenza, Epstein-Barr virus), immunisations (smallpox, influenza) and intoxication (baclofen, penicillins, lead); ; Systemic Lupus; 3)tetraplegia (if upper cervical cord transection); paraplegia iif transection between the cervical and lumbosacral enlargements; 1. Brazis et al 103; Jeffrey et al Arch Neurol. 1993 May;50(5):532-5. ; 2)http://ard. bmj .com/content/5 9/2/120.abstrac t 3) Kierman 76 | lesion; all descending tracts from above the lesion ; Brazis et al 103 | lesion; all descending tracts from below the lesion ; Brazis et al 103 | Kierman 289 |
| Dorsal Root ganglion (aka posterior root ganglion) | elecated touch-pressure sensation thresholds (dorsal column/spinoce rebellar tract dysfunction due to demyelination);i ncreased sense of pain(hyperalgesi a)/pain due to | ALS, HIV/AIDS, tumor (particularly Small Cell Lung Cancer SCLC); Vitamin B6 intoxication (ex: body building regimen,PMS treatment); chemotherapy drugs especially platinum based agents (ex: | peripheral nervous system's afferent/sensory fibers or: part of dorsal Human root right before the lesioned ganglion ; Brazis et al 89 | dorsal (posterior) horn cells or: part of the dorsal root right after the lesioned ganglion; Color Atlas of Textboom of Human Anatomy: Nervous system and Sensory | medulla oblongata; cerebellum; Color Atlas of Textboom of Anatomy: Nervous system and Sensory Organs 50-56 |

TABLE 5-continued

| Region of CNS That is Impaired | Body Part(s) That Have Diminished Function | Cause of Impairment | Input Region | Output Region | Connection |
|---|---|---|---|---|---|
| | negligible stimulus(allodynia) ; gait impairment, autonomic system impairment; (vitamin overdose) loss of tendon reflex, progressive sensory ataxia; bilnk reflex abnormalities; (ALS) http://www.ncbi.nlm.nih.gov/pubmed/17929040; http://www.ncbi.nlm.nih.gov/pubmed/20628092; http://jn.physiology.org/content/84/2/798.full; http://pn.bmj.com/content/10/6/326.full | Ciplatin, carboplatin, oxaliplatin etc) ; Guillian Barre, Miller Fisher Sundrome, opthalmoplegia; rheumatoid arthritis, Sjogren's syndrome, Epstein-barr, measles, varicella zoster; (ALS) http://www.ncbi.nlm.nih.gov/pubmed/17929040; http://www.ncbi.nlm.nih.gov/pubmed/20628092; http://pn.bmj.com/content/10/6/326.full | | Organs 50-56 | |
| Anterior horn (aka anterior column/ventral horn) | upper motor neurons (any striated muscle); progressive weakness of the bulbar, limb/thoracic/abdominal musculature; upper motor neuron spasticity/paresis; Brazis et al 107-109; http://jnnp.bmj.com/content/74/9/1250.abstract; Tsementzis 209 | Spinal muscular Atrophies; ALS (degeneration of upper motor neurons/Charcois Lou Gehrig's); progressive bulbar palsy, progressive muscular atrophy (lower motor syndrome), primary lateral sclerosis (upper motor syndrome),astro cytosis; trauma; stroke (ipsilateral cerebral peduncular atrophy); non-traumatic cardiac arrest (due to spinal cord ischemia) ; Brazis et al 109, http://jnnp.bmj.com/content/74/9/1250.abstract; http://www.ncbi.nlm.nih.gov/pubmed/18024577; http://www.ncbi.nlm.nih.gov/pubmed/7884198 | ventral root (sensory nerves); Bonica's Management of Pain 1497; http://onlinelibrary.wiley.com/doi/10.1002/cne.901790304/pdf | dorsal horn/columns; Bonica's Management of Pain 1497; http://onlinelibrary.wiley.com/doi/10.1002/cne.901790304/pdf | Color Atlas of Textboom of Human Anatomy: Nervous system and Sensory Organs 50 |
| Upper Cervical Cord (cervicomedullary junction injuries or | contralateral upper extremity paresis and ipsilateral lower extremity | Cruciate Paralysis (caused by traumatic injuries mostly); | | medial lemniscus ; Smith et al 34-35 | cerebral hemisphere (sensory-motor cortex) ; cerebellum; |

TABLE 5-continued

| Region of CNS That is Impaired | Body Part(s) That Have Diminished Function | Cause of Impairment | Input Region | Output Region | Connection |
|---|---|---|---|---|---|
| malformations) | paresis; lower extremity weakness (muscles proximal to the lesion) ; facial/limb hypethesia; Brazis et al 112; http://www.upt odate.com/cont ents/anatomy-and-localization-of-spinal-cord-disorders/abstra ct/18 | http://www.upt odate.com/cont ents/anatomy-and-localization-of-spinal-cord-disorders/a bstra ct/18 | | | Smith et al 34-35; http://www.ncbi .nlm.nih.gov/pu bmed/19793979 |
| Complete hemisection of spinal cord (dorsal column) | ipsilateral zone of cutaneous anethesia in the segment of the lesion (due to undecussated afferent fibers that had already entered the spinal cord); loss of propioceptive/vi bratory/2-pt discrimination sense below the lesion (dorsal column damage); spastic weakness at level of lesion; loss of temperature/pai n sensation below the level (decussated spinothalamic tract fibers damage); Waxman 68; Brazis et al 105 | Brown-Sequard Syndrome (stab/gunshot wounds) ;syringomelia (loss of pain/temperatur e sensation at multiple levels); spinal cord tumor; hematomyelia (hemorrhage into the spinal cord) ; Waxman 68 ; Brazis et al 105 | below the lesion in dorsal column; below the lesion in spinothalamic tract; below the lesion for any afferent fibers; Waxman 68 | dorsal column nuclei (cuneate nuclei); http://www.goo gle.com/url?sa=t &source=web&c d=1&ved=0CBo QFjAA&url=http %3A%2F%2Fww w.biomed.cas.cz %2Fphysiolres% 2Fpdf%2F53%25 20Suppl%25201 %2F53_5125.pdf &ei=etY2TuP9Llr ZgQf_sdnsDA&u sg=AFQjCNG_02 zJSpiKjPhNyxivc-VBjOpWww | cerebral cortex (primary sensory cortex or SI area) ; Kierman 292; Young et al 149-150; http://www.ncbi .nlm.nih.gov/pu bmed/3096488 ; http://www.ncbi .nlm.nih.gov/pu bmed/8899636; http://www.goo gle.com/url?sa=t &source=web&c d=1&ved=0CBo QFjAA&url=http %3A%2F%2Fww w.biomed.cas.cz %2Fphysiolres% 2Fpdf%2F53%25 20Suppl%25201 %2F53_5125.pdf &ei=etY2TuP9Llr ZgQf_sdnsDA&u sg=AFQjCNG_02 zJSpiKjPh Nyxivc-VBjOpWww |
| myelin sheaths of axons (PNS + CNS) | axon degeneration; failure of signal transmission; slowing of nerve conduction; motor weakness, paraparesis, paresthesia (numbing of skin) , diplopia (double vision), nystagmus (involuntary eye movement), tremor, ataxia, impairment of deep sensation, and bladder dysfunction; blindness, tremor; Young et al 13; Waxman 24,38,302; | Multiple Sclerosis; Acute inflammatory demyelinating polyneuropathy (AIDP), Guillain Barre; traumatic brain injury (for oligodendrite injuries)+ subsequent degeneration of white matter tracts; Miller-Fischer Syndrome; copper deficiency ; Waxman 302; DeLisa et al 899; Adams and Victor's Neurology Ch 36 ; http://www.ncbi .nlm.nih.gov/pu | node of ranvier before the lesion; Waxman 25 | next node of ranvier after the lesion in the direction of the action potential pathway; Waxman 25 | |

TABLE 5-continued

| Region of CNS That is Impaired | Body Part(s) That Have Diminished Function | Cause of Impairment | Input Region | Output Region | Connection |
|---|---|---|---|---|---|
| | Adams and Victor's Neurology Ch 36 | bmed/21669255 ; http://www.ncbi .nlm.nih.gov/pu bmed/21631649 ; http://www.ncbi .nlm.nih.gov/pu bmed/20685220 | | | |

TABLE 6

| Region of CNS That is Impaired | Input Region | Output Region | Connection |
|---|---|---|---|
| I Olfactory Nerve | bipolar cells in olfactory epithelium (cilia at surface of epithelium in superior nasal concha + upper ⅓ of nasal septum) or: part of normal nerve before lesion; Young et al 270; http://www.blac kwellpublishing. com/patestas/c hapters/15.pdf | Olfactory Bulb (glomeruli) or: part of normal nerve right after the lesion; Young et al 262; http://www.ncbi .nlm.nih.gov/pu bmed/21704681 | Olfactory association cortex (frontal lobe); Kierman 262-263 |
| VIII Vestibular (Vestibulocochle ar Nerve) | vestibular ganglion aka scarpa's ganglion (hair cells of ampullary crests in semicircular ducts/maculae of saccule and utricle) or: part of normal nerve Young et al 272; Shumway-Cook 69 | Vestibular nuclei or: part of normal nerve right after the lesion; Young et al 262; Kierman 335; Shumway-Cook 69 | Vestibulocerebel lum aka flocculonodar lobe of cerebellum; Kierman 335 |
| VIII Cochlear (Vestibulocochle ar Nerve) | otic ganglion (auriculotempor al nerve supplying paratoid gland) or: part of normal nerve before lesion; Schuenke et al 150; Young et al 272; | Cochlear nuclei (second-order neurons) or: part of normal nerve right after the lesion; Young et al 262, 161 | primary auditory area of cerebral cortex (aka superior temporal gyrus); Kierman 326 |
| V Trigeminal Nerve | trigeminal ganglion aka sublingual/Langl ey's ganglion ( free nerve ends in muscous mouth membrane aka oral mucosa; anterior scalp/face; free nerve endings in tympanic | spinal trigeminal nucleus (caudal); principal trigeminal nucleus or: part of normal nerve right after the lesion; Young et al 270; | VPM Thalamus (then to primary sensory cortex); Waxman ch 8 |

TABLE 6-continued

| Region of CNS That is Impaired | Input Region | Output Region | Connection |
|---|---|---|---|
| | membrane, supratentorial meninges); submandibular ganglion or: part of normal nerve before lesion; Young et al 270; http://www.ncbi .nlm.nih.gov/pu bmed/13886632 ; http://www.scie ncedirect.com/s cience/article/pi i/S03043940100 03423 | | |
| VII Facial Nerve | Pterygopaline ganglion; submandibular ganglion; geniculate ganglion (taste buds in anterior ⅔ of mouth) or: part of normal nerve (chorda tympani fibers) before lesion; Young et al 237,271; Waxman 113 | Solitary Nucleus or: part of normal nerve right after the lesion; Waxman 113-115 | ipsilateral cerebral cortex (primary gustatory cortex) ; Kierman 131; Young et al 193-194 |
| IX Glossopharynge al Nerve | otic ganglion (auriculotempor al nerve supplying paratoid gland) or: part of normal nerve before lesion; Young et al. 237; Waxman 257; Snell 403,405 | Solitary Nucleus (taste + chemoreceptor and baroreceptor reflexes)/Spinal Trigeminal Nucleus (general sensations) or: part of normal nerve right after the lesion; Young et al 269; Brazis et al 325 | cerebral cortex (post central gyrus) ; Kierman 214,215 |
| X Vagus Nerve | cardiac ganglion; bronchial ganglion; pulmonary ganglion; enteric ganglion;intestin al ganglion; | Solitary nucleus (inferior ganglion)/Spinal trigeminal nucleus(superior ) or: part of | cerebral cortex; Young et al 253 |

TABLE 6-continued

| Region of CNS That is Impaired | Input Region | Output Region | Connection |
|---|---|---|---|
| | proximal colon ganglion or: part of normal nerve before lesion; Young et al 237; http://www.ncbi.nlm.nih.gov/pubmed/2435865; http://www.ncbi.nlm.nih.gov/pubmed/8946336 | normal nerve right after the lesion; Young et al 273; | |

Although in the examples above we describe and build encoders in a modular fashion with a specific set of algorithmic steps, it is evident that algorithms or devices with substantially similar input/output relationships can be built with different steps, or in a non-modular fashion, for example, by combining any two or three of the steps in to a single computational unit, such as an artificial neural network.

Given the encoders of the present disclosure, it is possible to generate data sets, without the collection of physiological data, that can be used, for example, to develop parameters for alternate spatiotemporal transformations, or to train a neural net, to produce identical or similar output using methods that are well known in the art. The explicit description of the encoders thus enables the development of prosthetics, as well as other devices, such as, but not limited to, bionics (e.g., devices providing supranormal capability) and robotics (e.g., artificial sensing systems).

The scope of the present invention is not limited by what has been specifically shown and described herein. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form (e.g., non-transitory media). For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein the term "light" and related terms (e.g. "optical") are to be understood to include electromagnetic radiation both within and outside of the visible spectrum, including, for example, ultraviolet and infrared radiation.

As used herein the term "sound" and related terms (e.g. "audio") are to be understood to include vibratory waves in any medium (e.g., gas, fluid, liquid, solid, etc.) both within and outside of the spectrum audible to humans, including, for example, ultrasonic frequencies.

All definitions, as defined and used herein, should be understood to control over dictionary definitions, definitions in documents incorporated by reference, and/or ordinary meanings of the defined terms.

Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

REFERENCES

Ahuja A, Dorn J, Caspi A, McMahon M, Dagnelie G, Dacruz L, Stanga P, Humayun M, Greenberg R (2010) Blind subjects implanted with the Argus II retinal prosthesis are able to improve performance in a spatial-motor task. Br J Ophthalmol.

Arenkiel et al., In vivo light-induced activation of neural circuitry in transgenic mice expressing channelrhodopsin-2. *Neuron* (2007) 54(2): 205-18.

Ausubel et al., Current Protocols in Molecular Biology, John Wiley & Sons, New York, 1989

Averback and Lee (2006) Effects of Noise Correlations on Information Encoding and Decoding, *J Neurophysiol* 95: 3633-3644

Bach, M et al (2008) Visual evoked potential-based acuity assessment in normal vision, artificially degraded vision, and in patients. Br J Ophthalmol 92:396-403

Barnstable et al., Thy-1 antigen: a ganglion cell specific marker in rodent retina. *Neuroscience* (1984) 11(4): 847-55.

Bi A, Cui J, Ma Y-P, Olshevskaya E, Pu M, Dizhoor A M, Pan Z-H (2006) Ectopic expression of a microbial-type rhodopsin restores visual responses in mice with photoreceptor degeneration. Neuron 50:23-33.

Bomash I, Roudi Y, Nirenberg S. (2010) A virtual retina that works on a broad array of stimuli including natural scenes: A tool to simplify the problem of population coding. *Society for Neuroscience*. Program No. 891.5.

Bookstein R et al (1990) Promoter deletion and loss of retinoblastoma gene expression in human prostate carcinoma. Proc. Nati. Acad. Sci. USA 87 (19):7762-7766

Brown C J et al. (2000) The Relationship Between EAP and EABR Thresholds and Levels Used to Program the Nucleus 24 Speech Processor: Data from Adults. Ear and Hearing 21(2): 151-163

Busskamp V, et al (2010) Genetic reactivation of cone photoreceptors restores visual responses in retinitis pigmentosa. Science 329:413-417.

Cai et al. (2010) Gene delivery to mitotic and postmitotic photoreceptors via compacted DNA nanoparticles results in improved phenotype in a mouse model of retinitis pigmentosa. *FASEB J.* 24: 1178-1191.

Campagnola L, Wang H, Zylka M J. (2008) Fiber-coupled light-emitting diode for localized photostimulation of neurons expressing channelrhodopsin-2. Journal of Neuroscience Methods. 169:27-33.

Cardin J A, et al (2010) Targeted optogenetic stimulation and recording of neurons in vivo using cell-type-specific expression of Channelrhodopsin-2. Nat Protoc 5(2): 247-54.

Cescon C, et al (2006) Non-invasive characterization of single motor unit electromyographic and mechanomyographic activities in the biceps brachii muscle. J Electromyogr Kinesiol 16(1):17-24. Epub 2005 Aug. 19.

Chader G J, Weiland J, Humayun M S (2009) Artificial vision: needs, functioning, and testing of a retinal electronic prosthesis. Prog Brain Res 175:317-332.

Chen X, et al (2001) HSV amplicon-mediated neurotrophin-3 expression protects murine spiral ganglion neurons from cisplatin-induced damage. Mol Ther. 3(6):958-63.

Chiappa, K. (1997) Evoked Responses in Clinical Medicine, Third Edition, Lippincott-Raven Chichilnisky E J. (2001) A simple white noise analysis of neuronal light responses. *Network* 12(2): 199-213

Chestek C A et al, (2009) Low-Power Wireless Neural Recording System for Freely Moving Primates IEEE TRANSACTIONS ON NEURAL SYSTEMS AND REHABILITATION ENGINEERING, 17(4): 268-275

Chopdar A, Chakravarthy U, Verma D (2003) Age related macular degeneration. BMJ 326:485-488.

Cover T and Thomas J. (2006) Elements of Information Theory, 2nd Edition. Hoboken, N J: Wiley Dann J F, Buhl E H. (1987) Retinal ganglion cells projecting to the accessory optic system in the rat. J Comp Neurol 262(1): 141-58.

Dedek K, et al (2008) Ganglion cell adaptability: does the coupling of horizontal cells play a role? PLoS One. 3(3): e1714.

Douglas R M et al (2005) Independent visual threshold measurements in the two eyes of freely moving rats and mice using a virtual-reality optokinetic system. Vis Neurosci. 22(5):677-84.

Duda R O, Hart P E (2001) Pattern Classification (2nd Edition) Wiley, NY,

Enroth-Cugell et al., (1966) The contrast sensitivity of retinal ganglion cells of the cat. J Physiol 187(3): 517-52.

European Patent Application No. 19891976

Famulare M, Fairhall A. (2010) Feature selection in simple neurons: how coding depends on spiking dynamics. *Neural Comput* 22(3): 581-98

Field et al., (2007) Information processing in the primate retina: circuitry and coding. Annu Rev Neurosci 30: 1-30.

Fitzgerald et al. (1994) Retinal signal transmission in Duchenne muscular dystrophy. *J Clin Invest* 93: 2425-30.

Foley J M, Legge G E (1981) Contrast detection and near-threshold discrimination in human vision. Vision Res. 21(7):1041-53.

Franck K H. (2002) A model of a nucleus 24 cochlear implant fitting protocol based on the electrically evoked whole nerve action potential. Ear Hear. 223(1 Suppl):67S-71S.

Fried S, Werblin F, McMahon M J (2006) US Pat. 2006/0129207 Mimicking neural coding in retinal ganglion cells with short pulse electrical stimulation. In: (US, ed).

Friedman D S, O'Colmain B J, Munoz B, Tomany S C, McCarty C, de Jong P T V M, Nemesure B, Mitchell P, Kempen J, Eye Diseases Prevalence Research Group (2004) Prevalence of age-related macular degeneration in the United States. Arch Ophthalmol 122:564-572.

Geisler W S (200). Visual perception and the statistical properties of natural scenes. Annu Rev. Psychol. 59:167-92 (2008)

Gerding H, Benner F P, Taneri S (2007) Experimental implantation of epiretinal retina implants (EPI-RET) with an IOL-type receiver unit. J Neural Eng 4:S38-49.

Giolli R A, Blanks R H I, Lui F. (2005) The accessory optic system: basic organization with an update on connectivity, neurochemistry, and function. Prog Brain Res 151: 407-40.

Golan L, Reutsky I, Farah N & Shoham S. (2009) Design and characteristics of holographic neural photo-stimulation systems, Journal of Neural Engineering 6 066004, (2009)

Graham-Rowe D (2009) A Brighter Future for Retinal Implants. In: Technology Review, http://www.technology-review.com/biomedicine/23539/. Boston, Mass.: MIT.

Greenberg K P, et al. (2011). Differential Targeting of Optical Neuromodulators to Ganglion Cell Soma and Dendrites Allows Dynamic Control of Center-Surround Antagonism. Neuron 69, 713-720.

Grinstead C M and Snell J L (1997) Introduction to Probability. American Mathematical Society; 2nd Revised edition Grossman N, Poher V, Grubb M S, Kennedy G T, Nikolic K, McGovern B, Palmini R B, Gong Z, Drakakis E M, Neil, M A A, Dawson M D, Burrone J, Degenaar P. (2010) Multi-site optical excitation using ChR2 and micro-LED array. *J. Neural Eng,* 7(1):1-13.

Guiraud D, et al (2006) An implantable neuroprosthesis for standing and walking in paraplegia: 5-year patient follow-up. J Neural Eng. 3(4):268-75.

Han et al, (2009), Millisecond-Timescale Optical Control of Neural Dynamics in the Nonhuman Primate Brain, *Neuron* 62, 191-198.

Hand D J. (1981) Discrimination and classification. Wiley Series in Probability and Mathematical Statistics.

Hochberg L R, et al (2006) Neuronal ensemble control of prosthetic devices by a human with tetraplegia. Nature 442(7099):164-71.

Huberman A D, Manu M, Koch S M, Susman M W, Lutz A B, Ullian E M, Baccus S A, Barres B A (2008) Architecture and activity-mediated refinement of axonal projections from a mosaic of genetically identified retinal ganglion cells. Neuron. 2008 Aug. 14; 59(3):425-38.

Huberman A D, Wei W, Elstrott J, Stafford B K, Feller M B, Barres B A (2009) Genetic Identification of an On-Off Direction-Selective Retinal Ganglion Cell Subtype Reveals a Layer-Specific Subcortical Map of Posterior Motion. *Neuron.* 62(3):327-334.

Ivanova E, Pan Z-H (2009) Evaluation of the adeno-associated virus mediated long-term expression of channel-rhodopsin-2 in the mouse retina. *Molecular Vision* 15:1680-1689

Izhikevich E M (2007) Dynamical systems in neuroscience: the geometry of excitability and bursting. Cambridge, Mass.: MIT Press Izhikevich E M (2010) Hybrid spiking models. Review. Phil. Trans. R. Soc. A (2010) 368, 5061-5070

Jacobs A L et al (2009), Ruling out and ruling in neural codes. Proc Natl Acad Sci USA. 106(14):5936-41.

Jeffreys, Harold (1961). The Theory of Probability. The Oxford University Press.

Kass R E, Ventura V, Brown E N. (2005) Statistical issues in the analysis of neuronal data. J Neurophysiol 94(1): 8-25.

Kawasaki et al., Variability of the relative afferent pupillary defect. *Am J Ophthalmol* (1995). 120: 622-633.

Kay M A, Glorioso J C, Naldini L. (2001) Viral vectors for gene therapy: the art of turning infectious agents into vehicles of therapeutics. Nat Med. 7(1):33-40. Review.

Kelly S, Shire D, Chen J, Doyle P, Gingerich M, Drohan W, Theogarajan L, Cogan S, Wyatt J, Rizzo J I (2009) Realization of a 15-channel, hermetically-encased wireless subretinal prosthesis for the blind. In, pp 200-203.

Kibbel S, Harscher A, Wrobel W-G, Zrenner E, Rothermel A (2009) Design and Performance of an improved active subretinal chip. In: World Congress on Medical Physics and Biomedical Engineering, Sep. 7-12, 2009, Munich, Germany (Kim S I, Suh T S, Dossel O, Schlegel W C, eds), pp 192-195: Springer Berlin Heidelberg.

Kim R H, et al (2010) Waterproof AlInGaP optoelectronics on stretchable substrates with applications in biomedicine and robotics. Nat Mater 9(11):929-37. Epub 2010 Oct. 17.

Koilkonda R D, Hauswirth W W, Guy J. (2009) Efficient expression of self-complementary AAV in ganglion cells of the ex vivo primate retina. Mol Vis. 15:2796-802.

Kuffler S W. (1953) Discharge patterns and functional organization of mammalian retina. J Neurophysiol 16(1): 37-68.

Lagali P S, Balya D, Awatramani G B, Munch T A, Kim D S, Busskamp V, Cepko C L, Roska B (2008) Light-activated channels targeted to ON bipolar cells restore visual function in retinal degeneration. Nat Neurosci 11:667-675.

Lee et al., (1998), Variability and Correlated Noise in the Discharge of Neurons in Motor and Parietal Areas of the Primate Cortex J. *Neurosci, 18*:1161

Lei L, Han D. (2010) Efficient transduction of spiral ganglion cells using adenovirus type 5 vector in the rat. Acta Otolaryngol. 130(7):810-4.

Lesica N A et al. (2007) Adaptation to stimulus contrast and correlations during natural visual stimulation. Neuron 55(3): 479-491.

Lettvin et al., (1959) What the frog's eye tells the frog's brain. Proceedings of the Institute of Radio Engineers 47(11): 1940-51.

Lewicki M S. (2002) Efficient coding of natural sounds. Nat Neurosci. 5(4):356-63.

Liao et al. (2007) In vivo gene delivery in the retina using polyethylenimine. *BioTechniques* 2007, 42:285-288.

Liu Y, et al (2007) Promoter effects of adeno-associated viral vector for transgene expression in the cochlea in vivo. Exp Mol Med. 39(2):170-5.

Loewenstein J I, Montezuma S R, Rizzo J F, III (2004) Outer Retinal Degeneration: An Electronic Retinal Prosthesis as a Treatment Strategy. Arch Ophthalmol 122:587-596.

Luebke A E, et al (2009) Adenoviral and AAV-mediated gene transfer to the inner ear: role of serotype, promoter, and viral load on in vivo and in vitro infection efficiencies. Adv Otorhinolaryngol. 266:87-98.

Maguire et al. Safety and efficacy of gene transfer for Leber's congenital amaurosis. N Engl J Med (2008) 358: 2240-2248.

Mancuso et al., (2009) Gene therapy for red-green colour blindness in adult primates. Nature 461(7265): 784-7.

Martin et al. 2002. Gene delivery to the eye using adeno-associated viral vectors. *Methods* 28:267-275.

McGowan M H et al (1998) Characterization of the Mouse Aldose Reductase Gene and Promoter in a Lens Epithelial Cell Line. Mol Vis 1998; 4:2

McLaughlin S K, Collis P, Hermonat P L, Muzyczka N. (1988) Adeno-associated virus general transduction vectors: analysis of proviral structures. J Virol. 62(6):1963-73.

Meytlis M, Bomash I, Pillow J W, Nirenberg S. (2009) Assessing the importance of correlated firing using large populations of neurons. *Society for Neuroscience*. Program No. 165.3.

Morgans C W, et al (2009) TRPM1 is required for the depolarizing light response in retinal ON-bipolar cells. Proc Natl Acad Sci USA 106(45): 19174-8.

Moritz C T, et al (2008) Direct control of paralysed muscles by cortical neurons. Nature 456(7222):639-42

Nanduri D, Humayun M, Greenberg R, McMahon M, Weiland J (2008) Retinal prosthesis phosphene shape analysis. In: 30th Annual International Conference of the IEEE Engineering in Medicine and Biology Society, pp 1785-1788. Vancouver, BC.

Nichols Z, Meytlis M, Nirenberg S. (2010) Correlations play a negligible role in coding white noise and natural scene stimuli in complete retinal populations. Submitted.

Nirenberg S (2000) Photoablation of cells expressing beta-galactosidase. *Methods Mol Biol.* 135:475-80

Nirenberg S and Cepko, C (1993). Targeted ablation of diverse cell classes in the nervous system in vivo. *J Neurosci.* 13(8):3238-51.

Nirenberg S and Latham P E. (1998) Population coding in the retina. *Curr. Opin. Neurobiol.* 8(4):488-493

Nirenberg S and Meister M. (1997). The light response of retinal ganglion cells is truncated by a displaced amacrine circuit. *Neuron* 18:637-650

Nirenberg S et al (2001) Retinal ganglion cells act largely as independent encoders. Nature 411(6838):698-701.

Nirenberg S et al. (2010) Heterogeneous response dynamics in retinal ganglion cells: the interplay of predictive coding and adaptation. *J Neurophysiol* 103(6): 3184-94

Norcia, A M, and Tyler, C W (1985) Spatial frequency sweep VEP: visual acuity during the first year of life. Vision Res. 25(10):1399-408

Norcia, A M, et al (1989). Measurement of spatial contrast sensitivity with the swept contrast VEP. Vision Res. 1989; 29(5):627-37.

Okuyama et al. (1993). Binocular infrared optometer for measuring accommodation in both eyes simultaneously in natural-viewing conditions Applied Optics, Vol. 32. No 22, p. 4147

Pandarinath et al (2010a) A novel mechanism for switching a neural system from one state to another. Front Comput Neurosci. 31; 4:2.

Pandarinath et al (2010b) Symmetry breakdown in the ON and OFF pathways of the retina at night: functional implications. J Neurosci 30(30): 10006-14.

Paninski L, Pillow J, Lewi J. (2007) Statistical models for neural encoding, decoding, and optimal stimulus design. Prog Brain Res. 165:493-507.

Paninski L (2004) Maximum likelihood estimation of cascade point-process neural encoding models. *Network* 15(4): 243-62

Panzeri S, et al (2007) Correcting for the sampling bias problem in spike train information measures. J Neurophysiol. 98(3):1064-72. Review.

Pelli D G, Robson J G, & Wilkins A J (1988) The design of a new letter chart for measuring contrast sensitivity. Clinical Vision Sciences 2, 187-199

Perry V H, Silveira L C. (1988) Functional lamination in the ganglion cell layer of the macaque's retina. Neuroscience. 25(1):217-23.

Petrs-Silva et al., (2009) High-efficiency transduction of the mouse retina by tyrosine-mutant AAV serotype vectors. Mol Ther 17(3): 463-71.

Petersen-Jones et al., (2009) AAV retinal transduction in a large animal model species: comparison of a self-complementary AAV2/5 with a single-stranded AAV2/5 vector. Mol Vis 15: 1835-42.

Pillow J W, Shlens J, Paninski L, Sher A, Litke A M, Chichilnisky E J, Simoncelli E P. (2008) Spatio-temporal correlations and visual signalling in a complete neuronal population. *Nature* 454(7207): 995-9

Prusky G T, et al (2004) Rapid quantification of adult and developing mouse spatial vision using a virtual optomotor system. Invest Ophthalmol Vis Sci. 45(12):4611-6.

Published PCT Application WO1996013598
Published PCT application WO1998048027
Published PCT Application WO2000015822
Published PCT application WO2001094605
Published PCT application WO2002082904
Published PCT application WO2003047525
Published PCT application WO2003080648
Published PCT application WO2003093479
Published PCT application WO2003104413
Published PCT application WO2005080573
Published PCT application WO2007127428
Published PCT application WO2010011404
Pun L (1969), *Introduction to Optimization Practice*, ISBN 471-70233-1
Purpura K, Tranchina D, Kaplan E, Shapley R M. (1990) Light adaptation in the primate retina: analysis of changes in gain and dynamics of monkey retinal ganglion cells. Vis Neurosci 4(1): 75-93.
Rolls E T, Baylis G C, Leonard C M. Role of low and high spatial frequencies in the face-selective responses of neurons in the cortex in the superior temporal sulcus in the monkey. Vision Res. 1985; 25(8):1021-35.
Rubinstein J T, Miller C A. (1999) How do cochlear prostheses work? Curr Opin Neurobiol. 9(4):399-404.
Sambrook et al, "Molecular Cloning. A Laboratory Manual", 2d ed., Cold Spring Harbor Laboratory, New York (1989)
Sauer B. (1987) Functional expression of the cre-lox site-specific recombination system in the yeast *Saccharomyces cerevisiae*. Mol Cell Biol. 7(6):2087-96.
Sellick P M, et al (1982) Modulation of responses of spiral ganglion cells in the guinea pig cochlea by low frequency sound. Hear Res. 7(2):199-221. Shapley R M, Victor J D. (1981) How the contrast gain control modifies the frequency responses of cat retinal ganglion cells. J Physiol. 318:161-79.
Sharpee T O et al. (2008) On the Importance of Static Nonlinearity in Estimating Spatiotemporal Neural Filters With Natural Stimuli. J Neurophysiol 99(5): 2496-509
Sheridan C (2011) Gene Therapy finds its niche Nature Biotechnology 29(2):121-128
Siegert S, Scherf B G, Punta K D, Didkovsky N, Heintz N, Roska B (2009). Genetic address book for retinal cell types. *Nature Neuroscience*. 12:1197-1204.
Simoncelli et al. (2004) Characterization of neural responses with stochastic stimuli. The cognitive neurosciences: 327-38
Simonelli et al. (2010) Gene Therapy for Leber's Congenital Amaurosis is Safe and Effective Through 1.5 Years After Vector Administration, *Molecular Therapy* 18 3, 643-650.
Sinclair J R, et al (2004). Selective ablation of a class of amacrine cells alters spatial processing in the retina. J Neurosci. 24(6):1459-67.
Sjostrand et al. (1999). Morphometric study of the displacement of retinal ganglion cells subserving cones within the human fovea. Graefe's Arch Clin Exp Ophthalmol 237: 1014-1023.
Soucy E R et al. (1998) A novel signaling pathway from rod photoreceptors to ganglion cells in mammalian retina. *Neuron* 21:481-493
Stone et al., (1993) Response properties of ganglion cells in the isolated mouse retina. Vis Neurosci 10(1): 31-9.
Strong S P, et al (1998) On the application of information theory to neural spike trains. Pac Symp Biocomput. 621-32.
Thyagarajan S, van Wyk M, Lehmann K, Lowel S, Feng G, Wässle H (2010) Visual function in mice with photoreceptor degeneration and transgenic expression of channelrhodopsin 2 in ganglion cells. J Neurosci 30:8745-8758.
Tomita H, Sugano E, Isago H, Hiroi T, Wang Z, Ohta E, Tamai M (2010) Channelrhodopsin-2 gene transduced into retinal ganglion cells restores functional vision in genetically blind rats. Exp Eye Res 90:429-436.
Troy J B, Bohnsack D L, Chen J, Guo X, Passaglia C L. (2005) Spatiotemporal integration of light by the cat X-cell center under photopic and scotopic conditions. Vis Neurosci 22(4): 493-500.
Troy J B, Bohnsack D L, Diller L C. (1999) Spatial properties of the cat X-cell receptive field as a function of mean light level. Vis Neurosci 16(6): 1089-104.
Turchinovich et al. (2010) Non-viral siRNA delivery into the mouse retina in vivo. *BMC Ophthalmology* 10:25.
U.S. Pat. No. 7,149,586
U.S. Pat. No. 5,856,152
U.S. Pat. No. 5,871,982
U.S. Pat. No. 6,533,798
U.S. Patent Publication 20080221653
U.S. Patent Publication 20080249588
U.S. Patent Publication 20090088399
U.S. Patent Publication 20090326623,
U.S. Patent Publication 20100272688
U.S. Patent Publication 20100234273
U.S. Patent Publication Nos. 20070261127
Ueda et al, (1997) The mGluR6 5' upstream transgene sequence directs a cell-specific and developmentally regulated expression in retinal rod and ON-type cone bipolar cells. *J Neurosci.* 17(9):3014-23.
van Adel et al. (2003) Delivery of ciliary neurotrophic factor via lentiviral-mediated transfer protects axotomized retinal ganglion cells for an extended period of time. *Hum. Gene Ther.* 14:103-115.
Victor J D, Shapley R M. (1979) The nonlinear pathway of Y ganglion cells in the cat retina. J Gen Physiol. 74(6):671-89.
Victor J D. (1987) The dynamics of the cat retinal X cell centre. *The Journal of Physiology* 386(1): 219.
Volgyi B, Deans M R, Paul D L, Bloomfield S A (2004) Convergence and Segregation of the Multiple Rod Pathways in Mammalian Retina. J Neurosci 24(49):11182-11192.
Walther W, Stein U. (2000) Viral vectors for gene transfer: a review of their use in the treatment of human diseases. Drugs. 60(2):249-71. Review.
Wang H, et al (2011) Efficient cochlear gene transfection in guinea-pigs with adeno-associated viral vectors by partial digestion of round window membrane. Gene Ther. 2011 Jun. 23. [Epub ahead of print]
Wassle H. (2004) Parallel processing in the mammalian retina. Nat Rev Neurosci 5(10): 747-57.
Wells et al. (2005) Optical stimulation of neural tissue in vivo. Optics Letters 30(5):504-506,
Winter J O, Cogan S F, Rizzo J F I (2007) Retinal prostheses: current challenges and future outlook. J Biomater Sci Polym Ed 18:1031-1055.
Wright A F. (1997) Gene therapy for the eye. Br J Ophthalmol 81(8): 620-623 Review.
Yonehara K, Ishikane H, Sakuta H, Shintani T, Nakamura-Yonehara K, et al. (2009) Identification of Retinal Ganglion Cells and Their Projections Involved in Central Transmission of Information about Upward and Downward Image Motion. PLoS ONE 4(1): e4320.
Yonehara K, Shintani T, Suzuki R, Sakuta H, Takeuchi Y, et al. (2008) Expression of SPIG1 Reveals Development of a Retinal Ganglion Cell Subtype Projecting to the Medial Terminal Nucleus in the Mouse. PLoS ONE 3(2): e1533.

Zeng et al. (2009) Cochlear Damage Changes the Distribution of Vesicular Glutamate Transporters Associated with Auditory and Nonauditory Inputs to the Cochlear Nucleus, J. Neurosci. 4210-4217.

Zhang Y, Ivanova E, Bi A, Pan Z-H (2009) Ectopic expression of multiple microbial rhodopsins restores ON and OFF light responses in retinas with photoreceptor degeneration. J Neurosci 29:9186-9196.

Zierhofer C M et al (1995) Electronic Design of a Cochlear Implant for Multichannel High-Rate Pulsatile Stimulation Strategies. IEEE Transactions on Rehabilitation Engineering 3(1): 112-116.

Zrenner E, et al (2009) Subretinal Microelectrode Arrays Allow Blind Retinitis Pigmentosa Patients to Recognize Letters and Combine them to Words. BMEI '09. 2nd International Conference on Biomedical Engineering and Informatics. Issue Date: 17-19 Oct. 2009. ISBN: 978-1-4244-4132-7. Pages 1-4.

What is claimed is:

1. A method improving or restoring neural function in a mammalian subject in need thereof, the method comprising:
using an input receiver to record an input signal generated by a first set of nerve cells;
using an encoder unit comprising a set of encoders to generate a set of coded outputs in response to the input signal, wherein:
generating the set of coded outputs comprises transforming the input signal based on experimental neural function data of an unimpaired subject; and
the experimental neural function data comprises:
a first response in the unimpaired subject corresponding to the first set of nerve cells, and
a second response in the unimpaired subject corresponding to a second set of nerve cells;
using the coded outputs to drive an output generator; and
using the output generator to activate the second set of nerve cells wherein the second set of nerve cells is separated from the first set of nerve cells by an impaired set of signaling cells;
wherein the second set of nerve cells produces a response that is substantially the same as the second response in the unimpaired subject; and
wherein said generating the set of coded outputs further comprises tuning the input signal based on a gain factor corresponding to:
a magnitude difference between the first response in the unimpaired subject and the input signal generated by the first set of nerve cells; or
a size difference between the unimpaired subject and the mammalian subject.

2. The method of claim 1, wherein:
the first set of nerve cells comprises supplementary motor area neurons;
the second set of nerve cells comprises spinal motor neurons; and
the impaired set of signaling cells comprises primary motor cortex neurons.

3. The method of claim 1, wherein the transformation further comprises:
generating the input signal as a time resolved series of values $\vec{a}$ corresponding to the pattern of neural activity generated in the first set of nerve cells; and
transforming the values $\vec{a}$ to a time resolved series of output values $\vec{c}$ by applying a transformation.

4. The method of claim 3, wherein $\vec{c}$ is a vector valued function, wherein each element of the vector is a value corresponding to a firing rate of a single cell or small group of cells from the second set of nerve cells.

5. The method of claim 4, wherein $\vec{c}$ is a vector valued function, wherein each element of the vector is a value corresponding to the total firing rate of the second set of nerve cells.

6. The method of claim 4, wherein $\vec{c}$ is a vector valued function, wherein each element of the vector is a value corresponding to the total firing rate of a respective subpopulation of the second set of nerve cells, and wherein the second set of nerve cells comprises motor neurons, and each subpopulation innervates a different respective muscle.

7. The method of claim 3, wherein the transformation further comprises:
a set of spatiotemporal linear filters; and
a nonlinear function.

8. The method of claim 7, wherein the spatiotemporal linear filters are parameterized by a set of K weights, and wherein K is in the range of 5-20.

9. The method of claim 7, wherein the nonlinear function is parameterized as a cubic spline function with M knots.

10. The method of claim 9, wherein M is in the range of 2-20.

11. The method of claim 7, wherein the spatiotemporal linear filters operate over P time bins, each having a duration Q.

12. The method of claim 11, wherein P is in the range of 5-20.

13. The method of claim 12, wherein Q is in the range of 10 ms-100 ms.

14. The method of claim 1, wherein the transformation is characterized by a set of parameters; and wherein the set of parameters corresponds to a result of fitting the transformation to the experimental neural function data obtained by:
exposing the unimpaired subject to a broad range of reference stimuli;
recording the first response in the unimpaired subject corresponding to the first set of nerve cells;
recording the second response in the unimpaired subject corresponding to the second set of nerve cells.

15. The method of claim 14, wherein the second response comprises the firing rate of individual nerve cells.

16. The method of claim 14, wherein the broad range of reference stimuli comprises at least one chosen from the list consisting of:
motion in an environment comprising one or more obstacles;
manipulation of objects having different weights; and
moving a cursor to one of several locations on a display.

17. The method of claim 14, wherein the reference stimuli comprises an unpredictable load, and wherein the unpredictable load comprises an irregular terrain, grade, or load.

18. A device improving or restoring neural function in a mammalian subject in need thereof, the device comprising:
an input receiver configured to record an input signal generated by a first set of nerve cells;
an output generator configured to activate a second set of nerve cells, wherein the second set of nerve cells is separated from the first set of nerve cells by an impaired set of signaling cells; and an encoder unit comprising a set of encoders that generate a set of coded outputs in response to the input signal, wherein:
  the encoder unit is configured to generate the set of coded outputs by transforming the input signal based on experimental neural function data of an unimpaired subject;
  the experimental neural function data comprises:
    a first response in the unimpaired subject corresponding to the first set of nerve cells, and
    a second response in the unimpaired subject corresponding to the second set of nerve cells; and
  the set of coded outputs control the output generator to activate the second set of nerve cells to produce a response to the input signal that is substantially the same as the second response in the unimpaired subject; and
  wherein the encoder unit is configured to generate the set of coded outputs by, at least in part, tuning the input signal based on a gain factor corresponding to:
    a magnitude difference between the first response in the unimpaired subject and the input signal generated by the first set of nerve cells; or
    a size difference between the unimpaired subject and the mammalian subject.

19. The device of claim 18, wherein the output generator comprises a light outputting device configured to selectively apply light to a light-activated transducer to activate the second set of nerve cells.

20. A non-transitory computer readable media having computer-executable instruction comprising instruction for executing steps comprising:
  recording an input signal generated by a first set of nerve cells;
  using an encoder unit comprising a set of encoders to generate a set of coded outputs in response to the input signal, wherein:
    generating the set of coded outputs comprises transforming the input signal based on experimental neural function data of an unimpaired subject; and
    the experimental neural function data comprises:
      a first response in the unimpaired subject corresponding to the first set of nerve cells, and
      a second response in the unimpaired subject corresponding to the second set of nerve cells; and
  using the coded outputs to control an output generator to activate the second set of nerve cells wherein the second set of nerve cells is separated from the first set of neurons by an impaired set of signaling cells;
  wherein the second set of nerve cells produces a response to the input signal that is substantially the same as the second response in the unimpaired subject; and
  wherein said generating the set of coded outputs further comprises tuning the input signal based on a gain factor corresponding to:
    a magnitude difference between the first response in the unimpaired subject and the input signal generated by the first set of nerve cells; or
    a size difference between the unimpaired subject and the mammalian subject.

* * * * *